(12) United States Patent
Goolsbee et al.

(10) Patent No.: US 10,786,531 B2
(45) Date of Patent: Sep. 29, 2020

(54) MINERAL SALT-SULFONIC ACID COMPOSITIONS AND METHODS OF USE

(71) Applicant: BMG PHARMA SPA, Milan (IT)

(72) Inventors: William A. Goolsbee, Gardnerville, NV (US); Jeffrey L. Lillard, Gig Harbor, WA (US)

(73) Assignee: BMG PHARMA SPA, Milan (IT)

( * ) Notice: Subject to any disclaimer, the term of this patent is extended or adjusted under 35 U.S.C. 154(b) by 14 days.

(21) Appl. No.: 16/449,632

(22) Filed: Jun. 24, 2019

(65) Prior Publication Data

US 2019/0307792 A1 Oct. 10, 2019

Related U.S. Application Data

(63) Continuation of application No. 14/582,839, filed on Dec. 24, 2014, now abandoned, which is a continuation of application No. 13/797,360, filed on Mar. 12, 2013, now abandoned, which is a continuation of application No. 13/264,690, filed as application No. PCT/US2010/031319 on Apr. 15, 2010, now abandoned.

(60) Provisional application No. 61/169,540, filed on Apr. 15, 2009.

(51) Int. Cl.
| | | |
|---|---|---|
| *A61K 33/30* | (2006.01) | |
| *A61P 17/02* | (2006.01) | |
| *A01N 41/08* | (2006.01) | |
| *A61K 31/185* | (2006.01) | |
| *A01N 25/24* | (2006.01) | |
| *A01N 37/36* | (2006.01) | |
| *A01N 55/02* | (2006.01) | |
| *A61K 9/00* | (2006.01) | |
| *A61K 31/28* | (2006.01) | |
| *A61K 38/40* | (2006.01) | |
| *A61K 31/145* | (2006.01) | |
| *A61K 31/191* | (2006.01) | |
| *A61K 38/48* | (2006.01) | |
| *A61K 9/08* | (2006.01) | |

(52) U.S. Cl.
CPC .............. *A61K 33/30* (2013.01); *A01N 25/24* (2013.01); *A01N 37/36* (2013.01); *A01N 55/02* (2013.01); *A61K 9/006* (2013.01); *A61K 9/0014* (2013.01); *A61K 31/145* (2013.01); *A61K 31/185* (2013.01); *A61K 31/191* (2013.01); *A61K 31/28* (2013.01); *A61K 38/40* (2013.01); *A61K 38/482* (2013.01); *A61K 9/0034* (2013.01); *A61K 9/08* (2013.01)

(58) Field of Classification Search
None
See application file for complete search history.

(56) References Cited

U.S. PATENT DOCUMENTS

| | | | |
|---|---|---|---|
| 5,700,782 A | 12/1997 | Cope et al. | |
| 5,997,852 A | 12/1999 | Yoneda et al. | |
| 6,716,813 B2 | 4/2004 | Lim et al. | |
| 2003/0236217 A1 | 12/2003 | Shalwitz et al. | |
| 2005/0147675 A1 | 7/2005 | Petrus | |
| 2005/0281762 A1 | 12/2005 | Modak et al. | |
| 2006/0127342 A1 | 6/2006 | Levis | |
| 2007/0264309 A1 | 11/2007 | Chollet et al. | |
| 2009/0030060 A1 | 1/2009 | Ebmeier et al. | |
| 2009/0076132 A1* | 3/2009 | Pekoe ................... | A61K 31/353 514/456 |
| 2010/0055053 A1 | 3/2010 | Ripley et al. | |

FOREIGN PATENT DOCUMENTS

| | | |
|---|---|---|
| JP | 363132820 A | 6/1988 |
| WO | 2007134335 A2 | 11/2007 |

OTHER PUBLICATIONS

Farstvedt et al., Clin Tech Equine Pract 3:164-172, 2004 (Year: 2004).*
Sandari et al., Comp Clin Pathol (2006) 15:237-243 (Year: 2006).*
Abstract 15-098, Flook et al., Gelclair(R) vs Benzydamine in a Randomized Controlled Study in Patients with Oral Mucositis Due to Radical Radiotherapy, Supportive Care in Cancer, 2005; 13(6): 443-444 (Flook Abstract begins at bottom p. 443).
Apte and Ugwu, Pharm. Tech. Mar. 2003, pp. 46-60.
Buchsel P.C., et al., 'Polyninylpyrrolidone-sodium hyaluronate gel (Gelclair(r)): a bioadherent oral gel for the treatment of oral mucositis and other painful oral lesions', Expert Opinion on Drug Metabolism & Toxicology, 4:11, 1449-1454.
Cetiner et al, "Taurine protects against methotrexate-induced toxicity and inhibits leukocyte death", Toxicology and Applied Pharmacology 209 (2005) 39-50.
Ertekin et al., "Zinc sulfate in the prevention of radiation-induced oropharyngeal mucositis: a prospective, placebo controlled, randomized study", Int. J. Radiation Oncology Biol. Phys., vol. 58, No. 1, pp. 167-174, 2004.
Gelclair(R) 501(k) Summary documents, 2001 (GFDA).
Gennaro Ed., Remington, The Science and Practice of Pharmacy, 20th Edition, 2000, chapter 39, by J G Naim, Entilted: Solutions, Emulsions, Suspensions and Extracts.
Harris "Cancer treatment-induced mucositis pain: strategies for assessment and management", Ther. and Clin. Risk Man. 2006:2(3) 251-258.
IJAPBC, vol. 1(1), Jan.-Mar. 2012, pp. 21-34.

(Continued)

*Primary Examiner* — Juliet C Switzer
*Assistant Examiner* — Joseph Fischer
(74) *Attorney, Agent, or Firm* — Silvia Salvadori, P.C.; Silvia Salvadori

(57) ABSTRACT

The present disclosure generally relates to the medical use of compositions comprising a mineral salt and a sulfonic acid for prevention and/or treatment of one or more mucosal diseases, disorders, or conditions or one or more dermal diseases, disorders, or conditions.

1 Claim, 4 Drawing Sheets

Specification includes a Sequence Listing.

(56) References Cited

OTHER PUBLICATIONS

Lopes et al., "Biomaterials", 24 (2003) 1279-1284.
Maxi/Guard(R) Orazn(R) product literature, 2006, 2 pages.
Maxi/Guard(R) Orazn(R) product literature, date approx. 2005, 2 pages.
Nebendahl, K., 2000. Routes of administration. In Krinke G J ed. The laboratory Rat Academic Press. London. pp. 463-483.
Taurine properties summary, source: http://www.chemicalbook.com/ChemicalProductProperty_EN_CB2742654.htm, 3 pages.

* cited by examiner

MINERAL SALT-SULFONIC ACID COMPOSITIONS AND METHODS OF USE

CROSS-REFERENCE TO RELATED APPLICATIONS

This application is a continuation of U.S. patent application Ser. No. 14/582,839 filed Dec. 24, 2014, which is a continuation of U.S. patent application Ser. No. 13/797,360 filed Mar. 12, 2013, now abandoned, which is a continuation of U.S. patent application Ser. No. 13/264,690, filed on May 31, 2012, now abandoned, which is U.S. national stage application filed under 35 U.S.C. § 371 of International Patent Application No. PCT/US2010/031319, filed on Apr. 15, 2010, which claims priority to and the benefit of U.S. Provisional Application No. 61/169,540 filed on Apr. 15, 2009, the contents of all of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 170169_401C2_SEQUENCE_LISTING.txt. The text file is 84 KB, was created on Dec. 23, 2014 and is being submitted electronically via EFS-Web.

BACKGROUND

Field

The present disclosure generally relates to the medical use of compositions comprising a mineral salt and a sulfonic acid for prevention and/or treatment of one or more mucosal or dermal diseases, disorders, or conditions.

Description of the Related Art

Prolonged and recurrent inflammation associated with dermal or mucosal disorders can result in extensive damage to the mucosal epithelium, leading to severe ulceration, pain, and infection and may ultimately require surgery. In addition, damaged mucosal epithelium may be associated with severe malabsorption of nutrients, diarrhea, weight loss, and the frequent need for oral and parenteral nutrient supplementation. Currently, few therapies are available for patients that act to enhance nutrient absorption and restore the functional integrity of a mucosal or dermal epithelium.

Atrophic vaginitis (AV) is known to affect many women. Women who are in mid-life or beyond and who have declining estrogen levels often present symptoms of AV. An estimated 10-40% of postmenopausal women have symptoms of AV; however, despite the prevalence of symptoms, only 20-25% of symptomatic women seek medical attention (Cardozo et al., *Obstet. Gynecol.* 92:722-27, 1998; Pandit et al., *Am. J. Med. Sci.* 314:228-31, 1997). Through identification of and intervention in this often overlooked and under-diagnosed condition, the urogenital health and quality of life of a large patient population could be improved.

A number of over-the-counter (OTC) vaginal moisturizer and lubricant products are considered first-line nonhormonal treatments for vaginal dryness. This option is appropriate for women concerned about hormone use, who have minimal physiologic changes or symptoms, or those who are not candidates for estrogen treatment. For example, REPLENS®, a polycarbophil-based vaginal moisturizing gel has been shown to restore vaginal pH and improve cytological morphology (Dupont et al., *Maturitas* 13:297-311, 1991; Leiblum et al., *JAMA* 249:2159-98, 1983). However, definitive efficacy data are lacking for almost all OTC preparations used for treating atrophic vaginitis.

Moreover, some women may experience sensitivity or allergy to components of moisturizers or lubricants. OTC products may contain warming additives, dyes, perfume, bactericides, or spermicides that can further irritate already sensitive, dry vaginal mucosa. Other common vaginal and vulvar irritants include benzocaine, chlorhexidine, preservatives (parabens and propylene glycol), and condoms made of latex or containing lanolin. Thus, an unfulfilled need remains for a first-line product that can treat or relieve symptoms of atrophic vaginitis.

Another unmet medical need includes treatment of persons with oral mucositis. Oral mucositis is a significant side effect of cancer therapy and bone marrow transplantation, but it is not adequately managed by current approaches (Sonis, "Oral Complications," In *Cancer Medicine*, pp. 2381-2388, 1993a; Holland et al., Eds., Lea and Febiger, Philadelphia; Sonis, "Oral Complications in Cancer Therapy." In *Principles and Practice of Oncology*, pp. 2385-2394, 1993b; DeVitta et al., Eds., J. B. Lippincott, Philadelphia). Oral mucositis occurs in almost 100% of patients receiving chemotherapy and radiotherapy for head and neck tumors and in about 90% of children with leukemia. About 40% of patients treated with chemotherapy for other tumors develop oral problems during each exposure to the chemotherapeutic agent (Sonis, 1993b, supra). Additionally, approximately 75% of patients undergoing bone marrow transplantation, both autologous and allogeneic, develop mucositis (Woo et al., *Cancer* 72:1612-1617, 1993). Current estimates indicate that about 400,000 patients suffer from oral mucositis annually in the United States alone (Graham et al., *Cancer Nursing* 16:117-122, 1993). Given that patients often receive multiple cycles of chemo- and/or radiotherapy, an estimated 1,000,000 incidences of oral mucositis occur per year in the United States.

A variety of approaches for treating oral mucositis, including mitigation of the potential for subsequent oral infections, have been tested with limited success. For example, the use of an allopurinol mouthwash, an oral sucralfate slurry, and pentoxifylline were reported in preliminary studies to result in a decrease in mucositis. However, subsequent randomized and controlled studies have failed to demonstrate any benefit (Loprinzi et al., *Sem. Oncol.* 22 (S3):95-97, 1995; Epstein et al., *Int. J. Radial. Oncol. Biol. Phys.* 28:693-698, 1994; Verdi et al., *Oral Surg. Oral Med. Oral Pathol. Oral Radiol. Endod.* 80:36-42, 1995).

Other treatments have been directed at decreasing oral flora and minimizing extent of infection as means to manage oral ulcerations. For example, systemic treatment with granulocyte-macrophage colony-stimulating factor (GM-CSF) has been shown to result in a decreased incidence of oral mucositis, presumably by allowing for more rapid neutrophil recovery and thus an improved ability to combat infection (Chi et al., *J. Clin. Oncol.* 13:2620-2628, 1995). However, in at least one study GM-CSF was reported to exacerbate mucositis (Cartee et al., *Cytokine* 7:471-477, 1994).

Benzydamine hydrochloride, a nonsteroidal drug with analgesic and antimicrobial properties, has been studied both in patients undergoing radiation therapy and in patients receiving intra-arterial chemotherapy (Epstein et al., *Oral Surg. Oral Med. Oral Pathol.* 62:145-148, 1986; Epstein et al., *Int. J. Radiat. Oncol. Biol. Phys.* 16:1571-1575, 1989). Chlorhexidine, an antimicrobial mouth rinse, has also been used extensively in the treatment and prevention of oral mucositis (Ferretti et al., *Bone Marrow Transplan.* 3:483-493, 1990; Weisdorf et al., *Bone Marrow Transplan.* 4:89-95, 1989). However, the efficacy of chlorhexidine has been observed to be significantly decreased in saliva, and this compound is relatively ineffective against the Gram negative bacteria that tend to colonize the oral cavity in patients undergoing radiation therapy (Spijkervet et al., *Oral Surg. Oral Med. Oral Pathol.* 69:444-449, 1990). In addition, at least one study has shown that the use of chlorhexidine may be detrimental and result in a higher incidence of mucositis (Foote et al., *J. Clin. Oncol.* 12:2630-2633, 1994). Several studies have shown that the use of a vancomycin paste and antibiotic lozenges containing polymixin B, tobramycin, and amphotericin B in patients undergoing myelosuppressive chemotherapy or radiation therapy can result in a decrease in oral mucositis and in the incidence of sepsis due to alpha hemolytic streptococci (Barker et al., 1995, *J. Ped. Hem. Oncol.* 17:151-155; Spijkervet et al., 1991, *In Irradiation Mucositis, Munksgaard Press*, pp. 43-50).

However, despite the clear need for therapeutic compositions to simply and reliably treat oral mucositis, no drugs are currently approved for this indication. As a result no standard treatment is available for this mucosal disorder, and an unmet need remains.

BRIEF SUMMARY

Provided herein are methods for treating mucosal and dermal disorders. In one embodiment, a method is provided for treating a mucosal disorder or a dermal disorder in a subject, which method comprises administering to the subject a physiologically acceptable composition that comprises a mineral salt and a sulfonic acid. In one embodiment, the mucosal disorder comprises mucositis. In specific embodiments, mucositis comprises inflammation of mucosa of the gastrointestinal tract, bladder, esophagus, vagina, rectum, lung, a nasal cavity, an ear, or ocular mucosa. In another embodiment, the mucosal disorder comprises oral stomatitis, oral mucositis, an oral ulceration, inflammatory bowel disease (including Crohn's disease and ulcerative colitis), periodontitis, interstitial cystitis, or a wound. In yet other embodiments, the mucosal disorder comprises vaginal dryness, vaginal burning, vaginal ulceration, dyspareunia, leukorrhea, vulvar pruritus, vulvar burning, or atrophic vaginitis. In certain embodiments, the mucosal disorder is consequent to any one or more of hormone insufficiency, bone marrow transplant, chemotherapy, radiation therapy, viral infection, fungal infection, and bacterial infection. In a more specific embodiment, the mucosal disorder is consequent to one or both of chemotherapy and radiation therapy administered to the subject for treatment of a head and neck tumor, a leukemia, breast cancer, prostate cancer, pancreatic cancer, ovarian cancer, melanoma, liver cancer, lung cancer, urinary cancer, colon cancer, or HIV/AIDS. In still another specific embodiment, the viral infection is caused by a Herpes Simplex Virus or Varicella zoster virus. In other embodiments, the dermal disorder comprises diaper rash, skin dryness, dermatitis, eczema, psoriasis, erythema, acne, xerosis, and radical oxygen species-induced skin damage.

With respect to the methods described above and herein, in certain embodiments, the mineral salt comprised within the composition comprises (a) a mineral moiety selected from zinc, calcium, iron, copper, magnesium, manganese, cobalt, chromium, selenium, and vanadium and (b) a salt moiety selected from gluconate, acetate, ascorbate, and sulfate. In a more specific embodiment, the mineral salt is zinc gluconate, and the composition comprises from 0.25% (w/w) to 5.5% (w/w) zinc gluconate. In other specific embodiments, the mineral salt is zinc gluconate, and the composition comprises from between 0.20% (w/w) to 5.5% (w/w) zinc gluconate. Further with respect to the methods described above and herein, in certain embodiments, the sulfonic acid comprised within the composition is taurine and the composition comprises from between 0.25% (w/w) to 30% (w/w) taurine. In certain embodiments, the composition comprises from between 0.25% (w/w) to 5.5% (w/w) zinc gluconate and comprises from between 0.25% (w/w) to 30% (w/w) taurine. In more specific embodiments, the sulfonic acid is taurine, and the composition comprises from between 0.5% (w/w) and 4.0% (w/w) taurine. In another more specific embodiment, the sulfonic acid is taurine and the composition comprises from between 0.5% (w/w) and 8.0% (w/w) taurine. In still other specific embodiments, the composition comprises from between 0.25% (w/w) to 5.5% (w/w) zinc gluconate and from between 0.5% (w/w) and 8.0% (w/w) taurine. In other embodiments, the composition further comprises one or more of a flavoring agent, a mucoadhesive agent, a pH adjusting agent, a solubilizing agent, a viscosity modulating agent, and a stabilizing agent. In a more particular embodiment, the compositions described above and herein further comprise one or more of (a) from between 0.05% to 3.0% (w/w) glycyrrhetinic acid; (b) from between 0.04% to 15% (w/w) polyvinylpyrrolidone (PVP); (c) from between 0.01% to 5.0% (w/w) hyaluronic acid; and (d) from between 0.05% to 3.0% (w/w) glycerin. In other specific embodiments, the compositions comprising a mineral salt and a sulfonic acid (as described above and herein) further comprise one or more of (a) from between 0.05% to 3.0% (w/w) glycyrrhetinic acid; (b) from between 0.04% to 15% (w/w) polyvinylpyrrolidone (PVP); (c) from between 0.01% to 5.0% (w/w) hyaluronic acid; and (d) from between 0.05% to 5.0% (w/w) glycerin. In another specific embodiment, the compositions comprise (a) 0.5% (w/w) zinc gluconate, 1.0% (w/w) taurine, and 4.0% PVP (w/w); (b) 0.5% (w/w) zinc gluconate, 1.0% (w/w) taurine, and 8.0% PVP (w/w); or (c) 2.0% (w/w) zinc gluconate, 4.0% (w/w) taurine, and 4.0% PVP (w/w). In other specific embodiments, the composition comprises 0.5% (w/w) zinc gluconate and 1.0% (w/w) taurine. In still another specific embodiment, the composition comprises 2.5% (w/w) zinc gluconate and 5.0% (w/w) taurine. In still other particular embodiments, these compositions that comprise a mineral salt and a sulfonic acid, as described above and herein, further comprise a lactoferrin.

In particular embodiments, any one of the compositions described above and herein that is administered according to the methods described above and herein is a liquid, a solid, a gel, a paste, an emulsion, an ointment, a foam, or a spray. In other particular embodiments, the composition is delivered by a vehicle selected from a sponge, gel cap, suppository, and a lozenge. In certain embodiments, the composition has a pH between 3.0 and 8.5. In certain particular embodiments, the pH is between 3.5 and 4.5; and in such particular embodiments, the mucosal disorder is atrophic vaginitis. In other particular embodiments, the pH is between 5.5 and 7.5, and in a specific embodiment, the mucosal disorder is oral mucositis.

With respect to the methods described above and herein, the composition is administered one or more times per day, once every day, once every other day, once weekly, once biweekly, or once a month. In a particular embodiment, the compositions described herein and above are administered topically, or orally, or topically and orally. In certain specific embodiments, wherein any of the compositions described above and herein comprises a lactoferrin, the composition is administered orally. In another specific embodiment, wherein any of the compositions described above and herein comprises a lactoferrin, the composition is administered topically, or orally, or topically and orally. In particular embodiments, the methods described above and herein further comprise orally administering a second physiologically acceptable composition, wherein the second composition comprises a lactoferrin.

In another embodiment, a method is provided for treating a mucosal disorder in a subject who is receiving or who will receive chemotherapy or radiation therapy for treatment of a malignancy (i.e., cancer), said method comprising administering to the subject a therapeutically effective amount of a physiologically acceptable composition that comprises a mineral salt and a sulfonic acid. In certain specific embodiments, the mineral salt is zinc gluconate and the sulfonic acid is taurine. In other embodiments, these methods comprise administering in certain embodiments, the mineral salt comprised within the composition comprises (a) a mineral moiety selected from zinc, calcium, iron, copper, magnesium, manganese, cobalt, chromium, selenium, and vanadium and (b) a salt moiety selected from gluconate, acetate, ascorbate, and sulfate. In a more specific embodiment, the mineral salt is zinc gluconate, and the composition comprises from 0.2% (w/w) to 5.5% (w/w) zinc gluconate. In other specific embodiments, the mineral salt is zinc gluconate, and the composition comprises from between 0.25% (w/w) to 5.5% (w/w) zinc gluconate. Further with respect to the methods described above and herein, in certain embodiments, the sulfonic acid comprised within the composition is taurine and the composition comprises from between 0.25% (w/w) to 30% (w/w) taurine. In certain embodiments, the composition comprises from between 0.25% (w/w) to 5.5% (w/w) zinc gluconate and comprises from between 0.25% (w/w) to 30% (w/w) taurine. In more specific embodiments, the sulfonic acid is taurine and the composition comprises from between 0.5% (w/w) and 4.0% (w/w) taurine. In another more specific embodiment, wherein the sulfonic acid is taurine, the composition comprises from between 0.5% (w/w) and 8.0% (w/w) taurine. In still other specific embodiments, the composition comprises from between 0.25% (w/w) to 5.5% (w/w) zinc gluconate and from between 0.5% (w/w) and 8.0% (w/w) taurine. In other embodiments, the composition further comprises one or more of a flavoring agent, a mucoadhesive agent, a pH adjusting agent, a solubilizing agent, a viscosity modulating agent, and a stabilizing agent. In a more particular embodiment the compositions described above and herein further comprise one or more of from between 0.05% to 3.0% (w/w) glycyrrhetinic acid; from between 0.04% to 15% (w/w) polyvinylpyrrolidone (PVP); from between 0.01% to 5.0% (w/w) hyaluronic acid; and from between 0.05% to 5.0% (w/w) glycerin. In another embodiment, the composition comprises from between 0.25-5.5% (w/w) zinc gluconate; from between 0.5%-8% (w/w) taurine; and from between 0.04%-15% (w/w) PVP. In another specific embodiment, the compositions comprise (a) 0.5% (w/w) zinc gluconate, 1.0% (w/w) taurine, and 4.0% PVP (w/w); (b) 0.5% (w/w) zinc gluconate, 1.0% (w/w) taurine, and 8.0% PVP (w/w); or (c) 2.0% (w/w) zinc gluconate, 4.0% (w/w) taurine, and 4.0% PVP (w/w). In other specific embodiments, the composition comprises 0.5% (w/w) zinc gluconate and 1.0% (w/w) taurine. In still another specific embodiment, the composition comprises 2.5% (w/w) zinc gluconate and 5.0% (w/w) taurine. In other specific embodiments, the pH of the composition is adjusted to between 3.5 and 4.5 or is adjusted to between 5.5 and 7.5. In still other particular embodiments, these compositions further comprise a lactoferrin.

Also provided herein is a composition comprising 0.5%-2% (w/w) zinc gluconate; 0.5%-4% (w/w) taurine; and at least one of (a) 0.5%-2.5% (w/w) glycyrrhetinic acid; (b) 0.25%-10% (w/w) polyvinylpyrrolidone (PVP); (c) 0.05%-0.25% (w/w) hyaluronic acid; and (d) 0.05%-0.25% (w/w) glycerin. In certain embodiments, the composition comprises 0.5%-2% (w/w) zinc gluconate; 0.5%-4% (w/w) taurine; and 4-8% (w/w) PVP. In other specific embodiments, the composition comprises 0.5% (w/w) zinc gluconate, 1.0% (w/w) taurine, 1.0% (w/w) glycyrrhetinic acid, 8.0% (w/w) PVP, 0.1% (w/w) hyaluronic acid, and 0.1% (w/w) glycerin. In still another embodiment, the composition comprises 0.5% (w/w) zinc gluconate, 1.0% (w/w) taurine, 1.0% (w/w) glycyrrhetinic acid, 8.0% (w/w) PVP, 0.1% (w/w) hyaluronic acid, and 0.1% (w/w) glycerin. In other specific embodiments, the pH of the composition is adjusted to between 3.5 and 4.5 or is adjusted to between 5.5 and 7.5. In yet another embodiment, the composition further comprises a lactoferrin.

Also provided herein, is a method for supplementing a mineral deficiency in a subject, said method comprising administering a composition comprising a mineral salt, a sulfonic acid, and one or more of 0.05% to 3.0% (w/w) glycyrrhetinic acid; 0.04% to 15% (w/w) polyvinylpyrrolidone (PVP); 0.01% to 5.0% (w/w) hyaluronic acid; and 0.05% to 5.0% (w/w) glycerin. In particular embodiments of this method, the mineral salt comprises (a) a mineral moiety selected from zinc, calcium, iron, copper, magnesium, manganese, cobalt, chromium, selenium, and vanadium and (b) a salt moiety selected from gluconate, acetate, ascorbate, and sulfate. In a more specific embodiment, the mineral moiety is zinc and the salt moiety is gluconate. In still other specific embodiments, the sulfonic acid is taurine. In yet another embodiment, the method for supplementing a mineral deficiency in a subject comprises administering a composition comprising from between 0.25% (w/w) to 5.5% (w/w) zinc gluconate and from between 0.25% (w/w) to 30% (w/w) taurine. In still another embodiment, the method for supplementing a mineral deficiency in a subject comprises administering a composition comprising from between 0.25% (w/w) to 5.5% (w/w) zinc gluconate and from between 0.5% (w/w) to 8% (w/w) taurine.

In another embodiment, a method is provided for inhibiting disruption of intercellular junctions between adjacent cells, comprising contacting the cells with a composition comprising a physiologically acceptable composition that comprises a mineral salt and a sulfonic acid. In certain embodiments, the cells are epithelial cells, and in other certain embodiments, the cells are endothelial cells. In still another embodiment, the cells are present in a subject who has or who is at risk for developing a mucosal disorder or a dermal disorder. In a more specific embodiment, the mucosal disorder comprises mucositis. In particular embodiments, the mucosal disorder is selected from oral stomatitis, oral mucositis, an oral ulceration, Crohn's disease, periodontitis, interstitial cystitis, and a wound; vaginal dryness, vaginal burning, vaginal ulceration, dyspareunia, leukorrhea, vulvar pruritus, vulvar burning, and atrophic vaginitis; a mucosal disorder that is consequent to any one or more of hormone insufficiency, bone marrow transplant, chemotherapy, radiation therapy, viral infection, fungal infection, and bacterial infection; and a mucosal disorder that is consequent to one or both of chemotherapy and radiation therapy administered to the subject for treatment of a head and neck tumor, a leukemia, breast cancer, prostate cancer, pancreatic cancer, ovarian cancer, melanoma, liver cancer, lung cancer, urinary cancer, colon cancer, or HIV/AIDS. In yet another specific embodiment, the dermal disorder comprises diaper rash, skin dryness, dermatitis, eczema, psoriasis, erythema, acne, xerosis, or radical oxygen species-induced skin damage. In particular embodiments, the mineral salt comprises (a) a mineral moiety selected from zinc, calcium, iron, copper, magnesium, manganese, cobalt, chromium, selenium, and vanadium and (b) a salt moiety selected from gluconate, acetate, ascorbate, and sulfate. In more specific embodiments, the mineral salt is zinc gluconate, and the composition comprises from between 0.25% (w/w) to 5.5% (w/w) zinc gluconate. In another specific embodiment, the sulfonic acid is taurine and the composition comprises from between 0.25% (w/w) to 30% (w/w) taurine. In yet other embodiments, the mineral salt is zinc gluconate, and the composition comprises from between 0.25% (w/w) to 5.5% (w/w) zinc gluconate, and the sulfonic acid is taurine and the composition comprises from between 0.25% (w/w) to 30% (w/w) taurine. In other particular embodiments, the sulfonic acid comprised in the composition is from between 0.5% (w/w) and 8.0% (w/w) taurine. In yet other embodiments, the mineral salt is zinc gluconate, and the composition comprises from between 0.2% (w/w) to 5.5% (w/w) zinc gluconate. In still another embodiment, the composition comprises from between 0.25% (w/w) to 5.5% (w/w) zinc gluconate and between 0.5% (w/w) and 8.0% (w/w) taurine. In yet other certain embodiments, the composition further comprises a lactoferrin. In still other particular embodiments, the pH of the composition is between 3.0 and 8.5; in more specific embodiments, the pH is between 3.5 and 4.5; and yet in still more specific embodiments, the pH is between 5.5 and 7.5.

Also provided herein is a use for a composition comprising a mineral salt and a sulfonic acid for the manufacture of a medicament for treating and/or preventing a mucosal disorder, disease, or condition or a dermal disorder, disease, or condition. In other embodiments, a physiologically acceptable composition comprising a mineral salt and a sulfonic acid for use in treating and/or preventing a mucosal disorder, disease, or condition or a dermal disorder, disease, or condition is provided. The compositions, mucosal and dermal diseases and disorders and conditions and other embodiments are described in detail above and herein.

As used herein and in the appended claims, the singular forms "a," "and," and "the" include plural referents unless the context clearly dictates otherwise. Thus, for example, reference to "a compound" or "a composition" includes a plurality of such compounds or compositions, respectively. Similarly, reference to "a cell" or "the cell" includes reference to one or more cells and equivalent terms (e.g., plurality of cells) known to those skilled in the art, and so forth. Use of the conjunction "or" is meant to illustrate choice or possibilities and unless stated otherwise, the use of "or" does not mean that the terms or phrases joined by the conjunction are alternatives that are exclusive of each other. When referring to a number or a numerical range means that the number or numerical range referred to is an approximation within experimental variability (or within statistical experimental error), and thus the number or numerical range may vary between 1% and 20% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

As used herein, any concentration range, percentage range, ratio range, or integer range is understood to include the value of any integer within the recited range and, when appropriate, fractions thereof (such as one tenth and one hundredth of an integer), unless otherwise indicated. Also, any number range recited herein relating to any physical feature, such as polymer subunits, size, thickness, height, weight, mass, volume, molarity, or pH are to be understood to include any integer or fraction thereof within the recited range, unless otherwise indicated.

DETAILED DESCRIPTION

Figure 1:
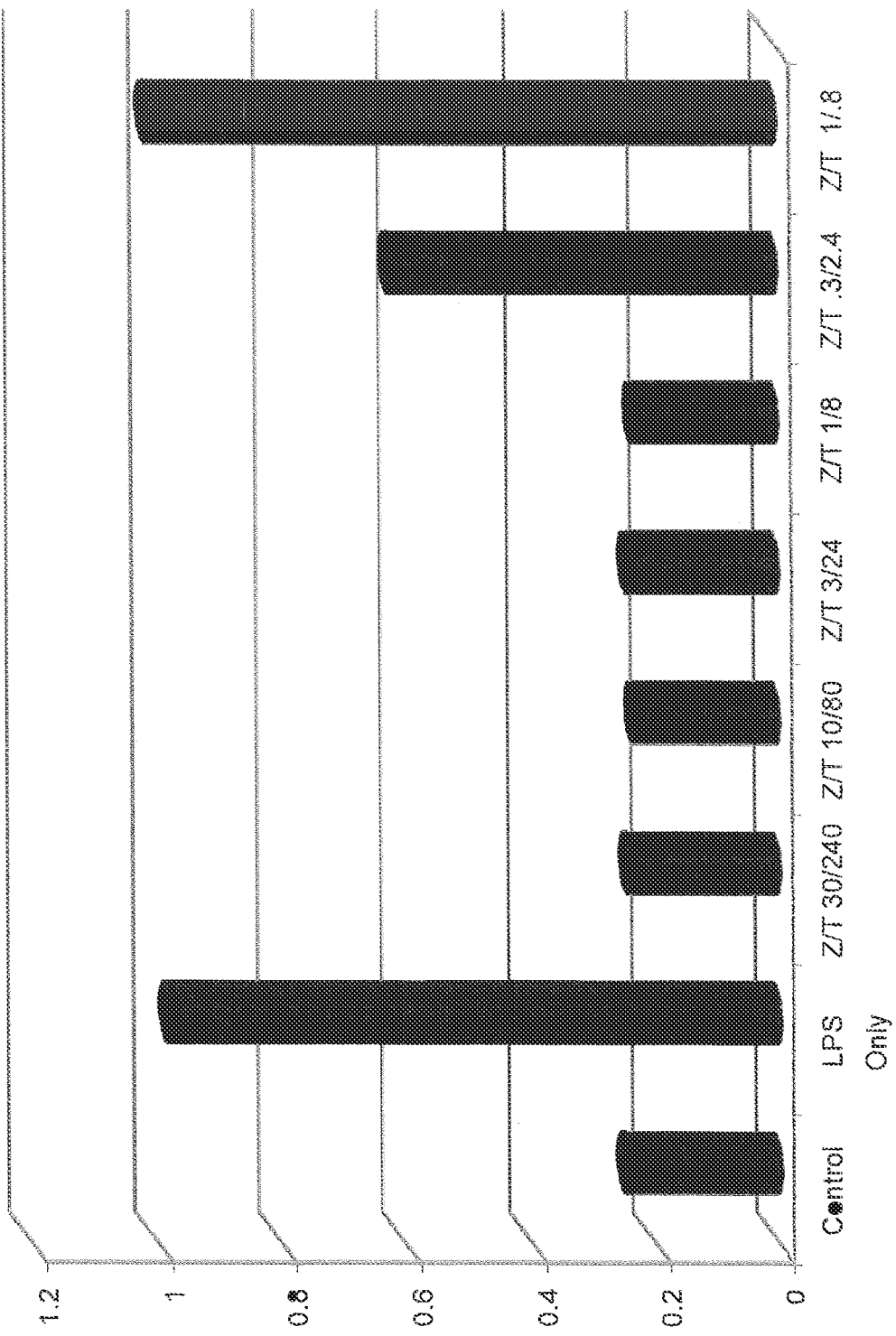
FIG. 1 illustrates the effect of zinc (Z) and taurine (T) to reduce production of the proinflammatory cytokine IL-6 in lipopolysaccharide (LPS)-stimulated CaCo2 cells. The concentrations for each of zinc gluconate and taurine (Z/T) are indicated in mM on the x-axis.

The methods described herein relate generally to treatment of mucosal and dermal diseases, disorders, and conditions using compositions comprising a mineral salt (e.g., a zinc salt, for example, zinc gluconate) and a sulfonic acid (e.g., taurine). These methods provide benefit, at least in part, by inhibiting disruption of intercellular junctions between adjacent and neighboring cells, which also inhibits disruption of membrane barrier integrity and function of the cells, thus reducing undesired membrane barrier permeability.

A composition (GelX® Oral Gel. BMG Pharma, Gardnerville, N.V.) has been approved by the U.S. Food and Drug Administration for use as a mechanical device for management of pain and for relief of pain by its adherence to the mucosal surface of the mouth. Polyvinyl pyrrolidone (PVP) is included in GelX® Oral Gel as the main active ingredient of the device because it forms a protective film over the mucosal surface. Two other ingredients included in GelX® Oral Gel are a zinc salt and taurine, which were added as preservatives and which were less toxic than other commonly used preservatives.

A small clinical study was initiated in which patients with cancer (i.e., a malignancy) who had radiation-induced mucositis as a consequence of radiotherapy were treated with compositions comprising PVP, a zinc salt (zinc gluconate), and taurine. The expected results after such treatment were that a palliative benefit would be observed in which the stinging, burning, and general pain associated with mucositis would be temporarily reduced, and that over the course of typically several weeks of therapy, chemical irritation would be reduced and a slightly improved rate of healing might occur, even as ulceration from the underlying cause of radiation therapy continued to develop. In addition to the immediate palliative benefits anticipated, the following were observed: an abrupt reduction in the severity of ulceration; a reduction of the primary symptoms of ulceration; and improvement in secondary markers of mucositis including, a reduction of xerostomia (dryness due to lack of saliva), and a return of the ability to taste.

Treatment of dermal conditions using compositions comprising a zinc salt (zinc gluconate), and taurine also provided therapeutic benefit beyond palliative relief. By way of example, as described herein, application of an exemplary composition comprising zinc gluconate and taurine halted development of edema, redness, and reduced pain related to a second degree burn.

Consistent with these human in vivo observations was that the combination of a mineral salt and a sulfonic acid (for example, zinc gluconate and taurine, respectively) inhibited production of pro-inflammatory cytokines (e.g., IL-6 and IL-8) in a cell culture model used for assessing epithelial cell tight junction structure and function (see Example 3). Additional analysis with respect to inhibition of production of the pro-inflammatory cytokine, IL-8, indicated that the effect of zinc and taurine in combination was synergistic compared with each of zinc and taurine alone. As presently understood in the art, IL-8 production is a prognosticator of intercellular junction damage. The cell culture model studies in conjunction with the in vivo observations indicates that therapeutic benefit relates, at least in part, to the capability of the combined mineral salt and sulfonic acid to prevent, inhibit, and/or reduce, disruption of intercellular junctions that affects the structural and functional integrity of the cells.

While zinc deficiency has been associated in vivo with inflammatory bowel disease and *Helicobacter pylori*-induced gastric mucosa inflammation (see, e.g., Sturniolo et al., *Inflamm. Bowel Dis.* 7:94-98 (2001); Sempertegui et al., *Heliobacter* 12:43-48 (2007); Finamore et al., *J. Nutr.* 138:1664-70 (2008)), and in vitro induces membrane barrier damage in a Caco-2 cell model (see, e.g., Finamore et al., supra), the suggested treatment of patients with these disorders has been to increase zinc intake by dietary improvement and zinc supplementation (e.g., with zinc sulfate) to provide improvement in chronic conditions over the long-term (see, e.g., Finamore et al., supra). By contrast as described herein, by combining a mineral salt, such as a zinc mineral salt, with a sulfonic acid such as taurine, the mineral salt is effectively trafficked (i.e., delivered) to the affected cells and tissue. In addition, because taurine is capable of penetrating skin (see, e.g., da Silva et al., *Pharmaceut. Res.* 25:1846-1850 (2008)), a mineral salt, such as zinc, may be delivered to damaged dermal tissue when combined with taurine, thus providing zinc to cells and tissue that zinc not in combination with taurine would not otherwise have contact. Without wishing to be bound by theory, the sulfonic acid taurine, which can act as an anti-oxidant and which also inhibits cytokine production, also contributes to the effectiveness of the compositions described herein in healing and restoration of cellular integrity of affected tissue.

As described herein, an exemplary composition comprising a zinc salt and taurine in combination have anti-inflammatory activity and are capable of inhibiting production of anti-inflammatory cytokines (such as, by way of nonlimiting example, IL-6 and IL-8) in cells. Accordingly, as described in greater detail herein, methods are provided for treating and/or preventing inflammation associated with mucosal diseases, disorders, and conditions and dermal diseases, disorders, and conditions described in greater detail herein.

Methods are provided herein for treating and/or preventing dermal diseases, disorders, and conditions, and for treating and/or preventing mucosal diseases, disorders, and conditions, including inflammatory dermal and mucosal diseases, disorders, and conditions. These methods comprise administering compositions comprising at least one mineral salt and at least one sulfonic acid.

Mucosal diseases, condition, and disorders that are treatable by the methods and compositions described herein include, but are not limited to, mucositis (e.g., oral mucositis), which is an inflammation of a mucous membrane and may also include ulceration of the mucous membrane. In other embodiments, methods and compositions are provided herein for treating atrophic vaginitis (AV) and for treating conditions (e.g., vaginal dryness) that may precede or are associated with atrophic vaginitis. Additional dermal diseases, disorders, and conditions and mucosal diseases, disorders, and conditions that may be treatable with the compositions described herein include, but are not limited to, vaginal ulcerations (including micro-lesions); dermal conditions and mucosal conditions that are side effects (i.e., adverse effects) of radiation therapy and/or chemotherapy (e.g., oral mucositis) (i.e., radiation therapy or chemotherapy induced mucositis); viral infections such as shingles and herpes simplex, HIV/AIDS; and chronic skin disorders such as eczema, psoriasis, and dermatitis. Dermal and mucosal diseases, conditions, and disorders treatable using the compositions and methods described herein are discussed in greater detail below.

In one embodiment, compositions (pharmaceutically and physiologically acceptable) are provided herein, and methods of using the compositions, for treating dermal disorders or mucosal disorders, which occur as side effects of radiation therapy and/or chemotherapy. Dermal or mucosal disorders occur in subjects who are receiving radiation therapy and/or chemotherapy, including those who receive treatment of head and neck tumors, and also occur in about 90% of children with leukemia. These side effects include oral mucositis (including micro-lesions) and oral stomatitis. Side effects (also called adverse effects) may also result in a mucosal disorder of any one or more mucosa including oral mucosa, intestinal mucosa, rectal mucosa, and the like consequent to chemotherapy or radiotherapy treatment of any one or more of a wide variety of solid or non-solid cancers or lymphomas (for example, breast, prostate, pancreatic, ovarian, liver, lung, urinary, and colon cancer, Kaposi's sarcoma, and melanoma).

The compositions and methods described herein may also be used for preventing or treating a mucosal disorder, including but not limited to, atrophic vaginitis, vaginal micro-lesions, inflammatory bowel disease (including Crohn's disease and ulcerative colitis), periodontitis, interstitial cystitis, wound healing, an inflammatory condition, dyspareunia, burning, leucorrhea, xerosis (i.e., dry skin, atopic dermatitis), vaginal dryness, vulvar pruritus, vaginal pruritus, vulvar burning, vaginal burning, vulvar dystrophy, vaginal malodor, candidiasis, trichomoniasis, or bacterial vaginosis; and urinary disorders such as dysuria, hematuria, frequency, stress incontinence, and tract infection; complications resulting from antiestrogen medications including menopausal sexual dysfunction, among other symptoms; viral infections including shingles, herpes simplex. HIV/AIDS; and chronic skin disorders such as eczema, psoriasis and dermatitis; irritation due to oral surgery, aging, traumatic ulcers caused by braces or ill fitting dentures, diffuse aphthous ulcers, or medication, or disease; and other dermal disorders, diseases, and conditions described herein.

In a certain embodiment, the methods described herein, which comprise administering a composition comprising a mineral salt and a sulfonic acid, are used for treating or preventing (i.e., reducing or decreasing the likelihood of occurrence in a statistically, biologically, or clinically significant manner) inflammation or an inflammatory response that is associated with a mucosal or dermal disease, disorder or condition. In one embodiment, the methods described herein may reduce inflammation of a mucosa or dermis, thereby treating conditions such as oral mucositis and AV. In other embodiments, the methods provided herein may reduce the likelihood of occurrence of inflammation of the dermis or of a mucous membrane by administering the mineral salt and sulfonic acid to a subject at risk of developing an inflammation of a mucous membrane or dermis (by way of nonlimiting example, a subject who has vaginal dryness or who is beginning radiotherapy and/or chemotherapy for treatment of a cancer or malignancy).

Also provided herein are physiologically acceptable (i.e., physiologically suitable and pharmaceutically suitable and acceptable) compositions that may be administered to a subject for treating or preventing inflammation associated with a dermal or mucosal disease, disorder, or condition. These compositions comprise at least one mineral salt and at least one sulfonic acid. In particular embodiments, the compositions comprise therapeutically effective concentrations of a mineral salt of zinc and a sulfonic acid. In more particular embodiments, the mineral salt is zinc gluconate and the sulfonic acid is taurine. In certain embodiments, the compositions further comprise a lactoferrin.

Compositions described herein may be administered in forms and in a manner, described in greater detail herein and understood in the art, to deliver the composition and the active ingredients thereof in an amount sufficient to produce a therapeutic benefit. In certain embodiments, one or more of these compositions may be administered topically; in other embodiments one or more of the compositions is delivered orally; in yet other embodiments, one or more of the compositions is administered topically and orally. The compositions are therefore formulated to be physiologically acceptable (i.e., pharmaceutically suitable or acceptable) for administration to a subject, including a human subject. These compositions comprise a mineral salt (e.g., a zinc salt, for example, zinc gluconate) formulated with a sulfonic acid (e.g., taurine) and may be administered to prevent and treat dermal or mucosal disorders, diseases, and conditions, including but not limited to mucositis (including oral mucositis and oral stomatitis) or atrophic vaginitis. As used herein, the term atrophic vaginitis is interchangeable with the terms, urogenital atrophy and vaginal atrophy. Mucositis is an inflammation of a mucous membrane, which is a painful disorder involving a mucous membrane located at one or more of an oral cavity, gastrointestinal tract, bladder, esophagus, vagina, rectum, lung, a mucosal surface of a nasal cavity, ear, or ocular mucosa.

In certain embodiments, a composition comprising a mineral salt (e.g., a zinc salt, for example, zinc gluconate) and a sulfonic acid (e.g., taurine) may further comprise a lactoferrin (or variant or fragment thereof). Such a composition may be administered locally (e.g., topically to a mucosal surface, for example, oral or vaginal mucosa) and/or orally. In other embodiments, methods are provided herein that comprise administering a physiologically acceptable composition (a first composition) comprising a mineral salt and a sulfonic acid, which composition may, but not necessarily, also comprise a lactoferrin, which first composition is administered sequentially (either prior to or after) or concurrently with administration of a separate (or second) physiologically acceptable composition comprising a lactoferrin and one or more physiologically acceptable carriers (excipients) but which lacks a mineral salt and a sulfonic acid. In particular embodiments, the composition comprising the lactoferrin and lacking a mineral salt and a sulfonic acid is administered orally.

As described in greater detail herein, methods for treating mucositis, (including oral mucositis and oral stomatitis), atrophic vaginitis, vaginal dryness, and other mucosal conditions and disorders described herein may decrease inflammation; promote restoration and healing of the mucous membrane including minimizing, preventing, and inhibiting ulceration; and/or slow, inhibit, or prevent further loss of mucous membrane integrity. By minimizing, preventing, or reducing ulceration, the compositions provide the added benefit of reducing the susceptibility of the mucous membrane to invasion and colonization by microorganisms, thus decreasing the likelihood of microbial infection and/or decreasing the recurrence and frequency of microbial infections. Moreover, compositions comprising a sulfonic acid and a mineral salt, such as taurine and zinc gluconate, respectively, have antimicrobial activity.

In other embodiments of the methods described above and herein for treating or preventing a dermal disease, disorder, or condition or a mucosal, disease, disorder or condition, the methods further comprise identifying a subject who is need of receiving a composition comprising a mineral salt (e.g., a zinc salt, for example, zinc gluconate) and a sulfonic acid (e.g., taurine). As described in greater detail herein, the subject may have mucositis (e.g., oral mucositis or oral stomatitis) or may be at risk of developing mucositis (for example, a patient who is receiving or who is about to receive chemotherapy and/or radiation therapy). By way of additional example, a subject in need may be a female subject who has AV or who is at risk of developing AV (e.g., a woman who presents symptoms that may precede clinical manifestation of AV, such as vaginal dryness).

In another embodiment, methods are provided for inhibiting (i.e., reducing, abrogating, or decreasing, or reducing the likelihood of occurrence of) disruption of intercellular junctions between adjacent (i.e., neighboring) cells, which methods comprise contacting the cells with a physiologically acceptable composition comprising a mineral salt (e.g., a zinc salt, for example, zinc gluconate) and a sulfonic acid (e.g., taurine). The step of contacting, in some manner, permits or enables interaction between the cells and the composition. Such methods maintain or restore the structure and function of the membrane barrier, which in turn, maintains or restores membrane barrier permeability, which in the absence of cellular contact with the composition would result in loss of intercellular junction integrity and function, increasing permeability of the cells. The methods thus inhibit, reduce, prevent, and/or maintain membrane barrier integrity of a cell.

Intercellular junctions refer to intercellular junctional complexes that are formed between adjacent cells. Intercellular junctions include tight junctions (TJ) and adherens junctions (AJ) that form circumferential zones of contact between adjacent cells. Disruption refers to loss, destruction, or other undesired or deleterious effect to structural and/or functional integrity of the intercellular junctions. The methods provided herein may inhibit, reduce, prevent loss of structural and/or functional integrity of the intercellular junctions in a statistically significant, clinically significant, or biologically significant manner. Disruption may adversely affect the structure and/or function of one or more membrane or cytoskeletal proteins and disrupt their respective interactions that help maintain the structure integrity and function of the intercellular junction. These methods thereby inhibit, prevent, or reduce loss of integrity (functional and/or structural) of the TJ and/or AJ. In certain embodiments, the cells are endothelial cells, and in other particular embodiments, the cells are epithelial cells. Endothelial and epithelial cells include, by way of non-limiting example, gastrointestinal, oropharyngeal, bladder, esophageal, vaginal, rectal, pulmonary, nasal, ear, or ocular endothelial or epithelial cells, respectively.

In certain embodiments, the cells (i.e., epithelial or endothelial cells) comprise tissue in a subject. In particular embodiments, the subject has or is at risk of developing a dermal disease, disorder, or condition or has or is at risk of developing a mucosal disease, disorder, or condition. As described in detail herein, mucosal and dermal disorders include mucositis (e.g., oral mucositis, oral stomatitis, AV). Mucosal and dermal disorders also include, for example, the dermal or mucosal disorders that occur as side effects of radiation therapy and/or chemotherapy associated with the radioactive and/or chemotherapeutic treatment of cancers (i.e., malignancies), including, head and neck tumors and leukemia. Such side effects include oral mucositis (including micro-lesions) and oral stomatitis. Dermal or mucosal disorders may also occur as side effects of radiation therapy and/or chemotherapy of other cancers, including, any one or more of a wide variety of solid or non-solid cancers or lymphomas (for example breast, prostate, pancreatic, ovarian, melanoma, liver, lung, urinary, salivary gland, and colon cancers; Kaposi's sarcoma), which may affect any one or more mucosa including oral mucosa, intestinal mucosa, rectal mucosa, and the like. Mucosal disorders also include atrophic vaginitis, vaginal micro-lesions, inflammatory bowel disease (including Crohn's disease and ulcerative colitis), eczema, psoriasis, periodontitis, interstitial cystitis, wound healing, or an inflammatory condition, dyspareunia, burning, leucorrhea, xerosis, vaginal dryness, vulvar pruritus, vaginal pruritus, vulvar burning, vaginal burning, vulvar dystrophy, vaginal malodor, candidiasis, trichomoniasis or bacterial vaginosis, and urinary disorders such as dysuria, hematuria, frequency, stress incontinence and tract infection, among other symptoms, including menopausal sexual dysfunction, complications resulting from antiestrogen medications, viral infections including shingles, herpes simplex, HIV/AIDS; and chronic skin disorders such as eczema, psoriasis and dermatitis, irritation due to oral surgery, aging and traumatic ulcers caused by braces or ill fitting dentures, diffuse aphthous ulcers, medication, or disease.

In another embodiment, the methods for inhibiting (i.e., reducing, abrogating, or decreasing, or reducing the likelihood of occurrence of) disruption of intercellular junctions between adjacent (i.e., neighboring) cells may comprise contacting cells with a mineral salt and taurine (mixing, combining, or in some manner permitting interaction) in vitro. Such methods may thus be useful as in vitro assays for monitoring pharmacokinetics of a mineral salt and sulfonic acid during pre-clinical, clinical, and post-marketing studies; evaluating (including quality control and quality assurance) biological activity of compositions comprising a mineral salt and sulfonic acid; evaluating, measuring, and/or monitoring the biological effect of other agents that may be included in a composition comprising a mineral salt and sulfonic acid; among others.

As noted above, the cells may be endothelial cells or the cells may be epithelial cells. For in vitro assays, the cells may be present in a biological sample. Such a biological sample may be a biopsy specimen, a body fluid (e.g., lung lavage, ascites, mucosal washings, synovial fluid) that contains the endothelial and/or epithelial cells, bone marrow, lymph nodes, tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. In certain embodiments, the subject or biological source may be a human or non-human animal, a primary cell culture (e.g., immune cells, virus infected cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like. Cell lines that may be used in the in vitro methods include cultured monolayers of polarized epithelial cell lines, such as MDCK. T84, and Caco-2, which provide model systems for the study of tight junction structure and function (see, e.g., Clayburgh et al., BioRad Protocol Guide, BioRad 2008; Clayburgh et al., *J. Biol. Chem.* 279:55506-13 (2004)).

The in vitro methods described herein may be performed by using techniques such as propagation of cells (i.e., cell culture) and detection methods all of which are routinely practiced in the art and with which the skilled person will be familiar. Conditions for a particular assay include temperature, buffers (including salts, cations, media), and other components that maintain the integrity of the mineral salt, the sulfonic acid, and cells, with which a person skilled in the art will be familiar and/or which can be readily determined. Persons skilled in the art are also familiar with assay design such that appropriate controls will be performed to enable determination of the capability of the composition (and its components) to inhibit disruption of intercellular junctions. The mineral salt and/or sulfonic acid may be contacted (mixed, combined with, or in some manner permitted to interaction) with the cells, under conditions and for a time sufficient to permit interaction between the component or components of the composition.

Appropriate conditions for permitting interaction of the reaction components according to this method and other methods described herein include, for example, appropriate concentrations of reagents and components (including a sulfonic acid and mineral salt), temperature, and buffers with which a skilled person will be familiar. Concentrations of reaction components, buffers, temperature, and time period sufficient to permit interaction of the reaction components can be determined and/or adjusted according to methods described herein and with which persons skilled in the art are familiar. To practice the methods described herein, a person skilled in the art will also readily appreciate and understand which controls are appropriately included when practicing these methods.

In addition to the methods and techniques described above and herein, which include determination of cytokine production/inhibition in epithelial and endothelial cells, additional assays may be performed to determine the effect and capability of the compositions described herein to inhibit disruption and/or destruction of intercellular junctions (i.e., inhibit, reduce, prevent loss of structural and/or functional integrity of the intercellular junctions in a statistically significant, clinically significant, or biologically significant manner). Such assays include membrane permeability assays (see, e.g., Ferruzza et al., *Toxicol. In Vitro* 16:399-404 (2002)); neutrophil transmigration assays (see, e.g., Finamore, supra; Roselli et al., *Br. J. Nutr.* 95:1177-84 (2006)); immunolocalization of junction proteins (see, e.g., Ara et al., *Cell Commun. Adhes.* 11:13-23 (2004)).

In other embodiments, methods are provided for administering a bioactive mineral to a subject who has a mineral insufficiency or who would otherwise benefit from the therapeutic effect(s) of being treated with a composition comprising the mineral. The compositions described herein may also be formulated for use in cosmetics.

Mineral Salts

The compositions described herein for use in the methods described herein comprise at least one mineral salt. The mineral moiety of a mineral salt may be any mineral that is an inorganic element that is essential in some amount to normal biological function of a human (e.g., zinc, calcium, magnesium, manganese, cobalt, chromium, selenium, vanadium, copper, iron, nickel, silicon, boron, arsenic, molybdenum, sodium, potassium, phosphorus, sulfur, chlorine, fluorine, iodine, and lithium). In certain embodiments, the mineral moiety of a mineral salt may be zinc, calcium, magnesium, manganese, cobalt, chromium, selenium, vanadium, copper, iron. In particular embodiments, the mineral moiety of the mineral salt is zinc. The salt moiety of the mineral salt may be any suitable inorganic or organic acid, including but not limited to, gluconate, acetate, ascorbate, and sulfate. In particular embodiments, the salt moiety is gluconate. In a specific embodiment, the mineral salt is zinc gluconate wherein the mineral moiety is zinc and the salt moiety is gluconate.

In certain embodiments, the compositions comprise a sufficient concentration of a mineral salt of zinc (e.g., zinc gluconate) to treat effectively a dermal or mucosal disorder and yet are intended to comprise zinc at a concentration that is less irritating than other zinc-containing compositions. The compositions described herein may be formulated to increase the bioavailability of a mineral salt, such as zinc, thereby reducing the amount of the mineral salt required to treat a mucosal or dermal disorder and/or to reduce or prevent inflammation associated with the mucosal or dermal disorder. Reduction of the concentration and amount of one or more active ingredients in a composition used for treating a disease or disorder may minimize toxic effects and thus increase patient compliance, reduce unwanted complications associated with higher amounts of one or more active ingredients, and/or reduce the cost of manufacturing.

In certain embodiments, the composition may contain a sulfonic acid (e.g., taurine) that is in the form of a mineral salt of zinc, calcium, magnesium or manganese. By way of example, the sulfonic acid taurine may be prepared or be in the form of a taurate salt, having the general formula $H_2N-CH_2-CH_2-SO_3)_2X^{2+}$, wherein X may be zinc, magnesium, calcium, or manganese. In certain embodiments, the physiologically acceptable composition may comprise a zinc taurate salt, a calcium taurate salt, or a magnesium taurate salt, which may be used in the methods described herein for treating a dermal or mucosal disease, disorder, or condition.

Because metals are highly charged molecules, many minerals are not absorbed well by tissues and are not readily transported, actively or passively, into cells, even if available in the serum. Some minerals are also unpleasant for a subject to consume or apply. For example, zinc supplements taken orally can produce nausea, vomiting, and diarrhea; zinc compounds applied topically are astringent and can cause irritation and burns. Even though zinc oxide is neutral and can be applied topically, it is not readily absorbed into the tissue. Water soluble zinc salts such as zinc acetate, zinc chloride, and zinc sulfate are highly acidic and cannot be neutralized with sodium bicarbonate, sodium hydroxide or the like to provide a physiologically suitable composition that can be administered to a subject. For example, to neutralize these water soluble zinc salts with sodium bicarbonate requires as much as a molar ratio of 5 to 1 to obtain a solution at pH 7, yielding a composition that has undesirable elevated sodium content. When sodium hydroxide is used to neutralize these water soluble zinc salts, the neutralized composition readily precipitates on standing.

As described herein, methods for treating dermal and mucosal disorders comprise administering a composition comprising a mineral salt, which in certain embodiments is a zinc salt, such as zinc gluconate. Zinc is essential for the function of at least 70 enzymes and is involved in a variety of metabolic processes, including tissue growth and repair. Even though zinc salts have been administered to subjects for treatment of various diseases and disorders, many of the zinc salts used to date have undesired effects.

Zinc salts have been used to inhibit bacterial and viral growth in subjects who are infected or who are at risk of becoming infected. Ophthalmic preparations of zinc sulfate to treat herpetic keratitis have been recommended since 1943. Zinc oxide, zinc sulfate, and zinc chloride have each been used in treating chronic and acute wounds. Oral preparations of zinc citrate have been used for treating gingivitis and periodontitis to reduce plaque formation and to inhibit bacterial growth. Oral preparations of several different zinc salts have been marketed for reducing the symptoms and duration of the common cold caused by rhinovirus; however, the preparations are unpalatable and cause mouth irritation and nausea. A more palatable and less irritating formulation has been developed that contains a zinc salt and an amino acid (see, e.g., U.S. Pat. No. 4,229,430).

In addition, topical application of certain available zinc solutions can cause painful or irritating side effects unless zinc is present in very low concentrations, which may be insufficient to effectively treat the disorder or condition intended to be treated. Zinc sulfate solutions of 0.2-1% can cause severe irritation, unpleasant dryness and stimulate the emetic reflex when applied circumorally. Reports of dermal irritancy in animal dermal abrasion models that are used for studying wound healing show the following: 1% aqueous zinc chloride is a severe irritant; 20% aqueous zinc acetate is a slightly less irritant; 20% suspension zinc oxide, 1% aqueous zinc sulfate, and 20% suspension zinc pyrithione, are not overtly irritant. The less irritant zinc salts, such as zinc oxide, which is only slightly soluble in water, were only marginally effective in stimulating epidermal healing in comparison to the more irritating and more water-soluble zinc salts (see, e.g., U.S. Pat. No. 6,558,710).

Previously described compositions comprising zinc salts, such as zinc gluconate and zinc ascorbate, comprise at least one amino acid that is formulated with the zinc salt to improve solubility at neutral pH (see, e.g., U.S. Pat. Nos. 4,711,780 and 4,937,234). The amino acids used in the compositions were typically either a sulfur containing amino acid (e.g., cysteine) or a basic amino acid (e.g., lysine, arginine, or histidine). However, in certain circumstances when lysine is, for example, used for treating a subject vaginally, the amino acid lysine may be decarboxylated by vaginal bacteria to produce the diamine cadaverine, a toxic foul smelling molecule similar to putrescine, both of which are produced by the breakdown of amino acids in living and dead organisms and both can be toxic. Cadaverine and putrescine are largely responsible for the foul odor of putrefying flesh and also contribute to the odor of processes related to bad breath (i.e., halitosis) and bacterial vaginosis. Use of other amino acids may also produce toxic metabolites or malodors (including tryptophan to tryptamine, phenylalanine to phenylethylamine, tyrosine to tyramine, histidine to histamine, serine to ethanolamine, and the like). Accordingly, in certain embodiments, provided herein are compositions comprising minerals in bioavailable form that are readily adsorbed but that do not require the addition of an amino acid that may produce toxic metabolites or malodors. In certain embodiments, methods for treating a vaginal infection, such as bacterial vaginosis, comprise administering a composition comprising a mineral salt (e.g., zinc gluconate) and a sulfonic acid (e.g., taurine) that is amino acid free (i.e., a composition that lacks an amino acid, either a standard amino acid or non-standard amino acid).

As discussed herein, a zinc salt alone may not be delivered in an adequate and effective amount to tissue and to the cells of the tissue to provide therapeutic benefit. Without wishing to be bound by any particular theory, combining the mineral salt, such as a zinc salt (including zinc gluconate), with a sulfonic acid (e.g., taurine) may improve delivery to a site of the mucosal or dermal injury, damage, and/or inflammation. Thus, the mineral salt can effect, among other benefits, inhibition of endothelial or epithelial cell junction damage, including inhibiting disruption or dissociation of intercellular junction complexes.

Sulfonic Acids

The compositions described herein that are useful for treating dermal diseases, conditions, and disorders and mucosal diseases, conditions, and disorders, (including those that are inflammatory disorders or that are associated with inflammation), comprise both a mineral salt and a sulfonic acid. As defined herein, a sulfonic acid is an organic acid that is represented by the formula R—S($=$O)$_2$—OH (also depicted as R—SO$_3$H) wherein R is an alkyl that may be optionally substituted. "Alkyl" means a straight chain or branched, noncyclic or cyclic, unsaturated or saturated aliphatic hydrocarbon containing from 1 to 8 carbon atoms, while the term "$C_{1-8}$ alkyl" has the same meaning. Representative saturated straight chain alkyls include methyl, ethyl, n-propyl, n-butyl, n-pentyl, n-hexyl, and the like, while saturated branched alkyls include isopropyl, sec-butyl, isobutyl, tert-butyl, heptyl, n-octyl, isopentyl, 2-ethylhexyl and the like. Representative saturated cyclic alkyls include cyclopropyl, cyclobutyl, cyclopentyl, cyclohexyl, —CH$_2$cyclopropyl, —CH$_2$cyclobutyl, —CH$_2$cyclopentyl, —CH$_2$cyclohexyl, and the like; unsaturated cyclic alkyls include cyclopentenyl and cyclohexenyl, and the like. Cyclic alkyls, also referred to as "homocyclic rings," include di- and poly-homocyclic rings such as decalin and adamantyl. Unsaturated alkyls contain at least one double or triple bond between adjacent carbon atoms (referred to as an "alkenyl" or "alkynyl." respectively).

As used herein, the term "substituted" in the context of alkyl means that at least one hydrogen atom of the alkyl is replaced with a substituent. In the instance of an oxo substituent ("$=$O"), two hydrogen atoms are replaced. A "substituent" as used within the context of this disclosure includes oxo, halogen, hydroxy, cyano, nitro, amino, alkylamino, dialkylamino, alkyl, alkoxy, thioalkyl, haloalkyl, substituted alkyl, heteroalkyl, substituted alkyl, heteroalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocycloalkyl, substituted heterocycloalkyl, —NR$_a$R$_b$, —NR$_a$C($=$O)R$_b$, —NR$_a$C($=$O)NR$_a$R$_b$, —NR$_a$C($=$O)OR$_b$, —NR$_a$S($=$O)$_2$R$_b$, —OR$_a$, —C($=$O)R$_a$, —C($=$O)OR$_a$, —C($=$O)NR$_a$R$_b$, —OCH$_2$C($=$O)NR$_a$R$_b$, —OC($=$O)NR$_a$R$_b$, —SH, —SR$_a$, —SOR$_a$, —S($=$O)$_2$NR$_a$R$_b$, —S($=$O)$_2$R$_a$, —SR$_a$C($=$O)NR$_a$R$_b$. —OS($=$O)$_2$R$_a$ and —S($=$O)$_2$OR$_a$ (also written as —SO$_3$R$_a$), wherein R$_a$ and R$_b$ are the same or different and independently hydrogen, alkyl, haloalkyl, substituted alkyl, alkoxy, aryl, substituted aryl, arylalkyl, substituted arylalkyl, arylalkoxy, heteroaryl, substituted heteroaryl, heteroarylalkyl, substituted heteroarylalkyl, heterocycle, substituted heterocycle, heterocycloalkyl or substituted heterocycloalkyl.

In specific embodiments, R is an alkyl substituted with an amino group ("amino" refers to the —NH$_2$ radical). In yet another specific embodiment. R is a straight chain alkyl, substituted with amino (e.g., R is —(CH$_2$)$_n$NH$_2$ wherein n is 1-6). In a more specific embodiment, the compositions used in the methods described herein comprise the sulfonic acid taurine (2-aminoethanesulfonic acid), having the formula NH$_2$CH$_2$CH$_2$SO$_3$H. Without wishing to be bound by theory, the amino group of taurine would be expected to bind to metal ions and although the affinity of a sulfonate group for metal ions is weak, the presence of the amino group may further serve as an 'anchor' allowing the formation of stable six-membered chelate rings. Thus, taurine may coordinate to metal ions in a monodentate or bidentate manner (see, e.g., "Interaction of Taurine with Metal Ions", O'Brien, et al., *Advances in Experimental Medicine and Biology*, Springer Netherlands, 2002).

As described herein, taurine is a sulfonic acid and is not a standard amino acid and, consequently, is not incorporated into a polypeptide by the process of protein synthesis, either naturally occurring or synthetic. Taurine does not contain a carboxyl group that is necessary for peptide bond formation, and taurine is not a substrate for tRNA synthetase or charged to a transfer RNA (tRNA). Sulfonic acids may also be derived from other amino acids such as methionine and homocysteine, and related molecules such as S-adenosylmethionine, by decarboxylation (e.g., a decarboxylated methionine). Taurine, and other sulfonic acids, may be synthesized by methods described and routinely practiced in the art (see, e.g., Kosswigg, "Sulfonic Acids. Aliphatic," In *Ullmann's Encyclopedia of Industrial Chemistry* (John Wiley & Sons, 2000), and the reactants are available commercially. Taurine for pharmaceutical use is also commercially manufactured and available.

Taurine is a naturally occurring sulfonic acid, and in mammals is synthesized in the liver via the cysteine sulfinic pathway wherein cysteine is an initial reactant. Studies have described that taurine is involved in numerous physiological processes, including neurological, metabolic, cardiovascular, and skeletal muscular functions.

Physiologically Acceptable Compositions and Methods of Administration and Dosing Provided herein are physiologically acceptable (i.e., physiologically suitable and pharmaceutically suitable and acceptable) compositions that may be administered to a subject for treating a dermal or mucosal disease, disorder, or condition. As described herein these compositions comprise at least one mineral salt and at least one sulfonic acid. In more particular embodiments, the mineral salt is zinc gluconate and the sulfonic acid is taurine. In certain embodiments, the compositions further comprise a lactoferrin. The physiologically acceptable compositions described herein may be a sterile (or in some instances non-sterile) aqueous or non-aqueous solution, suspension or emulsion, or solid (all of which are described in greater detail herein), which typically additionally comprise a physiologically acceptable excipient (pharmaceutically acceptable or suitable excipient, diluent, or carrier) (i.e., a non-toxic material that does not interfere with the activity of the active ingredient).

Many existing topical formulations are inadequate because they produce local irritation and are not well tolerated. Therefore, provided herein are compositions (e.g., a topical formulation) comprising a mineral salt, for example, a zinc salt (e.g., zinc gluconate) or a mineral gluconate salt, and a sulfonic acid (e.g., taurine) or a sulfonic acid of a decarboxylated sulfur-containing amino acid that addresses deficiencies in presently available treatments.

In certain embodiments, the methods described herein comprise administering a composition that includes the mineral salt, such as zinc gluconate, and the sulfonic acid, such as taurine, as the active ingredients and that lacks any amino acids (i.e., the compositions are amino acid free). A composition that is amino-acid free lacks the presence of a naturally occurring or synthetically produced amino acid. Unlike certain previously described compositions (see, e.g., U.S. Pat. Nos. 4,937,234; 4,711,780), an amino acid is not required in the compositions described herein that comprise a zinc salt. As understood in the art, an amino acid is an organic molecule comprising both a carboxyl group (COOH) and an amino group ($NH_2$), which form peptide bonds with other amino acids to form peptides and polypeptides. Thus, compositions that are amino acid free lack the twenty standard amino acids encoded by codons of the genetic code. These compositions also lack non-standard amino acids described in the art including those rarely encoded by the genetic code, such as selenocysteine and pyrrolysine, and those not encoded by the genetic code, such as but not limited to lanthionine, 2-aminoisobutyric acid, and dehydroalanine. The term, amino acid-free, is intended to encompass an amino acid molecule and is not intended to encompass a peptide and polypeptide that are formed by peptide bonding of amino acids.

The compositions comprising a mineral salt and a sulfonic acid (for example, zinc gluconate and taurine, respectively) also have antimicrobial activity. The antimicrobial activity includes bactericidal activity against Gram negative and Gram positive bacteria; and anti-fungal activity (e.g., anti-*Aspergillus* activity), including anti-fungal activity against yeast (e.g., *Candida albicans*). In certain embodiments, the compositions used in the methods described herein lack an additional agent that is known to have anti-viral, anti-bacterial, or anti-fungal activity. Accordingly, in certain embodiments, a composition useful for treating mucosal and dermal disorders is a composition that comprises a mineral salt (e.g., zinc gluconate) and a sulfonic acid (e.g., taurine) and that lacks the presence of a third active ingredient with antimicrobial activity (such as, for example but not limited to, methylparaben, polymixin B, tobramycin, and amphotericin B, or vancomycin that is present in sufficient amounts as would be understood by a person skilled in the infectious disease art to inhibit, prevent, treat, or abrogate a microbial infection in the subject). In other embodiments, the compositions described herein that comprise a sulfonic acid (e.g., taurine) and a mineral salt (e.g., a zinc salt, for example, zinc gluconate) may further comprise at least one third active ingredient that is an antimicrobial agent. In other particular embodiments, the compositions described herein do not include (i.e., lack) ascorbic acid or a salt thereof.

As described herein, the mineral moiety of a mineral salt may be, but is not limited to, zinc, calcium, magnesium, manganese, cobalt, chromium, selenium, vanadium, copper, and iron. In particular embodiments, the mineral moiety of the mineral salt is zinc. The salt moiety of the mineral salt may be any suitable inorganic or organic acid, including but not limited to, gluconate, acetate, ascorbate, and sulfate. In particular embodiments, the salt moiety is gluconate. In a specific embodiment, the mineral salt is zinc gluconate wherein the mineral moiety is zinc and the salt moiety is gluconate. In more specific embodiments, compositions disclosed herein may contain a mineral salt (e.g., zinc gluconate) from 0.01% (w/w) to 30% (w/w), from 0.1% (w/w) to 30%, from 0.25% (w/w) to 5.5% (w/w), from 0.5% (w/w) to 20% (w/w), from 1% (w/w) to 15% (w/w), from 1% (w/w) to 5% (w/w), from 2% (w/w) to 5% (w/w), about 0.5% (w/w), about 1% (w/w), about 2% (w/w), about 2.5% (w/w), about 3% (w/w), about 4% (w/w), about 4.5% (w/w), about 5% (w/w), or about 5.5% (w/w). In yet more specific embodiments, compositions described herein comprise the mineral salt (e.g., a zinc salt, for example, zinc gluconate) at 0.5%, 1.0%, 1.5%, 2.0%, or 2.5% (w/w).

In certain embodiments these compositions contain a sulfonic acid (for example, taurine) at a percent weight in the composition at a percent within the range from 0.01% (w/w) to 35% (w/w), from 0.1% (w/w) to 35%, from 0.25% (w/w) to 30% (w/w), from 0.5% (w/w) to 8% (w/w), from 0.5% (w/w) to 20% (w/w), from 1% (w/w) to 15% (w/w), from 1% (w/w) to 5% (w/w), from 2% (w/w) to 5% (w/w), from 0.5% to 4% (w/w), or at about 0.5% (w/w), 1% (w/w), 2% (w/w), 3% (w/w), 4% (w/w), 5% (w/w), 6% (w/w), 7% (w/w), or 8% (w/w). In specific embodiments, the sulfonic acid is taurine. The ingredients (also called herein, components) of the compositions described herein are presented in percent weight of each ingredient to the composition. In certain embodiments, the solute (or diluent) used to formulate the composition is water and in other certain embodiments, the solute is saline (both of which are understood to be from pharmaceutically suitable sources when the compositions are to be used for administration to a subject). When the solute is water, the percentage by weight of each ingredient will be similar to weight per volume of the composition.

In any composition disclosed herein, the molar ratio of a mineral salt (e.g., a zinc salt, for example, zinc gluconate) relative to a sulfonic acid (e.g., taurine) may be from 0.5 to 1.0, at 1 to 1, from 1 to 1.5, from 1 to 2, from 1 to 2.5, from 1 to 3, from 1 to 5, from 1 to 10, or from 1 to 20, 1 to 50, or 1 to 100. In particular embodiments, the compositions comprise a mineral salt and sulfonic acid at a ratio of 1 to 2 (1:2). In a specific embodiment, a composition is provided comprising zinc gluconate and taurine at a molar ratio of 1:2. In certain specific embodiments, the compositions for use in the methods described herein (e.g., for treating a mucosal or dermal disorder and/or for inhibiting disruption of intercellular junctions between adjacent cells) comprise a mineral salt (e.g., a zinc salt, for example, zinc gluconate) at a percent weight in the composition of between about 0.25% (w/w)-5.5% (w/w) or from about 0.5% (w/w)-2.5% (w/w). These compositions also comprise a sulfonic acid (e.g., taurine) at a percent weight in the composition of about 0.25% (w/w)-30% (w/w), 0.5% (w/w) to 8% (w/w), or about 1.0% (w/w)-5.0% (w/w). In more specific embodiments, the composition comprises a mineral salt (e.g., a zinc salt, for example, zinc gluconate) at a percent weight in the composition of about 0.5% (w/w) and a sulfonic acid (e.g., taurine) at a percent weight in the composition of about 1.0% (w/w); in other more specific embodiments, the composition comprises a mineral salt (e.g., a zinc salt, for example, zinc gluconate) at a percent weight in the composition of about 2.5% (w/w) and a sulfonic acid (e.g., taurine) at a percent weight in the composition of about 5.0% (w/w).

The compositions described herein may be formulated at a pH appropriate and effective for the condition to be treated. The physiologically acceptable compositions described herein, therefore, may include at least one buffering agent (also referred to herein as a pH adjusting agent) or any combination or mixture of more than one buffering agent. Exemplary buffering agents include sodium hydroxide, hydrochloric acid, and sodium bicarbonate. A buffering agent may have a pKa ranging from about 3.5 to about 9, or from about 4 to about 5, or from about 4.5 to about 5.5, or from about 6 to about 8, etc., whichever is suitable for maintaining the desired pH of the composition.

The pH of a composition described herein may be adjusted depending upon the intended site of administration. The composition may be formulated to have a pH range from between pH 3 and pH 8, from between pH 4.5 and pH 5.5, from between pH 5.5 and pH 6.5, from between pH 6.5 and pH 7.5, from between pH 7.5 and pH 8.5, from between pH 6 and pH 7, from between pH 7 and pH 8, or from between pH 3.5 and pH 5.5. Such compositions may be used in the methods described herein that comprise orally and/or topically administering the composition for treating any of the mucosal or dermal conditions, diseases, or disorders described herein. For example, the composition may be administered topically to the oral mucosa, and administered orally to treat a mucosal disorder of the gastrointestinal or oropharyngeal tract, such as oral mucositis. In a particular embodiment, the composition used in methods for administration orally and for administration orally and/or topically to the oral mucosa, such as for treating oral mucositis and other oral mucosal disorders, a composition having a neutral pH is formulated and has a pH from between pH 5.5 and pH 7.5.

In other embodiments, the compositions for use in the methods described herein that comprise a mineral salt and a sulfonic acid, such as taurine, may be formulated at an acid pH such as between pH 3.5-4.5, which is a pH range normally found at the vaginal mucosa or intestinal tract. Accordingly, for treating urogenital diseases, disorders, or conditions. (including but not limited to atrophic vaginitis, vaginal dryness, vaginal burning, vaginal ulceration, dyspareunia, leukorrhea, vulvar pruritus, and vulvar burning), a pH range between pH 3 and pH 5, from between pH 3.5 and 4.5, from between pH 4 and pH 5, from between pH 4.5 and pH 5.5, from between pH 5.5 and pH 6.5, or between pH 5 and pH 6 may be used. In particular embodiments, the composition used in methods for urogenital administration, for example to treat atrophic vaginitis, has a pH from between 3.5 and 4.5. Because the sulfonic group of taurine has a low pKa (1.5), taurine is expected to remain negatively charged within the pH range normally found in the vaginal mucosa.

The compositions described herein may additionally comprise a physiologically acceptable excipient (pharmaceutically acceptable or suitable excipient or carrier) (i.e., a non-toxic material that does not interfere with the activity of the active ingredient). Physiologically acceptable compositions may also contain other components, which may be biologically active or inactive. Compositions comprising a mineral salt and a sulfonic acid may further comprise one or more agents and compounds, such as a viscosity modulating agent, a flavoring agent, a mucoadhesive agent, a solubilizing agent, a mucosal absorption-promoting agent, a penetration-promoting agent, and a stabilizing agent. As discussed herein, the compositions may further comprise acidifying agents, alkalizing agents, and/or buffering agents. The compositions may also include one or more pharmaceutically acceptable additives such as antimicrobial preservatives, antioxidants, chelating agents, complexing agents, solubilizing agents, emulsifying agents, humectants, solvents, suspending and/or tonicity agents, wetting agents and other biocompatible materials. The inclusion of such agents will depend upon the disease or disorder to be treated, the administration route, and the part of the body or tissue to be treated and to which the composition is administered.

In certain embodiments, the compositions described herein further comprise a viscosity modulating agent, such as a thickening agent (also called a thickener), which includes but is not limited to a viscosity enhancer (also called a viscosity enhancing agent or a viscosity increasing agent). A thickening agent increases the viscosity of the composition. For example, viscosity-enhancing agents include polyvinylpyrrolidone (PVP) and hyaluronic acid. Each of PVP and hyaluronic are available in mixtures of polymers of varying molecular weights (e.g., K60, K85, K95K100, which are available from commercial vendors). The compositions described herein, in certain embodiments, may be formulated with from about 0.04 to about 15% by weight of a K60 to K100 PVP. A viscosity-enhancing agent such as PVP (including K60 to K90 PVP) may be formulated at low percent weight of the composition (e.g., from 0.5% (w/w) to 5.0% (w/w)) to achieve a composition of low viscosity, or at higher percent weight of the composition (e.g., from about 5.1% (w/w) to about 10% (w/w), 12.5% (w/w), 15% (w/w) or higher) to achieve a composition of high viscosity. In other embodiments, PVP is from about K85 and K95 and is from about 3 and 10% by weight of the composition. In still another embodiment, PVP is from about 7%-10% (w/w). (See U.S. Pat. No. 6,828,308, which is incorporated by reference in its entirety.)

The compositions described herein comprising a mineral salt and a sulfonic acid may further comprise hyaluronic acid. In certain embodiments, the compositions comprise a mineral salt, a sulfonic acid, hyaluronic acid, and PVP. The compositions described herein may comprise from about 0.01 to about 5% by weight of hyaluronic acid (i.e., between from about 0.01-5.0% (w/w)), or a pharmaceutically acceptable salt thereof, having a molecular weight from between about 1.6 and 2.2 million Daltons. In other embodiments, hyaluronic acid, or the pharmaceutically acceptable salt thereof, is from about 1.8 to about 2.0 million Daltons and from about 0.01 to about 2% by weight. In still another embodiment, hyaluronic acid, or the pharmaceutically acceptable salt thereof, is from about 1.8 to about 2.0 million Daltons and from about 0.01 to about 2% by weight of the composition.

Solubilizing agents useful for including in the compositions described herein include, but are not limited to, at least one or more of cyclodextrin, hydroxypropyl-β-cyclodextrin, sulfobutylether-β-cyclodextrin, and methyl-β-cyclodextrin. A sulfonic acid (e.g., taurine) as described herein may also act as a solubilizing agent, solubilizing a mineral salt (e.g., a zinc salt, for example, zinc gluconate), which may increase bioavailability of the mineral salt. The addition of a sulfonic acid (for example, taurine) allows for subsequent pH adjustment with an appropriate acid or base without consequent precipitation of the mineral salt. The pH of the compositions may then be adjusted with the appropriate pH adjusting agent (i.e., an acid or base), neutralizing the mineral salt when the composition is applied for treating conditions for which a neutral pH is desired (e.g., oral mucositis) or maintaining or adjusting to an acid pH when the composition is applied for treating conditions for which an acid pH is desired (e.g., atrophic vaginitis) as well as solubilizing a mineral salt (e.g., zinc gluconate).

The methods described herein for treatment of mucosal diseases, disorders, and conditions may be more effective when the composition comprises one or more agents that increase (i.e., enhance) the residence time of the mineral salt and the sulfonic acid at the mucosal delivery site (e.g., oral mucosa or vaginal mucosa) (i.e., maintain the presence of the mineral salt and sulfonic acid for a longer period of time at the mucosal site to which the composition is delivered or administered than would occur in the absence of such an agent). Accordingly, polymeric delivery vehicles and other agents that contribute to increasing (i.e., improving) residence time, for example, sustained release-enhancing formulations, such as polyethylene glycol (PEG) (e.g., PEG-40), and methods for delivery same are described herein.

In certain embodiments, the compositions may be formulated for mucosal delivery. The physiologically acceptable compositions comprising at least one mineral salt, such as a zinc salt, and one or more sulfonic acids (e.g., taurine) may be combined or coordinately administered with a suitable carrier or vehicle for delivery to a mucosal or epithelial surface. By coordinate delivery is meant that at least two compositions are sequentially administered to a subject in need of treatment, which can be prophylactic or therapeutic in its use. By way of example, a composition that increases the bioavailability, such as by increasing or maintaining the residence time of the mineral salt and/or the sulfonic acid, may be administered before or after the composition comprising the mineral salt and sulfonic acid.

The compositions described herein that comprise a mineral salt and a sulfonic acid may further comprise an absorption promoting agent. The amount of each active ingredient that is formulated in a composition with one or more additional agents to produce a single dosage form will vary depending upon the particular mode of administration. While the mechanism of absorption promotion may vary with different mucosal delivery-enhancing agents, useful reagents in this context will not adversely affect the mucosal tissue in a biologically or statistically significant manner and will be selected according to the physicochemical characteristics of the particular mineral salt (e.g., a zinc salt, for example, zinc gluconate) and sulfonic acid (e.g., taurine), and other agents included in the composition. Delivery-enhancing agents that increase penetration or permeability of mucosal tissues may cause some alteration of the protective permeability barrier of the mucosa. A delivery-enhancing agent useful for the methods described herein are those that if administration of such an agent causes significant changes in permeability of the mucosa that these changes may be reversible within a time frame appropriate to the desired duration of drug delivery. Furthermore, a suitable delivery-enhancing agent has no substantial, cumulative toxicity, and does not induce permanent deleterious changes in the barrier properties of the mucosa, particularly when the compositions described herein are intended for long-term use.

The compositions described herein comprising a mineral salt (e.g., a zinc salt, for example, zinc gluconate) and a sulfonic acid (e.g., taurine) may also include absorption-promoting agents. An absorption-promoting agent may be selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacylmethyl sulfoxide, azone, sodium laurylsulfate, oleic acid, and the bile salts, may be employed to enhance mucosal delivery or penetration. In further embodiments, surfactants (e.g., polysorbates such as polysorbate 20 and polysorbate 80) are employed as adjunct compounds, processing agents, or formulation additives to enhance mucosal delivery.

Other mucosal absorption-promoting agents are selected from a variety of compounds, compositions, and molecules that enhance mucosal delivery, stability, activity or transepithelial penetration. These include, inter alia, cyclodextrins (e.g., cyclodextrin) and β-cyclodextrin derivatives (e.g., hydroxypropyl-β-cyclodextrin, sulfobutylether-β-cyclodextrin, methyl-β-cyclodextrin and heptakis(2,6-di-O-methyl-β-cyclodextrin)). These compounds, optionally conjugated with one or more of the active ingredients and further optionally formulated in an oleaginous base, enhance bioavailability of the one or more active ingredients (such as the mineral salt, sulfonic acid, and/or a lactoferrin). Yet additional absorption-enhancing agents adapted for mucosal delivery include medium-chain fatty acids, including mono- and diglycerides (e.g., sodium caprate—extracts of coconut oil, CAPMUL®), and triglycerides (e.g., amylodextrin, Estaram 299. MIGLYOL® 810).

Compositions described herein may also be supplemented with any suitable penetration-promoting agent that facilitates absorption, diffusion, or penetration of a mineral salt (e.g., zinc gluconate) or sulfonic acid (e.g., taurine) across mucosal barriers. The penetration-promoting agent may be any such agent that is pharmaceutically acceptable. Thus, in certain embodiments, compositions are provided that incorporate one or more of the penetration-promoting agents selected from sodium salicylate and salicylic acid derivatives (acetyl salicylate, choline salicylate, salicylamide, etc.). Also provided as penetration-promoting agents are substances that are generally used as emulsifiers (e.g., sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters, and the like.

A physiologically acceptable carrier or excipient includes a pharmaceutically acceptable solid or liquid filler, diluent, or encapsulating material. A water-containing liquid carrier can contain pharmaceutically acceptable additives such as any one or any combination of acidifying agents, alkalizing agents, antimicrobial preservatives, antioxidants, buffering agents, chelating agents, complexing agents, solubilizing agents, emulsifying agents, humectants, solvents, suspending and/or viscosity-increasing agents (e.g., a thickener), tonicity agents, wetting agents or other biocompatible materials.

Exemplary materials that may be included in the compositions described herein as pharmaceutically acceptable carriers or excipients are sugars, such as lactose, glucose, sodium saccharin and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, castor oil (e.g., hydrogenated castor oil), corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide, sodium hydroxide and aluminum hydroxide; alginic acid; pyrogen-free water, purified water, isotonic saline, acetate, lactate, formate, and glycolate, Ringer's solution, ethyl alcohol and phosphate buffer solutions, as well as other non toxic compatible substances typically used or generally regarded as safe (GRAS) to use in pharmaceutical formulations. Such agents may be used individually or in any combination, or at any concentration. In certain embodiments, the compositions described herein comprise glycerin as an excipient, which is formulated at a percent weight from about 0.01 to about 3% by weight of the composition.

The compositions may also include humectants including, but are not limited to, propylene glycol, glycerin, glyceryl triacetate, a polyol, a polymeric polyol, lactic acid, and urea. The physiologically acceptable compositions described herein may comprise one humectant or any combination or mixture of more than one (i.e., at least two) humectants.

The compositions described herein may also comprise one or more wetting agents, emulsifiers, and lubricants such as sodium lauryl sulfate and magnesium stearate, as well as coloring agents, release agents, coating agents, sweetening, flavoring and perfuming agents, preservatives and antioxidants can also be present in the compositions disclosed herein. Exemplary flavoring agents include essential oils, synthetic flavors, fruit essences, anise, flavor oils, citrus oil, peppermint oil, spearmint oil, mint oil, clove oil, oil of wintergreen, menthol, eucalyptol, thymol, and the like, and combinations thereof. The compositions may also include an agent that is described in the art as a flavor altering agent, such as glycyrrhetinic acid, that masks the flavor of an otherwise less palatable or less pleasant tasting composition. A flavoring agent and/or flavor altering agent may be used in a composition disclosed herein at a concentration of from 0.05% to 3.0% (w/w), from 0.1% (w/w) to 20% (w/w), from 0.5% (w/w) to 1.5% (w/w), from 1.5% (w/w) to 2% (w/w), from 2% (w/w) to 3% (w/w), from 3% (w/w) to 4%, or from 5% to 10%, 15%, or 17% (w/w). In a particular embodiment, glycyrrhetinic acid, or a pharmaceutically acceptable salt thereof, may be formulated with the compositions described herein at a percent weight from about 0.01 to about 3% by weight of the composition.

As used herein, examples of emulsifying agents include lecithin, $C_{10}$ to $C_{12}$ fatty acids, mono and diacyl glycerides, ox bile extract, polyglycerol esters, polyethylene sorbitan esters, propylene glycol, sorbitan monopalmitate, sorbitan monosterate, sorbitan tristerate, enzyme modified lecithin, hydroxylated lecithins, and combinations thereof. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), ethylene glycol tetraacetic acid (EGTA), sorbitol, tartaric acid, phosphoric acid and the like.

Other pharmaceutically acceptable agents having any one or more of the properties described herein can be found in the U.S. Pharmacopeia National Formulary, 1990, 1857-1859. Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, $21^{st}$ Ed. Mack Pub. Co., Easton, Pa. (2005)). In general, as discussed herein, the type of excipient is selected on the basis of the mode of administration. Pharmaceutical compositions may be formulated for any appropriate manner of administration, including, for example, topical, oral, nasal, intrathecal, buccal, rectal, vaginal, intraocular, subconjunctival, sublingual or parenteral administration, including subcutaneous, intravenous, intramuscular, intrasternal, intracavernous, intrameatal or intraurethral injection or infusion.

The compositions may further comprise ingredients that act as delivery vehicles, including but not limited to aluminum salts, water-in-oil emulsions, biodegradable oil vehicles, oil-in-water emulsions, biodegradable microcapsules, and liposomes. While any suitable excipient or carrier known and available to a person having skill in the art may be employed in the compositions described herein, the type of carrier will vary depending on the mode of administration and whether a sustained release is desired. In the methods described herein, a pharmaceutical composition may be administered through use of insert(s), bead(s), timed-release formulation(s), patch(es) or fast-release formulation(s).

For parenteral administration, such as subcutaneous injection, the carrier preferably comprises water, saline, alcohol, a fat, a wax or a buffer, and the composition is sterile. For oral administration, any of the above carriers or a solid carrier, such as mannitol, lactose, starch, magnesium stearate, sodium saccharin, talcum, cellulose, glucose, sucrose, and magnesium carbonate, may be employed. Biodegradable microspheres (e.g., polylactic galactide) may also be used as carriers for the compositions described herein. Suitable biodegradable microspheres described, for example, in U.S. Pat. Nos. 4,897,268 and 5,075,109. In particular embodiments in which the composition is combined with a microsphere, the microsphere is larger than approximately 25 microns. A composition described herein may be lyophilized or otherwise formulated as a lyophilized product using one or more appropriate excipient solutions (e.g., sucrose) as diluents upon administration.

A pharmaceutical composition (or a physiologically acceptable formulation) disclosed herein may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. As discussed in greater detail herein, thickening agents may be present in a pharmaceutical composition for topical administration (e.g., oral or vaginal). The compositions described herein may be administered by using any one of several delivery vehicles described herein and used in the art, including but not limited to a sponge, gel cap, suppository, gauze (or other suitable fabric for application to the tissue to be treated), and a lozenge. With respect to certain delivery vehicles, such as a sponge, fabric, or gauze, the composition is attached to, absorbed by, adsorbed to, or in some manner applied to the vehicle that permits release of the composition upon contact with the tissue to be treated.

A composition disclosed herein may be intended for rectal (for treatment of a rectal mucosa), oral, or vaginal administration, in the form, e.g., of a suppository or lozenge, which will melt in the rectum, oral, or vaginal space, and release the drug or components of the composition. A composition described herein that is administered orally may also be in the form of a liquid. The composition for rectal administration may contain an oleaginous base as a suitable nonirritating excipient. Such bases include, without limitation, lanolin, cocoa butter and polyethylene glycol.

The compositions described herein may be endotoxin free, particularly when delivered parenterally. An endotoxin free composition that comprises a mineral salt and a sulfonic acid and that further comprises one or more agents described herein is substantially free of endotoxins and/or related pyrogenic substances (i.e., an endotoxin is not detectable by methods accepted by regulatory agencies to demonstrate with sufficient sensitivity whether an endotoxin is present). Endotoxins include toxins that are present in viable microorganisms and include toxins that are released only when the microorganisms lack cell integrity or die. Pyrogenic substances include fever-inducing, thermostable substances (lipopolysaccharides and glycoproteins) located in the outer membrane of bacteria and other microorganisms. These substances can cause fever, hypotension, and shock when administered to humans. Manufacturing compositions that are endotoxin-free can require special equipment, expert artisans, and can be significantly more expensive than making formulations that are not endotoxin-free.

In specific embodiments, the physiologically acceptable compositions that comprise a mineral salt (for example, from between 0.25%-5.5% (w/v) zinc gluconate) and a sulfonic acid (for example, from between 0.5%-8% (w/w) taurine) further comprise one or more of 0.05% to 3.0% (w/w) glycyrrhetinic acid; 0.04% to 15% (w/w) polyvinylpyrrolidone (PVP); 0.01% to 5.0% (w/w) hyaluronic acid; and 0.05% to 3.0% (w/w) glycerin (or from between 0.05% to 5% glycerin). In other specific embodiments, the composition comprises 0.5% (w/w) zinc gluconate, 1.0% (w/w) taurine, and 4.0% PVP (w/w); or alternatively, 0.5% (w/w) zinc gluconate, 1.0% (w/w) taurine, and 8.0% PVP (w/w); or in certain other embodiments, 2.0% (w/w) zinc gluconate, 4.0% (w/w) taurine, and 4.0% PVP (w/w). Without wishing to be bound by theory, inclusion of PVP and hyaluronic acid promote adherence of the composition to mucosa, which provides a protective coating of any exposed nerve endings, thereby reducing pain, promoting cicatrisation and healing of any ulceration, lesion, or microlesion of the mucosa. In other specific embodiments, PVP is absent from the compositions described herein that comprise a mineral salt (e.g., a zinc salt, for example, zinc gluconate) and a sulfonic acid (e.g., taurine).

In other certain embodiments, the methods described herein may include administering a composition that is formulated to contain purified water, PVP, taurine, zinc gluconate, PEG-40, hydrogenated castor oil, sodium saccharin, sodium hydroxide and a flavoring agent. In other specific embodiments, the composition comprises purified water, PVP, taurine, zinc gluconate, PEG-40, hydrogenated castor oil, sodium saccharin, sodium hydroxide, and a flavoring agent. In a specific embodiment, a composition is provided that comprises 0.5% (w/w) zinc gluconate, 1.0% (w/w) taurine, 1.0% (w/w) glycyrrhetinic acid (a flavoring agent, also referred to herein as a flavor modifying or altering agent), 1.0% (w/w) polyvinylpyrrolidone (PVP, which acts as a viscosity enhancing or thickening agent), 0.1% (w/w) hyaluronic acid, and 0.1% (w/w) glycerin. In a specific embodiment, the pH of the composition is adjusted to be a neutral pH, for example, between pH 5.5 and 7.5. In other certain embodiments, the pH of the composition is adjusted to between 3.5 and 4.5. Because the above composition has a PVP percent by weight of 1.0%, this formulation would be considered low viscosity.

In another embodiment, the composition may be formulated to comprise 0.5% (w/w) zinc gluconate, 1.0% (w/w) taurine, 1.0% (w/w) glycyrrhetinic acid, 8.0% (w/w) polyvinylpyrrolidone (PVP), 0.1% (w/w) hyaluronic acid, 0.1% (w/w) glycerin. In certain embodiments, the pH of the composition is adjusted to between pH 3.5 and 4.5. Such a composition may be used to treat urogenital mucosal diseases and disorders described herein, including but not limited to vaginal dryness and atrophic vaginitis.

In other specific embodiments, the methods described herein comprise administering a composition comprising a mineral salt and a sulfonic acid with the proviso that a composition consisting of deionized water, zinc gluconate, ascorbic acid, methylcellulose, taurine, methylparaben, propylparaben, and F.D. & C. Blue No: 1 and a composition consisting of deionized water, zinc gluconate, carboxymethylcellulose, taurine, methylparaben, propylparaben, and F.D. & C. Blue No: 1 are each excluded.

In certain embodiments, the methods for treating a mucosal or dermal disease, disorder, or condition comprise administering the compositions comprising a mineral salt and a sulfonic acid (which are described in detail herein) enterally (i.e., orally) or topically. Topical administration refers to administration of the composition to the surface of the tissue to be treated and to which the composition will have a beneficial effect, such as to a mucous membrane, including but not limited to, an oropharyngeal mucous membrane, vaginal mucous membrane, or anal mucous membrane. Enteral administration includes oral administration (i.e., administered orally) to the oropharyngeal cavity. When a composition is administered orally, the components of the composition are likely absorbed systemically and have a systemic effect and may also be absorbed topically (or have a topical effect). In certain specific embodiments, the compositions described herein that comprise a mineral salt (e.g., zinc gluconate) and a sulfonic acid (e.g., taurine) may be administered topically in the form of a gel.

In other embodiments, the compositions described herein further comprise a protein or polypeptide that exhibits properties and characteristics that are useful for treating one or more of the mucosal and dermal disorders and associated inflammation described herein. In certain embodiments, the polypeptide is a transferrin, and in a specific embodiment, the transferrin is lactoferrin.

The preparations and compositions described herein comprise a lactoferrin, which is a globular, cationic, non-heme iron-binding protein. Lactoferrin is a prominent glycoprotein in milk, other secretory fluids, and white blood cells, and is synthesized by exocrine glands and by neutrophils at infection and inflammation sites, has been shown to have antibacterial, antiviral, and anti-fungal, and anti-inflammatory properties (see, e.g., Conneely. *J. Amer. Coll. Nutr.* 20(5):389S-395S, 2001; van der Strate et al., *Antiviral Res.* 52: 225-39 (2002); Antonini. *Cell. Mol. Life Sci.* 62: 2576-

87 (2006); Ward et al., *Cell. Mol. Life Sci.* 62: 2540-48 (2006); Bellamy et al., *Bochim. Biophys. Acta* 1121:130-36 (1992)). Without wishing to be bound by theory, lactoferrin may reduce inflammation by reducing and/or maintaining the production of proinflammatory factors such as IL-1β, IL-6. IL-8, TNF-α, and NF-κB, for example, to a level that reduces, abrogates, prevents, minimizes destructive inflammatory effects (see, e.g., International Application Publication No. WO 2007/065482, which is incorporated herein by reference in its entirety).

Lactoferrin typically contains two bound $Fe^{+3}$ (also referred to as iron III or FeIII) ions. Full-length lactoferrin has a molecular weight of approximately 80 kDa, and belongs to the transferrin family of proteins. The molecular weight of lactoferrin has also been reported to be 78 kDa. The difference in reported molecular size may represent the presence or absence of one N-linked oligosaccharide modification.

Lactoferrin belongs to the family of transferrin proteins, which also includes serum transferrin (see, e.g., Baker et al., *Biochem. Cell Biol.* 80:27-34 (2002) and references cited therein). Lactoferrins between species share approximately 70% sequence identity (see, e.g., Baker, *Adv. Inorg. Chem.* 41:389-463 (1994)). The amino acid sequence of lactoferrin contains a two-fold internal repeat, and the N-terminal half has approximately 40% sequence identity with the C-terminal half, which results in the protein folding into two homologous halves. Compared with serum transferrin, lactoferrin has a more potent iron-withholding activity: lactoferrin retains iron at a ph as low as pH 3.5, whereas, serum transferrin begins to lose iron at pH 6 (see, e.g., Mazurier et al., *Biochim. Biophys. Acta* 629:399-408 (1986); Peterson et al., *Biochemistry* 39:6625-33 (2000)).

Lactoferrin may be human lactoferrin, bovine lactoferrin, murine lactoferrin, or buffalo lactoferrin. In certain embodiments, the compositions described herein comprise bovine lactoferrin; in other embodiments, the compositions comprise human lactoferrin. Bovine lactoferrin can be produced in large quantities by isolating the polypeptide from cow's milk. Lactoferrin may also be obtained from commercial sources. Lactoferrin may also be produced recombinantly according to methods routinely practiced in the molecular biology and protein expression arts.

The majority of full-length human lactoferrin polypeptide species that have been sequenced are 711 amino acids in length, which includes a 19-amino acid signal peptide. Accordingly, an exemplary mature (without the signal peptide) lactoferrin polypeptide has 692 amino acids. Exemplary amino acid sequences for human lactoferrin are located in the GenBank database (National Center for Biotechnology Information (NCBI)) and include but are not in any way limited to Accession Nos. AAA59511.1 (SEQ ID NO:1). ACF19793.1 (SEQ ID NO:2), and AAW71443.1 (SEQ ID NO:3) (see also AAR12276.1). The amino acid sequences of mature human lactoferrin (i.e., without the 19-amino acid signal peptide) are provided in SEQ ID NOS:8, 9, and 10, respectively.

The full-length bovine lactoferrin polypeptide species that have been sequenced are 708 amino acids, and the bovine lactoferrin polypeptides also include a 19-amino acid signal peptide. Accordingly, an exemplary mature (without the signal peptide) lactoferrin polypeptide has 689 amino acids. Exemplary amino acid sequences available in the art for bovine lactoferrin include, but are not limited to, GenBank Accession Nos. AAA30610.1 (SEQ ID NO:4), AAA30617.1 (SEQ ID NO:5), AAA30609.1 (SEQ ID NO:6), and AAA21722.1 (SEQ ID NO:7). The amino acid sequences of mature bovine lactoferrin (i.e., without the 19-amino acid signal peptide) are provided in SEQ ID NOS: 11-14, respectively. The encoding polynucleotide sequences for lactoferrins can be readily obtained in a similar manner from publicly available and privately (i.e., for a fee or supporting membership) available databases or by deducing an encoding polynucleotide sequence from the amino acid sequence.

In certain embodiments, the methods described herein comprise administering lactoferrin, wherein the lactoferrin is a lactoferrin polypeptide fragment (see, e.g., U.S. Pat. No. 7,420,033). As described herein, certain lactoferrin polypeptide fragments retain antimicrobial activity such as a cationic domain at the amino terminal end of lactoferrin, which retains antimicrobial activity (see, e.g., Bellamy, et al., supra; Conneely, supra; Nakamura et al., *Protein Exp. Purif.* 21; 424-31 (2001); Tanaka et al., *Biochem. Cell Biol.* 81: 349-354 (2003)). The antimicrobial activity of lactoferrin is structurally distinct and separate from its iron binding activity. Other fragments described in the art include fragments called lobe N and lobe C, and smaller fragments within each of lobe N and lobe C (see, e.g., International Application Publication No. WO 2007/065482). The amino terminal half of lactoferrin is referred to as the N-lobe (or Lobe N) and the carboxy terminal half is referred to as the C-lobe (or Lobe C). Both lobes have the same fold, which is consistent with the high percent sequence identity between the lobes. Each lobe is subdivided into two domains that are separated by an interdomain cleft that includes an iron binding site (see, e.g., Baker et al., *Biochem. Cell Biol.*, supra). Exemplary human lactoferrin fragments of the amino terminal region of lactoferrin (i.e., Lobe N) include but are not limited to a lactoferrin fragment from amino acid at position 1 to about position 280 of the mature human polypeptide. Lactoferrin fragments of lobe C include but are not limited to a lactoferrin fragment from about amino acid at position 285 to amino acid 692 of the mature human lactoferrin polypeptide. Certain exemplary N lobe fragments of bovine lactoferrin include amino acids at positions 1-333 (see SEQ ID NOS: 11-14), which may in certain embodiments, also include the inter-lobe region (typically residues at positions 334-344) (see, e.g., Bai et al., *Biometals* 2010 Feb. 10, epub ahead of print). The N lobe and/or the C lobe may be obtained by recombinant expression of the lobe polypeptide using molecular biology and protein expression methods known and routinely practiced in the art or the lobe of interest may be obtained by proteolytic digest of the lactoferrin.

Lactoferrin belongs to the family of transferrin proteins, which also includes serum transferrin (see, e.g., Baker et al., *Biochem. Cell Biol.* 80:27-34 (2002) and references cited therein). Lactoferrins between species share approximately 70% sequence identity (see, e.g., Baker. *Adv. Inorg. Chem.* 41:389-463 (1994)). The amino acid sequence of lactoferrin contains a two-fold internal repeat, and the N-terminal half has approximately 40% sequence identity with the C-terminal half, which results in the protein folding into two homologous halves. Compared with serum transferrin, lactoferrin has a more potent iron-withholding activity: lactoferrin retains iron at a ph as low as pH 3.5, whereas, serum transferrin begins to lose iron at pH 6 (see, e.g., Mazurier et al., *Biochim. Biophys. Acta* 629:399-408 (1986); Peterson et al., *Biochemistry* 39:6625-33 (2000)).

The protein surface of the lactoferrin molecule has regions with high concentrations of positive charge that result in a high isoelectric point (~pI 9) for the polypeptide. For example, in human lactoferrin, one region of positive charge includes the N-terminus portion of the mature lactoferrin that has an amino acid sequence of GRRRRS (SEQ ID NO:15) (see, for example, amino acid residues 1-6 of SEQ ID NOS:8, 9, and 10), which projects from the protein surface-terminus of the polypeptide chain, together with the adjacent carboxy terminal portion of helix 1, which includes a positively charged region, for example, the amino acid sequence, RKVR (SEQ ID NO: 16) or RRVR (SEQ ID NO: 17). This region provides a site for binding heparin (see, e.g., Van Berkel et al., Biochem. J. 328:145-151 (1997)) and glycosaminoglycans (see, e.g., Mann et al., J. Biol. Chem. 269: 2366-23667 (1994)) and may be the site that binds to DNA. The N-terminal portion is contiguous with helix 1 of the N-lobe, which forms the main part of the bactericidal domain (see, e.g., Bellamy et al., Biochim. Biophys. Acta 1121:130-136 (1992)), which is characterized by the presence of surface arginine residues. Despite their virtually identical fold, other transferrins do not share this bactericidal activity, presumably because they lack the necessary surface features (see, e.g, Baker, Biochem. Cell Biol., supra).

While bovine lactoferrin (bLf) does not share the same N-terminal repeat of arginine residues, bLf also has a highly positively charged region at its N terminus. In bovine lactoferrin, the domain responsible for bactericidal activity, which is also the heparin binding domain, includes residues 17-42 of the mature bLf polypeptide (Phe-Lys-Cys-Arg-Arg-Trp-Gln-Trp-Arg-Met-Lys-Lys-Leu-Gly-Ala-Pro-Ser-Ille-Thr-Cys-Val-Arg-Arg-Ala-Phe-Ala (SEQ ID NO:18)) (see, for example, SEQ ID NO:11-14) (see, e.g., Bellamy Biochim. Biophys. Acta, supra; Shimazaki et al., J. Dairy Sci. 81:2841-49 (1998)). Motifs, KCRR (SEQ ID NO:19) at positions 18-21 and RMKK (SEQ ID NO:20) at positions 25-28 (see SEQ ID NOS: 11-14), are believed to be particularly important for heparin binding (Shimazaki et al., supra).

In certain embodiments, the methods described herein comprise administering a composition comprising a mineral salt and a sulfonic acid and further comprising lactoferrin, wherein the lactoferrin is a lactoferrin polypeptide fragment (see. e.g., U.S. Pat. No. 7,420,033). As described herein, certain lactoferrin polypeptide fragments retain antimicrobial activity such as a cationic domain at the amino terminal end of lactoferrin, which retains antimicrobial activity (see, e.g., Bellamy, et al., supra; Conneely, supra; Nakamura et al., Protein Exp. Purif. 21; 424-31 (2001); Tanaka et al., Biochem. Cell Biol. 81: 349-354 (2003)). The antimicrobial activity of lactoferrin is structurally distinct and separate from its iron binding activity. Other fragments described in the art include fragments called lobe N and lobe C, and smaller fragments within each of lobe N and lobe C (see, e.g., International Application Publication No. WO 2007/065482). The amino terminal half of lactoferrin is referred to as the N-lobe (or Lobe N) and the carboxy terminal half is referred to as the C-lobe (or Lobe C). Both lobes have the same fold, which is consistent with the high percent sequence identity between the lobes. Each lobe is subdivided into two domains that are separated by an interdomain cleft that includes an iron binding site (see, e.g., Baker et al., Biochem. Cell Biol., supra). Exemplary human lactoferrin fragments of the amino terminal region of lactoferrin (i.e., Lobe N) include but are not limited to a lactoferrin fragment from amino acid at position 1 to about position 280 of the mature human polypeptide. Lactoferrin fragments of lobe C include but are not limited to a lactoferrin fragment from about amino acid at position 285 to amino acid 692 of the mature human lactoferrin polypeptide. Certain exemplary N lobe fragments of bovine lactoferrin include amino acids at positions 1-333 (see SEQ ID NOS:11-14), which may in certain embodiments, also include the inter-lobe region (typically residues at positions 334-344) (see, e.g., Bai et al., Biometals 2010 Feb. 10, epub ahead of print). The N lobe and/or the C lobe may be obtained by recombinant expression of the lobe polypeptide using molecular biology and protein expression methods known and routinely practiced in the art or the lobe of interest may be obtained by proteolytic digest of the lactoferrin.

Lactoferrin has the capability to tightly but reversibly bind two $Fe^{+3}$ (also referred to as ferric ions, iron III, or FeIII) ions together with two carbonate ions ($CO_3^{2-}$). The presence of lactoferrin in tissues and secretions and transferrin in blood assures that iron is tightly complexed. The high affinity for iron (approximately $10^{22}$ M) ensures that the concentration of free iron does not exceed $10^{-18}$ M, at which point ferric hydroxides would precipitate (see, e.g., Aisen et al., "Physical biochemistry of the transferrins" in Iron carriers and iron proteins, vol. 5, Loehr, ed. VCH Publishers, New York, pp. 241-351 (1989); Baker et al., Cell. Mol. Life Sci. 62:2531-2539 (2005)), and which also contributes to lack of microbial growth and formation of reactive oxygen species (see, e.g., Weinberg, Biochim. Biophys. Acta 1790: 600-605 (2009)). Lactoferrin is an important regulator of systemic iron homeostasis and is capable of restoring hematological parameters in hypoferremia and IDA (see, e.g., Paesano et al., Biochimie, supra; Paesano et al., Biochem. Cell Biol. 84:377-380 (2006)). As discussed herein, several functions, dependent and independent of iron binding ability, have been attributed to lactoferrin (see, e.g., Valenti et al. Cell Mol. Life Sci. 62: 2576-87 (2005)).

The biological effects of a lactoferrin may be achieved when the lactoferrin has any degree of saturation of the binding sites for iron (III), wherein "any degree" is understood not to exceed 100%. Even when no iron is bound by the lactoferrin (referred to as the "apo" form wherein the degree of saturation of iron sites is equal to 0%), biological effects may be observed. The biological effects of a lactoferrin may also be achieved when the lactoferrin is partially saturated, or when the lactoferrin is completely saturated (referred to as the "holo" form of the lactoferrin when the degree of saturation of iron sites is equal to 100%). A lactoferrin used in the methods described herein may have any degree of saturation of the iron binding sites ranging from 0% saturation to and including 100% saturation, including but not limited to saturation from 0%-20%, 0-40%, 10-30%, 10-35%, 10-40%, 10-50%, 10-60%, 15-30%, 15-40%, 15-50%, 15-60%, 10-70%, or 10-80%. In a specific embodiment, a lactoferrin has a degree of saturation of the iron binding sites ranging from 15-30%. In another specific embodiment, a lactoferrin has a degree of saturation of the iron binding sites ranging from 10-30% or from 10%-35%. The level of saturation may be achieved by using a mixture of lactoferrin molecules that have differing percent saturation to achieve a desired level of saturation. The binding sites for iron can be occupied at any degree of saturation by Fe (III) and/or optionally, with different kinetics and affinities, by one or more other transition metals that have similar chemical and physical properties. These metals can be, for example, one or more zinc (Zn), copper (Cu), aluminum (Al), gallium (Ga), chromium (Cr) and manganese (Mn). Accordingly, in one embodiment, lactoferrin used in the methods and compositions described herein has any degree of saturation by Fe (III) and one or more of Zn, Cu, and Mn. In another certain embodiment, lactoferrin has any degree of saturation with one or more of Zn, Cu, and Mn.

Lactoferrin can be prepared by isolating the protein from a source of milk or colostrum. Isolated lactoferrin means that the protein is removed (i.e., partially purified, or totally purified such that other components present in the source of lactoferrin are not detectable) from its original environment (e.g., the natural environment if it is naturally occurring). For example, when the polypeptide present in a living animal, it is not considered to be isolated; however, the same polypeptide, separated from some or all or most of the co-existing materials in the natural system, is considered isolated. Alternatively, lactoferrin may be produced recombinantly according to methods routinely practiced by a person skilled in the molecular biology art, particularly given that the polypeptide sequence of lactoferrin and encoding nucleotide sequence have been long known in the art.

The compositions described herein may comprise full length lactoferrin, or truncated lactoferrin, or a fragment of lactoferrin. Truncated molecules are polypeptides that comprise less than the full-length amino acid sequence of the polypeptide. As used herein "deletion" has its common meaning as understood by those familiar with the art, and may refer to molecules that lack one or more of a portion of a sequence from either terminus or from a non-terminal region, relative to a corresponding full length molecule, for example, as in the case of truncated molecules provided herein. Truncated molecules that are linear biological polymers such as polypeptides may have one or more of a deletion from either terminus of the molecule or a deletion from a non-terminal region of the molecule, where such deletions may be deletions of any number of amino acids including a deletion that is one amino acid up to about 675 amino acids. Also provided herein are compositions that comprise a polypeptide that comprises a fragment of lactoferrin as described herein. A lactoferrin fragment may comprise any number of contiguous amino acids between at least 10 and 700 amino acids (including but not limited to at least 10, 20, 40, 60, 80, 100, 120, 150, 200, 300, 400, and 500 amino acids and any whole number of amino acids between 10 and 690).

In certain embodiments, a lactoferrin polypeptide also includes lactoferrin species that have one or more amino acid substitutions, insertions, or deletions (also called herein a lactoferrin variant). Conservative substitutions of amino acids are well known and may occur naturally in the polypeptide or may be introduced when the polypeptide is recombinantly produced. Amino acid substitutions, deletions, and additions may be introduced into a polypeptide using well-known and routinely practiced mutagenesis methods (see, e.g., Sambrook et al. *Molecular Cloning: A Laboratory Manual,* 3d ed., Cold Spring Harbor Laboratory Press, NY 2001)). Oligonucleotide-directed site-specific (or segment specific) mutagenesis procedures may be employed to provide an altered polynucleotide that has particular codons altered according to the substitution, deletion, or insertion desired. Deletion or truncation variants of proteins may also be constructed by using convenient restriction endonuclease sites adjacent to the desired deletion. Subsequent to restriction, overhangs may be filled in and the DNA religated. Alternatively, random mutagenesis techniques, such as alanine scanning mutagenesis, error prone polymerase chain reaction mutagenesis, and oligonucleotide-directed mutagenesis may be used to prepare lactoferrin polypeptide variants and fragment variants (see, e.g., Sambrook et al., supra). A bovine lactoferrin variant includes a polypeptide that has at least 85%, 90%, 95%, or 99% amino acid sequence identity to any of the exemplary bovine lactoferrin amino acid sequences known in the art and/or provided in the sequence listing. Similarly, a human lactoferrin variant includes a polypeptide that has at least 85%, 90%, 95%, or 99% amino acid sequence identity to any of the exemplary human lactoferrin amino acid sequences known in the art and/or provided in the sequence listing.

Given the description in the art regarding regions of lactoferrin that exhibit particular activities (e.g., the N-terminal region comprising anti-microbial activity) and the amino acids that are the ligands for binding to FeIII (see, e.g., Baker et al., *Biochem. Cell Biol.,* 2002, supra; see also, e.g., Chapple, *Antimicrob. Agents Chemother.* 48:2190-98 (2004); Shimazaki et al., *J. Dairy Sci.* 81:2841-49 (1998); Tanaka et al., *Biochem. Cell Biol.* 81:349-54 (2003); Nakamura et al., *Protein Expression and Purification* 21:424-31 (2001); Chapple et al., *Adv. Exp. Med. Biol.* 443:215-20 (1998)), persons skilled in the art can readily determine which regions of lactoferrin may be more amenable to alteration (i.e., substitution, deletion, or addition of one or more amino acids) and which regions may not be amenable to change. Also given the description herein and given the many molecular biology, protein expression, and protein isolation techniques and methods routinely practiced in the art for introducing mutations in a polypeptide, preparing polypeptide fragments, isolating the fragments and variants, and analyzing same, lactoferrin variants and fragments having the desired biological activities can be made readily and without undue experimentation.

Assays for assessing whether the lactoferrin variant folds into a conformation comparable to the non-variant polypeptide or fragment include, for example, the ability of the protein to react with mono- or polyclonal antibodies that are specific for native or unfolded epitopes, the retention of ligand-binding functions, and the sensitivity or resistance of the mutant protein to digestion with proteases (see Sambrook et al., supra). Lactoferrin variants as described herein can be identified, characterized, and/or made according to these methods described herein or other methods known in the art, which are routinely practiced by persons skilled in the art.

Lactoferrin polypeptides, variants and fragments thereof, can be prepared without altering the biological activity of the resulting protein molecule (i.e., without altering one or more functional activities in a statistically significant or biologically significant manner). For example, such substitutions are generally made by interchanging within the groups of polar residues, charged residues, hydrophobic residues, small residues, and the like. The effect of any amino acid substitution may be determined empirically merely by testing the resulting modified protein for the ability to function in a biological assay, or to bind to a cognate ligand or target molecule. By way of example, the capability of the lactoferrin variant or fragment to bind iron, exhibit antimicrobial activity, and/or exhibit anti-inflammatory activity can be determined according to methods practiced by a person skilled in the art.

Lactoferrin, a variant or fragment thereof, may be included in a composition comprising a mineral salt (e.g., zinc gluconate) and a sulfonic acid (e.g., taurine) by combining all three components and, optionally, other agents as described herein. Alternatively, lactoferrin, a variant or fragment thereof, may be administered in a separate composition and administered prior to, concurrent with, or subsequent to administration of a composition comprising a mineral salt and a sulfonic acid (also referred to as coordinate administration). A composition comprising lactoferrin may be administered topically or systemically, or administered both topically (e.g., to a mucosal membrane, for example, orally or vaginally) and systemically at the same time or at varying times. Accordingly, in certain embodiments, a composition comprising a mineral salt, sulfonic acid, and lactoferrin (or a variant or fragment thereof) may be administered locally (e.g., to a mucosal surface, for example, oral or vaginal mucosa). In other embodiments, methods comprise administering a separate physiologically acceptable composition comprising lactoferrin (or a variant or fragment thereof) and one or more physiologically acceptable carriers (or excipients) and that lacks a mineral salt and a sulfonic acid, which is administered sequentially (either prior to or after) or concurrently with administration of a physiologically acceptable composition comprising a mineral salt and a sulfonic acid, which composition may, but not necessarily, also comprise lactoferrin. When two separate compositions are administered, the compositions may be in the same form (i.e., solid, liquid, spray, gel, past, emulsion, ointment, or foam or other form) or a different form. The two compositions may be delivered in the same or different manner, such as by lozenge, gel cap, suppository, sponge, or by another delivery vehicle described herein or with which a person skilled in the art is familiar.

In one embodiment, methods provided herein for treating a mucosal disease or disorder comprise administering a first composition that is a physiologically acceptable composition comprising a mineral salt (e.g., zinc gluconate) and a sulfonic acid (e.g., taurine) and administering a second composition comprising lactoferrin in the absence of (i.e., that lacks) each of a mineral salt and a sulfonic acid. The second composition may be administered prior to, concurrent with, or subsequent to administration of the first composition. In one particular embodiment, the first composition (i.e., comprising a mineral salt and a sulfonic acid) is administered topically to the tissue to be treated (e.g., administered topically to the oral mucosa, vaginal mucosa, or anal mucosa) and the second composition (i.e., comprising lactoferrin) is administered orally, which may have a topical effect as well as a systemic effect. In another particular embodiment, the first composition comprises a mineral salt (e.g., zinc gluconate) and a sulfonic acid (e.g., taurine) and lactoferrin. In certain embodiments, the first composition comprising the mineral salt and sulfonic acid is in the form of a gel and the second composition comprising lactoferrin is in a form appropriate for oral administration (which are described herein and known in the art).

Lactoferrin may be formulated according to well known methodologies in a composition described herein or in a separate composition for administration. Any physiological or pharmaceutically suitable excipient or carrier known to those of ordinary skill in the art for use in pharmaceutical compositions may be employed in the compositions described herein that comprise lactoferrin. Excipients for therapeutic use are well known, and are described, for example, in *Remington: The Science and Practice of Pharmacy* (Gennaro, 21$^{st}$ Ed. Mack Pub. Co., Easton, Pa. (2005)). For example, saline and phosphate-buffered saline at physiological pH may be used. Preservatives, stabilizers, dyes and even flavoring agents may be provided in the composition. For example, sodium benzoate, sorbic acid and esters of p-hydroxybenzoic acid may be added as preservatives. In addition, antioxidants and suspending agents may be used. An injectable pharmaceutical composition is preferably sterile.

An optimal dose of lactoferrin may generally be determined using experimental models and/or clinical trials. The optimal dose may depend upon the body mass, weight, or blood volume of the patient. Results of animal studies with lactoferrin have indicated that lactoferrin is well tolerated with minimum toxic effects at doses of 2000 mg/kg/day (see, e.g., Yamauchi et al., *Food Chem. Toxicol.* 38:503-12 (2000)). In certain embodiments of the methods provided herein, lactoferrin may be administered from about 5 to 50 mg lactoferrin per day, from about 50 to 400 mg lactoferrin per day, from about 400 to 1000 mg per day, from about 1 gram to 5 grams per day, or from about 5 grams to 10 grams per day, or from about 10 to about 15 grams per day, which may be administered in one or in multiple doses. The use of the minimum dosage that is sufficient to provide effective therapy is usually preferred. Patients may generally be monitored for therapeutic or prophylactic effectiveness using any one or more of observations, physical examination, clinical history, hematological profile, immunological assays and/or any other methods and techniques suitable for assessing a patient who has the condition being treated or prevented, which methods and techniques will be familiar to those having ordinary skill in the art.

The compositions described herein that comprise one or more mineral salts (e.g., zinc gluconate) and a sulfonic acid (e.g., taurine) may be in any form that allows for the composition to be administered to a subject. For example, the composition may be in the form of a solid, liquid, emulsion, ointment, suspension, gel, or gas (aerosol). A gel may also be referred to herein and in the art as a medical device or device. For example, a composition may be in the form of a device that is a gel and that comprises a mineral salt (e.g., zinc gluconate), a sulfonic acid (e.g., taurine), and one or more agents described in detail herein, such as hyaluronic acid and polyvinylpyrrolidone (PVP). As used herein, a device that is a gel may be used for treating a vaginal mucosal disorder, such as vaginal dryness and atrophic vaginitis, and may be applied intravaginally. The composition may also be embedded or impregnated in a separate device, such as a sponge. Typical routes of administration include, without limitation, oral, topical, parenteral, sublingually or buccally, rectal, vaginal, or intranasal. The term parenteral as used herein includes subcutaneous injection, intravenous, intramuscular, intrasternal, intracavernous, intrathecal, intrameatal, intraurethral injection, or infusion techniques. A composition is formulated in a manner that allows the active ingredients contained therein to be bioavailable upon administration of the composition to a subject. Compositions that will be administered to a subject may be prepared in a form that comprises one or more dosage units. For example, a tablet may be a single dosage unit, and a container (e.g., a bottle or ampoule) comprising a composition described herein may contain a plurality of dosage units.

As described herein, for oral administration, an excipient and/or binder may be present. Exemplary excipients include sucrose, kaolin, glycerin, starch dextrins, sodium alginate, carboxymethylcellulose and ethyl cellulose. Coloring and/or flavoring agents may also be present. A coating shell may be employed.

The composition may be in the form of a liquid, e.g., an elixir, syrup, solution, emulsion or suspension. The liquid may be for oral administration or for delivery by injection (or infusion), as two examples. When intended for oral administration, and as described in detail herein, compositions may further comprise, in addition to one or more mineral salt (e.g., zinc gluconate) and a sulfonic acid (e.g., taurine), at least one of sweetening agent, a preservative, a dye/colorant, a flavor enhancer, a surfactant, a preservative, a wetting agent, a dispersing agent, a suspending agent, a buffer, a viscosity enhancing or a thickening agent, a stabilizer, and an isotonic agent.

A liquid composition as used herein, whether in the form of a solution, suspension or other form, may include one or more of the following excipients: sterile diluents such as water for injection, saline solution, preferably physiological saline, Ringer's solution, isotonic sodium chloride, fixed oils such as synthetic mono or digylcerides that may serve as the solvent or suspending medium, polyethylene glycols, glycerin, propylene glycol or other solvents; antioxidants such as ascorbic acid or sodium bisulfite; chelating agents such as ethylenediaminetetraacetic (EDTA) acid; buffers such as acetates, citrates or phosphates and agents for the adjustment of tonicity such as sodium chloride or dextrose. The composition can be enclosed in ampoules, disposable syringes, bottles or multiple dose vials made of glass or plastic. In certain embodiments, the composition may comprise antimicrobial agents such as benzyl alcohol or methylparaben that act as preservatives (i.e., prevent growth in the composition of any microorganism that may contaminate or be unintentionally introduced into the composition).

The compositions described herein that comprise a mineral salt (e.g., zinc gluconate) and a sulfonic acid (e.g., taurine) (which may be formulated with one or more mucosal delivery-enhancing agents as described herein), may be delivered at a dose and for a time sufficient to treat a dermal or mucosal disease or disorder. A dose release may be substantially normalized and/or sustained for an effective delivery period ranging from 0.001 to 1.0 hours, from 0.001 to 0.01 hours, from 0.025 to 0.05 hours, from 0.01 to 0.05 hours, from 0.1 to 2.0 hours; from 0.4 to 1.5 hours; from 0.7 to 0.5 hours; or from 0.8 to 1.0 hours. In some methods of administration, the delivery period may be from many hours or days as necessary to provide benefit to the subject. A composition disclosed herein can be administered once a day, or multiple times a day (e.g., twice, three, four, or five times a day), once every other day, once weekly, once biweekly, or once a month as necessary to treat or prevent, or modulate the appearance of a symptom of, or otherwise improve the outcome of a mucosal or dermal disorder. Administration of a composition disclosed herein can begin prior to the initiation or detection of symptoms of a dermal or mucosal disease, disorder, or condition, or prior to initiation or detection of associated or related inflammation. By way of example, prior to a first administration of chemotherapy or radiotherapy that is expected to have a side effect such as oral mucositis, the compositions described herein may be administered to the subject. Alternatively, the compositions described herein may be administered after chemotherapy or radiotherapy treatment but before initiation of a symptom of oral mucositis, or administration can begin after a symptom of oral mucositis (or oral stomatitis) is detected.

A composition described herein for the treatment of vaginal mucosal disorders, diseases, and conditions, including but not limited to vaginal dryness and atrophic vaginitis, may be administered daily, weekly or bi-weekly, or otherwise over a suitable period of time, for example, for ten, twenty, thirty, thirty-five or more days (e.g., 12 weeks). Such treatment may continue until one or more of the following occur: vaginal epithelial thickness increases (relative to epithelial thickness prior to initiating treatment); the maturation index increases (relative to maturation index prior to initiating treatment); in vaginal pH decreases (relative to pH prior to initiating treatment); the severity of a bothersome symptom (e.g., vaginal dryness, vaginal irritation/itching, vaginal soreness, difficulty passing urine, frequent urination, pain during intercourse, or bleeding after intercourse) decreases relative to the same prior to initiating treatment.

As described in greater detail herein, Pap smears may be performed and the number of parabasal, intermediate and superficial cells may be counted, and the percentage of each cell type calculated in order to determine a Maturation Index. A maturation index represents the degree of proliferation and maturation of, for example, vaginal cells. A maturation index may be reported as a percentage of parabasal, intermediate, and superficial cells as determined by calculations known in the art. For example, the percentages may then be used in the following equation to determine a Maturation Index=(% Parabasal cells×0)+(% Intermediate cells×0.5)+(% Superficial cells×1.0).

Dermal and Mucosal Diseases, Disorders, and Conditions and Treatment Thereof

Methods are provided herein for treating dermal and mucosal diseases, disorders, and conditions, and include inflammatory mucosal diseases (e.g., mucositis and atrophic vaginitis) and disorders and conditions. Mucositis refers to inflammation and ulceration of a mucous membrane and may occur at one or more mucosal sites located at a mucosal surface of the oral cavity (or oropharyngeal cavity), gastrointestinal tract, vagina, bladder, rectum, anus, lung, esophagus, mucosal surface of the nasal cavity, ear, and ocular mucosa. In one specific embodiment, methods are provided herein for treating and/or preventing mucositis that comprises oral mucositis or oral stomatitis by administering the compositions described herein. In another specific embodiment, the mucosal disorder prevented or treated by the methods described herein includes atrophic vaginitis, vaginal dryness, vaginal burning, vaginal ulceration, vulvar burning), dyspareunia, leukorrhea, and vulvar pruritus. In other certain embodiments, the mucosal disorder comprises an oral ulceration, inflammatory bowel disease (including Crohn's disease and ulcerative colitis), periodontitis, interstitial cystitis, and a wound. In still other embodiments, the methods provided herein are useful for treating and/or preventing a dermal disease, disorder, or condition, including but not limited to eczema, psoriasis, xerosis, erythema, radical oxygen species-induced skin damage, and other dermal diseases, conditions, and disorders, including other inflammatory dermal disorders. In certain embodiments, the mucosal disorder treatable by the methods and compositions described herein is consequent to any one or more of hormone insufficiency, bone marrow transplant, chemotherapy, radiation therapy, viral infection, fungal infection, and bacterial infection. In a particular embodiment, the mucosal disorder results from or is associated with either one or both of chemotherapy and radiation therapy for treatment of a head and neck tumor, Kaposi's sarcoma, a leukemia, breast cancer, prostate cancer, pancreatic cancer, ovarian cancer, melanoma, liver cancer, lung cancer, urinary cancer, and/or colon cancer. In other specific embodiments, the methods described herein may be used for treating hormone insufficiency, which in particular embodiments is estrogen insufficiency that is consequent to, associated with, or results from perimenopause or menopause.

Oral mucositis may be initiated by the cytotoxic effects of chemotherapy and/or radiotherapy on the rapidly dividing epithelial cells of the oropharyngeal mucosa, which is exacerbated by infection with both endogenous oral flora and opportunistic bacterial and fungal pathogens. Complications related to oral mucositis vary in the different patient populations affected, but include pain, poor oral intake with consequent dehydration and weight loss, and systemic infection with organisms originating in the oral cavity (Sonis, 1993b, supra). The pain associated with oral mucositis may be severe requiring narcotic analgesics, and difficulty in eating can result in patients receiving total parenteral nutrition. The damaged oral epithelium of the oral mucosa and defective immune response often found in these patients offers a ready route for entry of organisms from the mouth into the systemic circulation, and the potential for sepsis. Due to these complications, oral mucositis can be a direct dose-limiting toxicity of radiation or chemotherapy treatment, thereby resulting in an inadequate cancer therapy.

Therapies used for treating tumors as well as the very aggressive chemotherapy protocols used in bone marrow transplant are associated with a high incidence of oral mucositis. Younger patients seem to have an even higher incidence, which may be due to their more rapid epithelial cell turnover and hence susceptibility to cytotoxic drugs (Sonis 1993a, supra). Incidence of oral mucositis is also related to the choice of chemotherapeutic agent, with commonly used chemotherapeutic agents such as carmustine (BCNU), chlorambucil (LEUKERAN), cisplatin (PLATINOL), cytarabine, doxorubicin (ADRIAMYCIN), fluorouracil (5-FU), methoxetrate (MEXATE) and plicamycin (MITHRACIN) being known for their direct stomatotoxic potential (Sonis, 1993b, supra). The likelihood that a patient receiving chemotherapy or radiotherapy will develop mucositis is increased in patients who smoke, have poor oral or dental health, use chewing tobacco, drink alcohol, are dehydrated, and are suffering from underlying diseases such as kidney disease, diabetes, or HIV/AIDS.

Localized topical application of agents that may be used to treat oral disorders of mucosal epithelia such as oral mucositis presents unique problems. For example, due to salivation and/or food or fluid intake, oftentimes sufficient mucoadhesion and residence time in the mouth may be difficult to attain for the agent to be effective. Other difficulties associated with topical oral application of drugs include tooth discoloration and patient compliance. The oral formulations of the compositions described herein provide good mucoadhesion and residence time in the mouth, while at the same time providing high levels of patient compliance.

Provided herein are methods for treating a mucosal disorder such as oral mucositis comprising administering compositions that comprise a mineral salt such as a zinc salt (e.g., zinc gluconate) and a sulfonic acid (e.g., taurine) that may result in broad spectrum reduction in mucositis (including reducing production of inflammatory cytokines and reducing inflammation), antimicrobial activity, reduction of pain, good stability, mucoadhesion and residence time in the mouth, and high levels of patient compliance. As a consequence of administering the compositions described herein for treating oral mucositis, which may decrease inflammation and promote restoration and healing of the mucous membrane including minimizing or inhibiting occurrence of microlesions and ulceration, the susceptibility of the mucous membrane to invasion and colonization by microorganisms (such as *Candida albicans* (causative agent of thrush)) may be decreased, thus preventing or decreasing the likelihood of microbial infection, and/or decreasing the recurrence and frequency of microbial infections.

Oral or gastrointestinal mucositis is a painful inflammation and ulceration of a mucous membrane lining the digestive tract. The pathophysiology of mucositis can be divided into 5 stages, including an initiation phase, a message generation phase, a signaling and amplification phase, an ulceration phase, and a healing phase. The initiation phase is often associated with the production of free radicals (caused by chemotherapy or radiotherapy, for example), which damage the DNA of cells and upregulate inflammatory cytokines. At the time when inflammatory cytokines are upregulated marks the beginning of the ulceration phase. The healing phase involves the movement of epithelial cells to the site of the ulcer and the initiation of reepithelialization of the ulcer. The methods described herein may be used for treating (prophylactically or therapeutically) any one or a combination of the pathophysiological stages of mucositis, including oral mucositis, in a subject having or likely to have mucositis or stomatitis (including intestinal cystitis).

Oral stomatitis is an inflammation of the mucous lining of the structures of the mouth, including the cheeks, gums, tongue, lips, throat, and roof or floor of the mouth. Stomatitis may be caused by poor oral hygiene, poorly fitted dentures, or from mouth burns from hot food or drinks, medications, allergic reactions, radiation therapy, or infections. Iron deficiency anemia can also lead to stomatitis, including irritation and fissuring in the corners of the lips (e.g., angular stomatitis or angular cheilitis).

Subjects with cancer (i.e., a malignancy) usually display symptoms of mucositis (or stomatitis) four or five days after beginning treatment (e.g., chemotherapy), reaching a peak at about day 10 and slowly improving over the course of a few weeks. Mucositis associated with administration of radiotherapy usually appears at the end of the second week of treatment and may last for six to eight weeks. Furthermore, recovery from mucositis may be slowed and complicated by infection with one or more opportunistic viruses, bacteria, or fungi that infect the sores or ulcerations that are symptomatic of mucositis. A loss of taste perception (as a result of mucositis) often makes eating more difficult for a patient, which, in turn, leads to weight loss. Thus, in certain embodiments, methods are provided for preventing, delaying the onset of, reducing the duration of, or otherwise treating oral mucositis by administering the compositions described herein.

Treatment of oral mucositis or oral stomatis, and any associated or related inflammation, may be monitored throughout the treatment regimen and may be evaluated at the end of treatment by determining quantity of food and liquid intake by the subject, weight loss or gain, evaluating pain, which may be determined subjectively as well as objectively, for example, by monitoring use of need for analgesics, including over the counter medications and narcotics. Healing of tissue may be evaluated by a clinical provider during the course of treatment according to methods and standards in the medical art.

In other embodiments, methods are provided for treating or preventing atrophic vaginitis that includes an inflammation of the vagina, sometimes extending to the outer urinary tract, which may be associated with a thinning or shrinking of mucosal tissues or associated epithelial layers. A decrease in vaginal lubrication (i.e., vaginal dryness) is often associated with atrophic vaginitis.

Any one or more of a variety of causes (e.g., postmenopausal estrogen reduction) may lead to the progressive development of atrophic vaginitis. Throughout a woman's life cycle, the vaginal epithelium undergoes changes in response to the level of circulating estrogen. Stimulated by maternal estrogen, the vaginal epithelium is rugated and rich in glycogen in the newborn. During childhood, the epithelium remains thin until puberty, when it again thickens as a result of estrogen stimulation. After menopause, circulating estrogen levels (mainly estradiol) are dramatically reduced from greater than 120 pg per ml to about 18 pg per ml. Postmenopausal women may present numerous cytologic transformations follow estrogen reduction, including proliferation of connective tissue, fragmentation of elastin, and hyalinization of collagen. These changes may result in granulation, fissures, ecchymoses, telangiectases and ulcerations of the vaginal mucosa (Rigg L. A., *Int. J. Fertil.* 31:29-34, 1986). Postmenopausal changes in tissue composition are not limited to the genital tract but also include the urinary tract because of the shared common embryologic origin. Therefore, both vaginal and urethral epithelia of associated mucosa are estrogen dependent and adversely changed in an estrogen-deprived environment.

Menopause is a leading cause of decreased levels of circulating estrogen and is commonly associated with atrophic vaginitis. A long-term decrease in estrogen stimulation is often required before symptoms of atrophic vaginitis arise, an early sign of which is a decrease in vaginal lubrication. However, even in nonmenopausal women, production of ovarian estrogen can be interrupted by radiation therapy, chemotherapy, immunologic disorders, and oophorectomy. Side effects of antiestrogen medications, such as medroxyprogesterone (PROVERA), tamoxifen (NOLVADEX), danazol (DANOCRINE), leuprolide (LUPRON), and nafarelin (SYNAREL), are also implicated as causes of atrophic vaginitis (Beard. *Postgrad. Med.* 91:257-60, 1992). An increase in the severity of symptoms occurs in women who are naturally premenopausally estrogen deficient, smoke cigarettes, have not given birth vaginally, receive radiotherapy or chemotherapy or other medications described herein, have an immune disorder, have had the ovaries removed, after pregnancy, lactating, or who exhibit nonfluctuating levels of estrogen (Pandit et al., *Am. J. Med. Sci.* 314:228-31, 1997; Kalogeraki et al., *In Vivo* 10:597-600, 1996; Dupont et al., *Maturitas* 13:297-311, 1991). Milder atrophy occurs in postmenopausal women who participate in coitus, have higher androgen levels, and have not undergone vaginal surgery (Pandit et al., supra; Beard, supra; Kalogeraki, supra; Dupont et al., supra; Leiblum et al., *JAMA* 249:2159-98, 1983). In addition, many younger women and those in perimenopause (i.e., the menopausal transitional period) may also experience periodic vaginal dryness and associated problems.

Postmenopausal genital symptoms include dryness, burning, dyspareunia, loss of vaginal secretions, leukorrhea, vulvar pruritus, feeling of pressure, itching and yellow malodorous discharge (Pandit et al., supra; Beard, supra; Mettler et al., *Maturitas* 14:23-31, 1991). Urinary symptoms of urethral discomfort, frequency, hematuria, urinary tract infection, dysuria, and stress incontinence may be presenting symptoms of atrophic vaginitis (Pandit et al., supra; Beard, supra; Bachmann, *Maturitas* 22(Suppl):S1-5, 1995; Mettler et al., supra). Furthermore, many if not all symptoms of atrophic vaginitis can be exacerbated by a simultaneous infection of candidiasis, trichomoniasis or bacterial vaginosis.

As the life expectancy of women increases, the impact of vaginal dryness (which may precede as well as be a symptom of or condition associated with atrophic vaginosis) on quality of life, sexual functioning, and urogynecologic health is becoming more evident in the day-to-day practice of medicine. Because women's life expectancy is increasing, insult to the vaginal mucosa also increases (e.g., vaginitis/vaginosis and exposure to medications treating these conditions). In addition, the number of routine physical examinations performed throughout a woman's life increase as well, which can result in traumatization of vaginal mucosa during digital or pelvic examination because of vaginal dryness. Petechiae or small hemorrhages on the vaginal lining and evidence of vaginal micro-lesions may also be observed. In addition, the vaginal introitus may be narrowed; the epithelial surface (of the vaginal mucosa) is typically very friable and may be ulcerated (Rigg, *Int. J. Fertil.* 31:29-34, 1986).

A decrease in estrogen (estrogen insufficiency) associated with post-menopausal women is a significant cause of atrophic vaginitis. However, premenopausal women may also experience significant discomfort associated with atrophic vaginitis, which can be initiated as a side effect of radiotherapy or chemotherapy, immune disorder, removal of ovaries, after pregnancy, during lactation, or because of consumption of various medications such as TOMOXAFEN, DANAZOL, MEDROXYPROGESTERONE, LEUPROLIDE, and NAFARELIN. A decline in estrogen can cause a reduction of tissue mass, thus increasing or contributing to declining health of the vaginal tissue, which increases the likelihood that microlesions will develop, which in turn, increase the susceptibility to microbial infection. Presently available treatments received by women with declining estrogen may exacerbate the declining integrity of vaginal tissue and contribute to a cycle of declining vaginal health. The conditions of atrophic vaginitis can be further exacerbated by opportunistic infection by Gram-positive aerobic microorganisms, Gram-negative aerobic micro-organisms. Gram-positive anaerobic microorganisms, and Gram-negative anaerobic microorganisms in the vaginal tract of pregnant and non-pregnant women. Atrophic vaginitis is particularly exacerbated in Gram-positive aerobic vaginitis caused by group B streptococci (*Streptococcus agalactiae*).

The symptoms of atrophic vaginitis include vaginal soreness, itching, painful intercourse and bleeding after intercourse, and varying degrees of ulceration. Atrophic vaginitis is often associated with a reduction in epithelial thickness of the vaginal mucosa. Urinary symptoms of atrophic vaginitis include painful urination, increased frequency, blood in urine, incontinence, and an increase likelihood of microbial infection, which may result from a change in vaginal pH.

Thus, in certain embodiments, methods are provided for preventing, delaying the onset of, reducing the duration of, or otherwise treating atrophic vaginitis by administering the compositions described herein. As a consequence of administering the compositions described herein for treating atrophic vaginitis, which may decrease inflammation and promote restoration and healing of the urogenital mucous membrane including minimizing or inhibiting ulceration, the susceptibility of the mucous membrane to invasion and colonization by microorganisms may be decreased, thus preventing or decreasing the likelihood of microbial infection, and/or decreasing the recurrence and frequency of vaginal infections, including yeast infections, bacterial vaginosis, aerobic vaginitis, and trichomonas.

The methods provided herein may be useful for treating any one or more of the conditions that may, but not necessarily, precede, indicate a predisposition to developing atrophic vaginitis, are associated with or a symptom of atrophic vaginitis, or result from or are consequent to atrophic vaginitis. In certain embodiments, methods are provided for preventing, delaying the onset of, reducing the duration of, reducing recurrence of, or otherwise treating any one or more of genital dryness, itching, and burning (e.g., vaginal dryness, vaginal burning, vaginal ulceration, vulvar burning), dyspareunia, leukorrhea, and vulvar pruritus by administering the compositions described herein comprising a mineral salt and a sulfonic acid. The compositions described herein may also be administered to maintain the pH of the vagina, which is normally an acid pH (e.g., between pH 3.5 and 5) or to reduce the pH of the vagina if the vaginal pH is greater than the pH considered normal vaginal pH. The methods described herein are also useful for treating these conditions when the etiology is unrelated to atrophic vaginitis. Administration of the compositions described herein over a period of time may thus, in general, improve and maintain the health of the vaginal mucosa.

Without wishing to be bound by theory, methods described herein comprising administering a composition comprising a mineral salt of zinc and a sulfonic acid for the prevention or treatment of mucosal disorders, such as oral mucositis or atrophic vaginitis, may relate to a capability of the composition to down regulate proinflammatory cytokines associated with these disorders or conditions. For example, Mainnemare et al. (*J. Dent. Res.* 83(11): 823-831, 2004) found that intracellular taurine-N-monochloramine (TauCl) in combination with hypochlorous acid (HOCl) appears to play a crucial role in the periodontal inflammatory process by neutralizing IL-6 and several metalloproteinases. Gurujeyalakshmi et al. (*J. Pharmacol. Exp. Ther.* 293:82-9, 2000) reported that taurine and niacin blocked lung injury and fibrosis by down-regulating bleomycin-induced activation of NF-kB in mice. Taurine and niacin attenuated the induced proinflammatory cytokines IL-1α, TNFα, IL-6 and TGFβ. However, neither of Mainnemare et al. or Gurujeyalakshmi et al. describe topically applying a composition comprising a mineral salt (e.g., zinc gluconate) and a sulfonic acid (e.g., taurine) in the treatment of a mucosal disorder such as oral mucositis or atrophic vaginitis.

In a large study of 631 women in prenatal care. Donder et al. (BJOG 109: 34-43, 2002) defined a new class of abnormal vaginal flora that is distinct from bacterial vaginosis: aerobic vaginitis. Unlike bacterial vaginosis, aerobic vaginitis, characterized by group B streptococci and *E. coli* aerobic microorganisms results in a host immune response that leads to the production of IL-6, IL-1β and leukemia inhibitory factor in vaginal fluid. Donder et al. suggest that aerobic vaginitis may be a better candidate than bacterial vaginosis as the cause of pregnancy complications and preterm delivery.

Döderlein's lactobacilli depend on glycogen from sloughed vaginal cells (Pandit et al., *Am. J. Med. Sci.* 314:228-31, 1997), which in turn produce lactic acid and thereby lower vaginal pH levels to between 3.5 and 4.5. A vaginal pH from about 3.5 to 4.5 is essential for the body's natural defense against vaginal and urinary tract infections (Semmens et al., *JAMA* 248:445-48, 1982). Increased vaginal pH levels predispose the vagina to bacterial infection by streptococci, staphylococci, coliforms and diphtheroid (Pandit et al., supra). In fact, vaginal pH is typically greater than 5.0 in patients with atrophic vaginitis due to opportunistic bacterial infections. Thus, the methods provided herein for preventing, delaying the onset of, reducing the duration of, or otherwise treating vaginitis, vaginosis, and atrophic vaginitis by administering the compositions described herein that are formulated at an acid pH, such as between 3.5 and 4.5, may provide benefit to affected subjects in need of such treatment.

In other embodiments, compositions described herein may be used in methods for treating skin irritations (e.g., itching and dry skin), treating skin (i.e., dermal) wounds, dermatitis, eczema, and psoriasis. In still other embodiments, a composition comprising a mineral salt (e.g., zinc gluconate) and a sulfonic acid (e.g., taurine) may be administered topically in a method for treating a subject with a dermal disorder (e.g., a surface epithelium). Such a disorder of a surface epithelium includes damage caused by burning (e.g., chemical, electrical, radioactive or thermal burning). Thermal burning may result from exposure to a flame, hot object, or to steam or a hot liquid, for example. In still other embodiments, the methods described herein may be used for topical application to skin to reduce or decrease discomfort and/or to reduce decrease visual size and/or color of varicose veins.

In still other embodiments, compositions described herein may be used in methods for treating a mucosal disorder resulting from the treatment (e.g., chemotherapy or radiation therapy) of a malignancy. In still another embodiment, compositions described herein may be used in methods for treating a dermal disorder (also referred to as a skin disorder), which includes a chronic skin disorder. Exemplary dermal disorders treatable with the compositions described herein include, but are not limited to, diaper rash, skin dryness, dermatitis, eczema, psoriasis, erythema, acne, and xerosis, and other dermal diseases, conditions, and disorders, including other inflammatory dermal disorders. The methods and compositions described herein are thus useful for promoting normal epithelial cell growth and healing of dermal tissue, and which reduce colonization and infection by microorganisms, such as bacteria, viruses, fungus, and yeast.

The methods and compositions described herein may also be useful for treating tissue and cell damage caused by reactive oxygen species in mammals, including humans. Free radicals such as superoxide ions, hydroxy radicals, and oxides are known as a major factor of degeneration and thus the ageing of the skin (see, e.g., U.S. Pat. No. 6,462,067). These free radicals effect destruction of the proteins and lipids of the cellular membrane, affect the DNA, and also cause decomposition of hyaluronic acid, a key substance of the skin. Under normal biological conditions an equilibrium ratio exists between generation of free radicals and their removal from a cell by endogenous chemical or enzymatic systems. Additional outside environmental stress factors such as pollution, tobacco smoke, and ultraviolet radiation, for example, may overload these inherent immune systems and shift the equilibrium in favor of the free radicals. Inflammation or ageing phenomena of the skin may occur. Among principal enzymes that have an effect on aging process, catalase, glutathione peroxidase, ascorbate peroxidase, and superoxide dismutase are most important. The enhancement of superoxide dismutase (SOD) activity as a method to control various human ailments including aging has been studied extensively, for example, by Dugas et al. (U.S. Pat. No. 6,426,068), Anggard et al. (U.S. Pat. No. 6,455,542), Hellstrand et al. (U.S. Pat. Nos. 6,462,067; 6,407,133). Golz-Berner et al. (U.S. Pat. No. 6,426,080), and others. Approaches for treating skin conditions related to oxygen radical tissue damage include design of low-molecular weight SOD mimics (synzymes) that would mimic the natural SOD enzyme in removing superoxide radical anion. [O2-.], and the perhydroxyl radical, [HO2.], as well as preventing formation of peroxynitrite anion, [ONO2-.]. The methods described herein provide an alternative method for treating oxygen radical species-induced skin and tissue damage, by administering a composition comprising a mineral salt and a sulfonic acid, which are considered safe to administer to a human subject.

In other embodiments, the compositions described herein for treating or preventing a dermal disorder may also be considered to have cosmetic use. The compositions described herein may be used as effective inhibitors of UV rays in topical sunscreens, and in treating dandruff and other scalp conditions. In still other embodiments, the compositions described herein may be used in preventing or treating diaper rash and skin dryness. As exemplified herein, cosmetic uses of a composition comprising a mineral salt (e.g., zinc gluconate) and a sulfonic acid (e.g., taurine) may be suitable in particular shampoos, scalp creams, deodorizing body-cleansing compositions, care compositions and emulsions. In addition, a composition described herein may be used in hair rinses, hair treatments, hair regeneration products, hair tonics, blow-drying lotions, hairsprays, styling creams, styling gels, hair oils, hair pomades, products modulating hair brilliance, shower preparations, soaps, liquid soaps, deodorant sticks, deodorant spray, emulsions. Products comprising a composition described herein may applied transiently (i.e., for a short period of time) or applied for a longer period of time (e.g., as a leave-in or leave-on hair care product). Additional cosmetic uses include foot sprays or creams, antibacterial face washes, and body lotions.

In certain other embodiments, methods are provided for treating a viral infection. In one embodiment, the virus causing the infection is a herpes simplex virus. In another embodiment, methods are provided for treating a viral infection such as caused by herpes zoster that is characterized by painful rash and blisters. Zinc salts irreversibly inhibit herpes virus replication in vitro and are effective in treating herpes infections in vivo. Herpes of the lips occurs in 50% of the population, and genital herpes is one of the most common sexually transmitted diseases. Zinc ions irreversibly inhibit herpes simplex virus (HSV) glycoprotein functions by accumulating in the sulfhydryl groups of glycoprotein B in the viral membrane, blocking synthesis of DNA. In the closely related rhinovirus, research scientists have theorized that free zinc ions may sequester in the membrane, inhibiting viral binding with ICAM receptor sites in mucous membranes.

The genome and encoded polypeptides of Herpes simplex virus (HSV) share significant homology with Varicella-Zoster virus (VSV) (a pox virus). Varicella-Zoster virus is the cause of chickenpox and shingles. Eruptions of herpes zoster associated with shingles are thought to be more frequent in the elderly not because of immune dysfunction, but because of slowed mobilization of the immune system. Prompt treatment with the compositions described herein may be beneficial by decreasing the viral load and reducing painful lesions independent of immune system activation. Moreover, the compositions described herein provide an alternative therapy that is less expensive than current standard of care (administration of an anti-viral such as acyclovir, valacylovir, and famciclovir with or without a steroid), and that has more than a palliative effect such as use of calamine lotion. In certain embodiments, the methods provided herein for treating or preventing a viral infection, such as an infection caused by Herpes Simplex Virus or Varicella zoster virus, comprise administering a composition comprising a mineral salt (e.g., zinc gluconate) and a sulfonic acid (e.g., taurine) and an amino acid; in certain particular embodiments, the amino acid is lysine.

In certain other embodiments, methods are provided herein for supplementing a mineral deficiency in a subject, that is, treating a subject who has a mineral insufficiency or deficiency or who is in need of mineral supplementation. By way of example, administration of a composition comprising a mineral required for enzyme function, for example, zinc, may promote healing by providing the mineral to the cells of the tissue such that enzymes, cofactors, and other cellular substituents that require the mineral may properly function. In one embodiment, a method is provided wherein the method comprises administering a composition described herein that comprises a mineral salt, a sulfonic acid, and one or more of 0.05% to 3.0% (w/w) glycyrrhetinic acid; 0.04% to 15% (w/w) polyvinylpyrrolidone (PVP); 0.01% to 5.0% (w/w) hyaluronic acid; and 0.05% to 3.0% (w/w) glycerin (or 0.05% to 5.0% (w/w) glycerin). In particular embodiments, the mineral insufficiency or deficiency is related to lower than normal levels (i.e., a normal level refers to the level or amount of a mineral that is available for normal cellular and biological function in the absence of disease or dysfunction) of any one or more of zinc, calcium, magnesium, manganese, cobalt, chromium, selenium, vanadium, copper, iron, nickel, silicon, boron, arsenic, molybdenum, sodium, potassium, phosphorus, sulfur, chlorine, fluorine, iodine, and lithium. In certain other embodiments, the mineral moiety of the mineral salt included in the compositions described herein is any one of zinc, calcium, iron, copper, magnesium, manganese, cobalt, chromium, selenium, and vanadium. The mineral may be in the form of a gluconate, acetate, ascorbate, or sulfate salt. In still another specific embodiment, the sulfonic acid is taurine. In a certain embodiment, methods comprise administering a composition comprising 0.25% (w/w) to 5.5% (w/w) zinc gluconate and 0.25% (w/w) to 30% (w/w) taurine. In other particular embodiments, the compositions that are useful for supplementing a mineral deficiency or treating a subject who has a mineral deficiency comprise a mineral salt (e.g., zinc gluconate), a sulfonic acid (e.g., taurine), and further comprise one or more of a flavoring agent, a mucoadhesive agent, a pH adjusting agent, a solubilizing agent, a viscosity modulating agent, and a stabilizing agent. These compositions may comprise at least one of 0.05% to 3.0% (w/w) glycyrrhetinic acid; 0.04% to 15% (w/w) polyvinylpyrrolidone (PVP); 0.01% to 5.0% (w/w) hyaluronic acid; and 0.05% to 3.0% (w/w) glycerin (or 0.05% to 5% (w/w) glycerin), and lactoferrin.

The physiologically acceptable compositions described herein may be administered in a manner appropriate to the disease to be treated (or prevented) as determined by persons skilled in the medical arts. Treatment of a subject or patient refers to the medical management of the disease, disorder, or condition (see, e.g., Stedman's Medical Dictionary). An appropriate dose and a suitable duration and frequency of administration will be determined by such factors as the condition of the patient, the type and severity of the patient's disease, the particular form of the active ingredient(s), and the method of administration. In general, an appropriate dose and treatment regimen provides the composition(s) in an amount sufficient to provide therapeutic and/or prophylactic benefit (e.g., an improved clinical outcome, such as more frequent complete or partial remissions, longer disease-free status (i.e., decreasing the likelihood or the propensity that a subject will present symptoms on the basis of which a diagnosis of a disease is made); and/or overall survival; decrease in the number of symptoms presented, or a lessening of symptom severity; decrease or abrogation of pain; improved quality of life). By way of example, treatment of mucositis may be effected, in part, by decreasing the number and/or size of lesions, reducing or decreasing the time to which one or more lesions heal, and/or reducing or eliminating associated pain, and/or by decreasing or reducing production of inflammatory cytokines and other inflammatory factors. With respect to oral mucositis, treatment may be indicated, in part, by the ability of the patient to retain or regain all or partial ability to taste food and drink. For prophylactic use, a dose should be sufficient to prevent, delay the onset of, or diminish the severity of a dermal or mucosal disease or disorder or a symptom, condition, or sequelae thereof (which includes, for example, inflammation). A "therapeutically effective amount" or "effective amount" means an amount of an active pharmaceutical ingredient, composition or formulation, or agent that is sufficient, in the subject (e.g., a mammal) in need thereof and to which it is administered, to treat (i.e., effectively manage) or prevent (i.e., decrease or reduce the likelihood of occurrence of) the stated disease, disorder, or condition.

Optimal doses may generally be determined using experimental models and/or clinical trials. The optimal dose may depend upon the body mass, weight, or blood volume of the patient. The use of the minimum dosage that is sufficient to provide effective therapy is usually preferred. Patients may generally be monitored for therapeutic or prophylactic effectiveness using assays and methods suitable for the condition being treated or prevented, which assays, methods, and techniques are discussed herein will be familiar to those having ordinary skill in the art. For subjects who receive the compositions described herein according to the methods described herein, monitoring likely includes clinical observations, personal history (e.g., to determine comfort or pain, quality of life, ability to eat and drink without discomfort or pain), and physical examination.

For example, for methods comprising administration of the compositions described herein for treating any one or more of the mucosal diseases, disorders, or conditions affecting the urogenital tract of women, particularly the vaginal mucosa, a multicenter, open, non-controlled study may be designed to evaluate safety in a composition described herein is applied vaginally to about ten women for ten, twenty, thirty, thirty-five or more days. Alternatively or in addition, a study evaluating about 100 post-menopausal women may be initiated, with vaginal application of the composition daily, weekly, or bi-weekly. An endpoint of such studies may include the level of vaginal dryness, measured according to standard methods such as a visual analogue scale. Other endpoints may include evaluation and assessment of itching, burning, dysareunia, vaginal inflammation and edema and rash may also be assessed by a four-point scale, which may include determination of vaginal abrasions and disepithelialisation.

Papanicolaon ("Pap") smears may be obtained from the upper one-third lateral vaginal wall in the routine manner for maturation index, and evaluated to determine the ratio of superficial, intermediate, and parabasal cells. As necessary, biopsy specimens may be obtained from the upper one-third of the vagina using a Kevorkian forceps after application of topical 4% lidocaine. Specimens for histology may be evaluated for epithelial thickness and the presence or absence of glycogen, which is a measure of vaginal epithelial maturation. Changes that may indicate improvement in atrophic vaginitis (e.g., vaginal epithelial thickness, maturation index, vaginal pH, or severity of bothersome self-assessed symptom(s)) can be measured or otherwise quantified over a suitable period of time (e.g., 6-12 weeks or longer). In parallel, the mean change in vaginal pH between baseline and end of treatment may be calculated by measuring the vaginal pH, for example, by inserting a standardized pH paper into the vagina and comparing the results to the manufacturer's color chart.

A maturation index of a vaginal mucosa can be measured at the beginning (baseline) and at end of treatment (patient's last visit), which is determined by counting the number of parabasal, intermediate, and superficial cells and calculating the percentage of each cell type. The percentages are then used in the following equation to determine the maturation index: Maturation Index=(% Parabasal cells×0)+(% Intermediate cells×0.5)+(% Superficial cells×1.0). The most bothersome symptoms of a patient can be identified by the patient from a list of (for example) the seven different symptoms of atrophic vaginitis measured at the baseline visit. Such symptoms include one or more of (1) vaginal dryness; (2) vaginal irritation/itching; (3) vaginal soreness; (4) difficulty passing urine; (5) frequent urination; (6) pain during intercourse; and (7) bleeding after intercourse.

Overall, a method of treating a mucosal disorder as described herein, such as atrophic vaginitis and other vaginal mucosal diseases, disorders, and conditions, is intended to be safe, tolerated, and effective. With regard to atrophic vaginitis, effectiveness includes a statistically significant increase or biologically significant increase in the maturation index or a statistically significant, clinically significant, or biologically significant decrease in vaginal pH, or reduction in the severity of a most bothersome symptom. The reduction and severity of symptoms may be determined subjectively and may be determined objectively by metrics for determining quality of life that are familiar to persons skilled in the art.

Other assays and techniques that may be used for evaluating the effect of treatment using a composition described herein include in vitro cell culture assay systems routinely practiced by persons skilled in the relevant art. For example, normal human vaginal epithelial cells, such as a cell line commercially available from Clonetics (NHVE 5164), may be subcultured in basal PrEBM (Clonetics CC 3165) using 96 well plates at 37° C., 5% $CO_2$. Cells may be exposed to medium containing various concentrations of the composition used for treatment. In parallel, appropriate controls are included, such as media of control cells that is devoid of such composition. Cell proliferation and/or viability may then be determined at various times according to methods routinely practiced in the art.

Inflammation and the inflammatory response, including cytokine induction and production can be determined by methods routinely practiced in the art. The increased or decreased level of inflammatory factors and cytokines in a biological sample obtained from the subject before, during, and or after treatment may be readily determined by methods and assays described herein and practiced routinely in the art to monitor the effect of treatment. An immune response in a host or subject may be determined by any number of well-known immunological techniques and methods with which those having ordinary skill in the art will be readily familiar. Such assays include, but need not be limited to, in vivo or in vitro determination of soluble antibodies, soluble mediators such as cytokines (e.g., IL-6, IL-1β, leukemia inhibitory factor. TNF-α, IFN-γ, IL-2, IL-4, IL-10, IL-12, and TGF-β), lymphokines, chemokines, hormones, growth factors, and the like, as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are may be found, for example, in Lefkovits (*Immunology Methods Manual: The Comprehensive Sourcebook of Techniques,* 1998). See also *Current Protocols in Immunology*; Weir, *Handbook of Experimental Immunology*, Blackwell Scientific, Boston. Mass. (1986); Mishell and Shigii (eds.) *Selected Methods in Cellular Immunology*, Freeman Publishing. San Francisco, Calif. (1979); Green and Reed, *Science* 281:1309 (1998) and references cited therein).

The compositions described herein may exhibit broad spectrum reduction in mucositis; and may exhibit anti-inflammatory activity, antimicrobial activity, reduction of pain, good stability, mucoadhesion, and when used in oral applications may provide adequate residence time in the mouth and high levels of patient compliance. As described in detail herein, compositions (pharmaceutically or physiologically acceptable) and methods of using the compositions are provided herein for treating dermal or mucosal disorders including side effects of radiation therapy and/or chemotherapy associated with the treatment of head and neck tumors and that also occurs in about 90% of children with leukemia. Such side effects include oral mucositis (including micro-lesions), and oral stomatitis. Such side effects (also called adverse effects) of chemotherapy or radiotherapy treatment of any one or more of a wide variety of solid or non-solid cancers (i.e., malignancies) or lymphomas (for example breast, prostate, pancreatic, ovarian, melanoma, liver, lung, urinary, and colon cancers; Kaposi's sarcoma) may also result in a mucosal disorder of any one or more mucosa including oral mucosa, intestinal mucosa, rectal mucosa, and the like. The compositions and methods described herein may also be used for preventing or treating a mucosal disorder such as atrophic vaginitis, vaginal micro-lesions, inflammatory bowel disease (including Crohn's disease and ulcerative colitis), eczema, psoriasis, periodontitis, interstitial cystitis, wound healing, or an inflammatory condition, dyspareunia, burning, leucorrhea, xerosis, vaginal dryness, vulvar pruritus, vaginal pruritus, vulvar burning, vaginal burning, vulvar dystrophy, vaginal malodor, candidiasis, trichomoniasis or bacterial vaginosis, and urinary disorders such as dysuria, hematuria, frequency, stress incontinence and tract infection, among other symptoms, including menopausal sexual dysfunction, complications resulting from antiestrogen medications, viral infections including shingles, herpes simplex, HIV/AIDS; and chronic skin disorders such as eczema, psoriasis and dermatitis, irritation due to oral surgery, aging and traumatic ulcers caused by braces or ill fitting dentures, diffuse aphthous ulcers, medication, or disease.

A subject (host or patient) in need of treatment as described herein may be a human or may be a non-human primate or other animal (i.e., veterinary use) who is afflicted with a dermal or mucosal disorder and has developed symptoms of a dermal or mucosal disease, disorder, or condition, or who may be free of detectable disease but is at risk for developing a dermal or mucosal disease, disorder, or condition. Accordingly, the compositions described herein may be administered to a subject who has an existing disease, or the treatment may be prophylactic, administered to a subject who is at risk for developing the disease or condition. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.). In certain embodiments, the subject is a human. In other certain embodiments, the compositions and methods described herein are excluded from veterinary use (i.e., use in any non-human animal).

A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. In certain embodiments, the subject or biological source may be a human or non-human animal, a primary cell culture (e.g., immune cells, virus infected cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

A derivative of a chemical compound (e.g., of a sulfonic acid or mineral salt) is structurally similar to a parent compound and (actually or theoretically) derivable from that parent compound. As used herein, derivatives include pharmaceutically acceptable derivatives of a compound used in the compositions described herein, which derivatives include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

Also provided herein are methods of manufacturing the compositions described herein. Such methods comprise formulating the compositions described herein comprising a mineral salt and a sulfonic acid and which may further comprise lactoferrin with other agents, excipients, and diluents as described herein. The manufacturing methods may further comprise adjusting the pH of the composition, and placing the composition in a suitable container for delivery to a health care provider or pharmacist.

EXAMPLES

Example 1

Bactericidal Activity of Compositions Comprising Zinc Gluconate and Taurine

This example illustrates the microbicidal activity of a composition comprising zinc gluconate and taurine.

GelX™ ORAL GEL was formulated as a viscous gel comprised of purified water, polyvinyl pyrrolidone (PVP), taurine, zinc gluconate. PEG-40 hydrogenated castor oil, sodium saccharin, sodium hydroxide, and flavoring. GelX™ ORAL GEL has a mechanical action which provides pain relief by adhering to the mucosal surface of the mouth and throat soothing lesions.

Antimicrobial activity of a composition comprising zinc gluconate and taurine was determined by a method typically used to demonstrate whether one or more agents may be included as a preservative in a composition formulated under conditions such that the composition will be considered a non-sterile composition according to regulatory authorities.

The minimum inhibitory concentration of solutions containing differing amounts of zinc gluconate and taurine (adjusted to a neutral pH with sodium hydroxide) were determined according to a method referred to as the Challenge Test that meets the requirements according to the Italian X Pharmacopoeia, which requirements are similar to U.S. requirements.

Testing was performed with solutions comprising 2% (w/w) zinc gluconate and 2% (w/w) taurine; 1% (w/w) zinc gluconate and 1% (w/w) taurine; 0.5% (w/w) zinc gluconate and 1% (w/w) taurine; 0.25% (w/w) zinc gluconate and 0.5% (w/w) taurine; and 0.1% (w/w) zinc gluconate and 0.1% (w/w) taurine. The inoculum of the microorganism used for the study is based on the presence of CFU of the microorganism per gram GelX™ ORAL GEL.

The acceptance criteria are defined in terms of decay of the number of microorganisms.

Microbiological Total Viable Count Before Challenge Test:

Total Aerobic Mesophilic Bacteria Count: <10 CFU/1 g
Mold and Yeast Total Count: <10 CFU/1 g Five different ATCC (Manassas, Va.) microbial strains were evaluated for microbial growth decay at four different intervals (48 hours, 7 days, 14 days and 28 days). The inoculum of the five microbial strains for each of the solutions tested is provided in the following Table. One set of experiments was performed to determine the antimicrobial activity of zinc gluconate/taurine at 0.5%/1.0% (w/w), and a second set of experiments were performed to determine the antimicrobial activity of zinc gluconate/taurine at four different ratios as indicated in Table 1 below.

TABLE 1

Antimicrobial Activity of Zinc Gluconate and Taurine Compositions

| Zn gluconate/taurine (w/w) (%) Microorganism | 0.5%/1.0% INOCULUM (CFU/g product) | 0.1%/0.1% 0.25%/0.5% 1.0%/1.0% 2.0%/2.0% INOCULUM (CFU/g product) |
|---|---|---|
| *Staphylococcus aureus* ATCC 6538 | $8.80 \times 10^6$ | $1.67 \times 10^6$ |
| *Pseudomonas aeruginosa* ATCC 9027 | $2.10 \times 10^6$ | $2.02 \times 10^7$ |
| *Escherichia coli* ATCC 8739 | $1.00 \times 10^7$ | $5.35 \times 10^6$ |
| *Candida albicans* ATCC 10231 | $1.20 \times 10^7$ | $9.80 \times 10^6$ |
| *Aspergillus niger* ATCC 16404 | $4.30 \times 10^6$ | $1.20 \times 10^6$ |

Five plates of the product tested were prepared, and each test sample was inoculated with a different microbial stump. The inoculated samples were maintained at 20° C.-25° C., and protected from light between intervals of inoculation. At the prescribed time intervals (48 hours, 7 days, 14 days, and 28 days), samples of 1 g/ml were taken from each inoculated sample.

Aliquots from the inoculated samples were applied to Petri dishes, which were incubated at 32° C. (bacteria) or at 20° C. (molds and yeast) for a time sufficient to allow microbial growth of (3 days for bacteria, 5-7 days for molds and yeast). The number of countable colonies was corrected for the proscribed dilution factor giving the number of CFU (Colony Forming Units) per gram of product. Samples were prepared at 48 hours, 7 days, 14 days and 28 days, to evaluate the trend of microbial growth. The cultures were routinely observed through the course of the weeks for which each sample was under study, and the differences in colony population for each microorganism were noted and recorded. Antimicrobial activity was also described in terms of log reduction of the number of viable microorganisms compared to the inoculated number of microorganisms.

Solutions at each of 2% (w/w) zinc gluconate and 2% (w/w) taurine; 1% (w/w) zinc gluconate and 1% (w/w) taurine; and 0.5% (w/w) zinc gluconate and 1% (w/w) taurine exhibited a significant reduction of microorganisms (CFU <10, or undetectable) present in each solution sample taken at each time point for each microorganism. Accordingly, the log reduction for each sample containing 0.5% zinc gluconate and 1.0% taurine was as follows: 6.94 for *S. aureus* inoculated samples, 6.32 for *P. aeruginosa* inoculated samples, 7.00 for *E. coli* inoculated samples, 7.08 for *C. albicans* inoculated samples, and 6.63 for *A. niger* inoculated samples. The log reduction for each sample containing 1.0% zinc gluconate/1.0% taurine and for each sample containing 2% zinc gluconate/2.0% taurine was as follows: 7.22 for *S. aureus* inoculated samples, 7.30 for *P. aeruginosa* inoculated samples, 6.73 for *E. coli* inoculated samples, 6.99 for *C. albicans* inoculated samples, and 6.08 for *A. niger* inoculated samples.

Solutions at each of 0.25% (w/w) zinc gluconate and 0.5% (w/w) taurine and 0.1% (w/w) zinc gluconate and 0.1% (w/w) taurine exhibited a significant reduction of microorganisms (CFU <10, or undetectable) present in each solution sample taken at each time point for each of *S. aureus, P. aeruginosa. C. albicans*, and *A. niger*. With respect to CFUs determined for *E. coli* at each time point in samples containing 0.1% (w/w) zinc gluconate and 0.1% (w/w) taurine, 10 CFUs *E. coli* were detected for each of 48 hours, 7, 14, and 28 days. For samples containing 0.25% (w/w) zinc gluconate and 0.5% (w/w) taurine, 10 *E. coli* CFUs were detected in samples at 48 hours and at 7 days but the number of bacteria in samples evaluated at 14 days and 28 days was <10 or undetectable.

Example 2

Treatment of Oral Aphthous Stomatitis

This example describes the effectiveness of using a composition comprising zinc gluconate and taurine and polyvinyl pyrrolidone (PVP) for treatment of oral aphthous stomatitis.

A painful ulcer inside the oral cavity caused by a rupture of the membrane is defined by the term aphthous. An aphthous ulcer is also called a canker sore. When multiple aphthous ulcers occur and/or when the condition is chronic (or recurrent), the condition is called aphthous stomatitis (see, e.g., Natah et al., *Int. J. Oral. Maxillofac. Surg.* 33:221-34 (2004)).

Over a period of eleven months, in a dentist's surgery in Italy, 150 patients who were affected by minor aphthous were recruited to participate in a clinical study. The patients (87 female and 63 male) were between the ages of 18 and 71 and provided informed consent to participate. The patients were randomly divided into five groups, thirty people each.

Group A: Patients were treated with 100% pure Vitamin E (Vea Oil, Hulka srl, Rovigo, Italy.

Group B: Patients were treated with a gel containing an Aloe Vera extract (ALOVEX gel, Recordati spA, Milan, Italy).

Group C: Patients were not prescribed any treatment and formed a non-treatment control group.

Group D: Patients were treated with a BMG0902-03 gel. (BMG Pharma. Gardnerville, N.V.; lot 101108). The BMG0902-03 gel is viscous gel containing 12% w/w polyvinyl pyrrolidone (PVP), 1% (w/w) taurine, 0.5% (w/w) zinc gluconate, and also containing PEG-40 hydrogenated castor oil, sodium saccharin, sodium hydroxide, flavoring, and purified water.

Group E: Patients were treated with a product containing only Vitamin A associated with other polymers.

The patients were advised to apply the assigned product 4 times per day (after main meals and in the evening before going to bed) and were advised to avoid eating or drinking for at least an hour after application. The patients in groups A, B, D and E were asked to cover the entire sore with the prescribed gel. All patients were scheduled for a follow-up visit seven days after beginning treatment. After the required seven days, patients who did not report to the dentists' office were excluded from the study. Excluded were five patients from group A; nine from group B; five from group C; seven from group D; and five from group E. Therefore, patients who completed the study included 25 from group A: 21 from group B; 25 from group C; 23 from group D; and 25 from group E.

Clinical progress was evaluated based on the presence of oral ulcers and the number and distribution of the sores. A photographic record was made at the first visit and at the check-up seven days later. Healing was defined for the purpose of this study as (1) absence of painful and burning symptoms; and (2) absence of ulcerous lesions. The results were evaluated according to the following scoring system: complete healing (+++); lesion present, but asymptomatic (++); reduction by half of symptomatology (+); persistence of the symptoms and signs of aphthous ulcer (−); side effects (^). The data are presented in Table 2.

TABLE 2

Treatment of Minor Aphthous Ulcers

| | Group A | Group B | Group C | Group D | Group E |
|---|---|---|---|---|---|
| Complete Healing (+++) | 85% | 80% | 40% | 90% | 20% |
| lesion present, but asymptomatic (++) | 13% | 15% | 20% | 5% | 30% |
| reduction by half of symptomatology (+) | 2% | 5% | 10% | 5% | 20% |
| persistence of symptoms and signs (−) | 0 | 0 | 30% | 0 | 30% |
| side effects (^) | 0 | 0 | 0 | 0 | 0 |

Example 3

Inhibition of IL-6 and IL-8 Production in Cells by Zinc and Taurine

This example describes the capability of zinc (e.g., zinc gluconate) in combination with taurine to inhibit production of cytokines, IL-6 and IL-8, in cells stimulated by either lipopolysaccharide (LPS) or doxorubicin, a chemotherapeutic agent.

Figure 2:
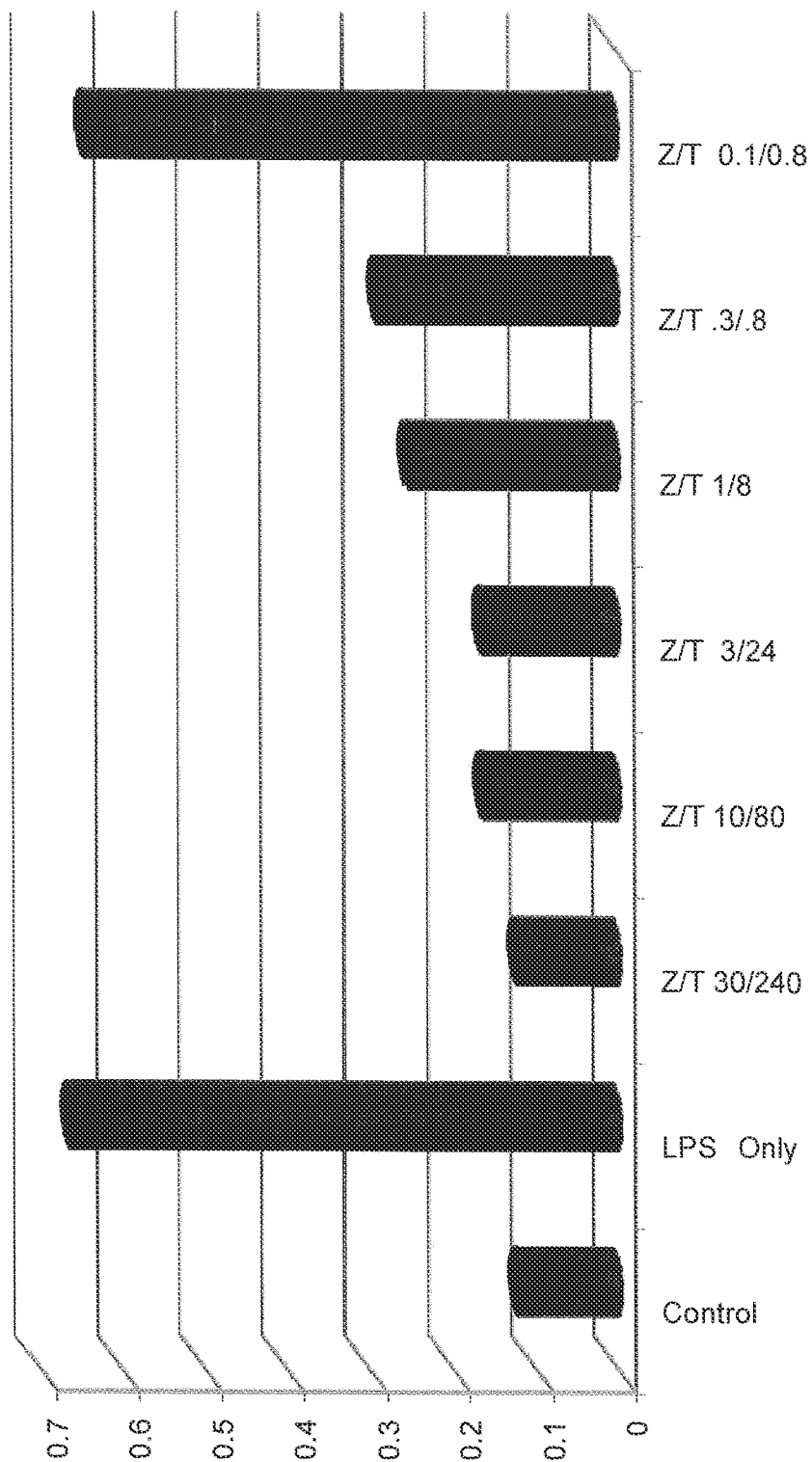
FIG. 2 illustrates the effect of zinc (Z) and taurine (T) to reduce production of the proinflammatory cytokine IL-8 in lipopolysaccharide-stimulated CaCo2 cells. The concentrations for each of zinc gluconate and taurine (Z/T) are indicated in mM on the x-axis.
Figure 3:
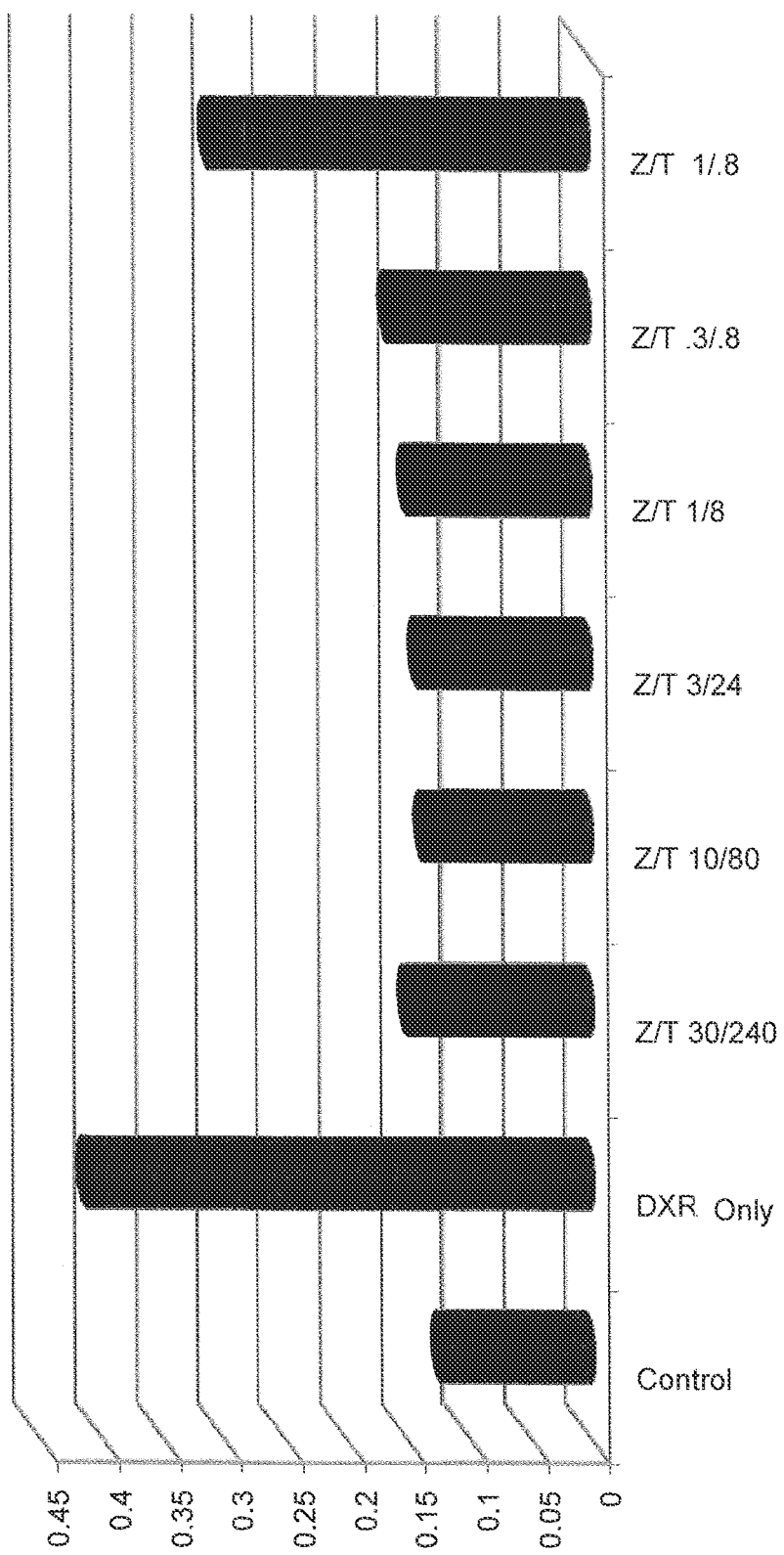
FIG. 3 illustrates the effect of zinc (Z) and taurine (T) to reduce production of the proinflammatory cytokine IL-8 in doxorubicin-stimulated CaCo2 cells. The concentrations for each of zinc gluconate and taurine (Z/T) are indicated in mM on the x-axis.

CaCo2 cells (human intestinal (colonic) epithelial cells) were grown in culture in 24-well tissue culture dishes according to methods routinely practiced in the cell culture art. Zinc gluconate and taurine were combined at varying concentrations and added to the cells in the absence and presence of proinflammatory agents (lipopolysaccharide, doxorubicin, dextran-sulfate sodium (DSS)). In one series, zinc gluconate and taurine were combined with lipopolysaccharide (LPS) (1 µg/ml) for six hours. In a second series, zinc gluconate and taurine were combined with doxorubicin (3 µM) for 24 hours. In a third series, zinc gluconate and taurine were combined with DSS (5% w/w) for 24 hours. For detecting inhibition of IL-6 or IL-8 production in the cells stimulated with each of the pro-inflammatory agents, the zinc/taurine (Z/T) concentrations (mM) were as follows: Z/T: 0.1/0.8; Z/T: 0.3/2.4; Z/T: 1/8; Z/T: 3/24; Z/T: 10/80; and Z/T: 30/240. After stimulation, the cell supernatants were harvested. The presence of IL-6 and IL-8 in cell supernatants from cells stimulated with the agents was determined using commercially available reagents for detection of each according to the manufacturer's instructions (ORGENIUM ELISA kits, Anibiotech Oy, Orgenium Laboratories Division, Vantaa, Finland). Inhibition of production of IL-6 and IL-8 by zinc gluconate and taurine in cells stimulated with LPS is presented in FIG. 1 and FIG. 2, respectively. The data are presented in FIGS. 1 and 2. Inhibition of production of IL-8 by zinc gluconate and taurine in cells stimulated with doxorubicin is presented in FIG. 3. In CaCo-2 cells to which DSS was added, IL-8 production was inhibited to background levels at each of the zinc/taurine concentrations tested.

Figure 4:
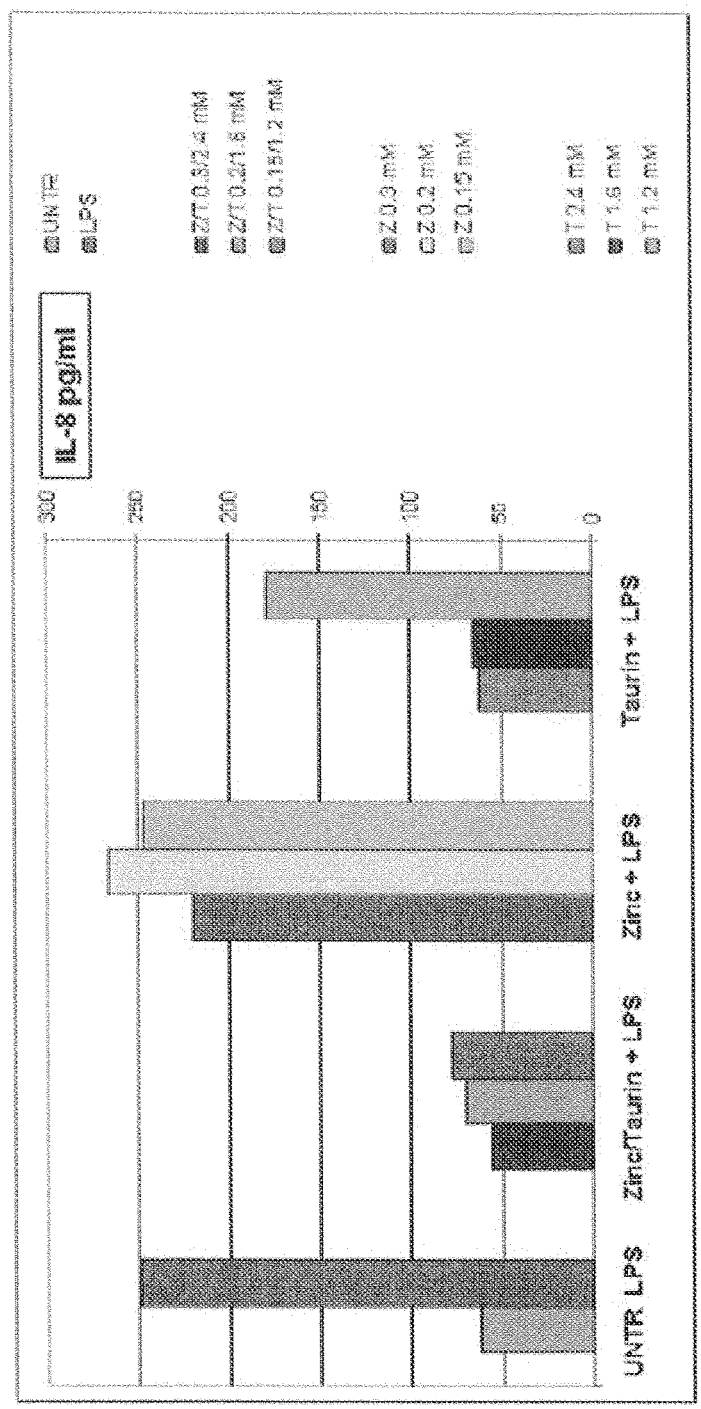
FIG. 4 shows the effect of zinc (Z) alone, taurine ((T); also indicated as "Taurin") alone, and the combination of zinc and taurine on production of IL-8 in lipopolysaccharide-stimulated CaCo2 cells. The concentration (pg/ml) of IL-8 detected is shown on the y-axis. Controls include CaCo-2 cells that were not exposed to LPS (UNTR), and CaCo-2 cells that were exposed to LPS (LPS) but not to either zinc gluconate or taurine or both zinc gluconate and taurine together.

In a second set of experiments, CaCo-2 cells were stimulated with LPS in the presence of zinc gluconate alone (0.15 mM, 0.2 mM, and 0.3 mM), taurine alone (1.2 mM, 1.6 mM, and 2.4 mM), and both zinc gluconate (Z) and taurine (T) (Z/T: 0.15 mM/1.2 mM; Z/T: 0.2 mM/1.6 mM; and Z/T: 0.3 mM/2.4 mM). The level of IL-8 (pg/ml) in the cell supernatants was then determined as described above. The results are presented in FIG. 4.

Example 4

Treatment of Mucositis with Zinc and Taurine

This example describes treatment of five patients who had radiation therapy-induced-mucositis with a muco-adhesive gel containing 0.5% (w/w) zinc gluconate and 1.0% (w/w) taurine.

Five patients with head or neck cancer, each of whom had moderate to severe mucositis, were treated with a muco-adhesive gel containing 0.5% (w/w) zinc gluconate and 1.0% taurine (w/w) on an open label basis. Each patient was being treated for recurrent disease, and each had previously been diagnosed with radiation therapy-induced mucositis during a previous treatment.

The patients were provided with the muco-adhesive gel in each of two different presentations: (1) 450 ml bottles with 15 ml dispensing cups, and (2) 150 ml bottle with a long neck spray tip to be able to reach specific lesions. Patients were instructed to use the product as needed at least 3 but not more than 5 times each day, including preferably one hour prior to meals.

Observations of the effects of the treatment were made by the treating physician at approximately seven days after initiating treatment; observations included incorporation of patient statements. Following are the results of this open label study.

(1) Two patients deemed to have severe oral mucositis were observed to have clinically significant reductions in the extent of their lesions, including a notable reduction in common indications of inflammation, such as edema. No new lesions occurred in either patient even as radiation therapy continued. Each of these two patients reported significant and increasingly sustained reductions of pain associated with their lesions, and each reported an increased ability to eat and drink, which had been problematic for each during the peak of their mucositis symptoms.

(2) One additional patient was observed to have the same or similar reduction in the general symptoms of mucositis. Additionally, this patient reported the return of his ability to taste food after only three days of treatment, a faculty previously lost during treatment. The return of this ability was accompanied by an increase in saliva production, which had been dramatically reduced as a consequence of radiation therapy.

(3) Two patients deemed to have moderate mucositis with lesions toward the back of their mouths and throats used localized therapy with the spray tip package. Each reported near immediate reduction of pain and enhanced ability to swallow. Clinical observations were consistent with the three other patients (see (1) and (2) above) with regard to a reduction of severity of the lesions and observable characteristics of inflammation.

Example 5

Treatment of Dermal Conditions with Zinc and Taurine

This example describes treatment of dermal conditions with compositions comprising zinc gluconate and taurine.

(1) Thermal Injury. An adult woman experienced a severe burn with boiling water that resulted in immediate skin blistering, erythema, and intense pain. The burn affected approximately 70% of her left breast, the entire nipple, and portions of her left abdomen. Within 5 minutes of the injury, a zinc gluconate (0.5% w/w) and taurine (1.0% w/w) aqueous gel composition was applied to the injured area. An additional component of the gel included 1% (w/w) PVP. Fifteen minutes later an additional application of the gel was applied. When the skin was examined 30 minutes after the injury, nearly all erythema had dissipated, resulting in a skin tone and color nearly identical to adjacent non-injured skin, and the pain associated with the injury had resolved.

(2) Diaper Dermatitis. A two year old child experienced diaper rash, redness, and irritation. The child was treated with a gel containing zinc gluconate (2.5% w/w) and taurine (5% w/w) for the condition. Twelve hours after the first application, most of the redness and irritation had disappeared. The child was treated again the following day, once in the morning and again in the evening. The following day the child's condition resolved.

(3) Intertrigo (inflammation/rash of a body fold). A woman developed a skin fold infection that presented as a painful, inflamed, reddish-brown rash. The rash was treated with a gel containing zinc gluconate (2.5% w/w) and taurine (5% w/w), twice a day over a three day period. After the treatment, the rash resolved.

Example 6

Treatment of Oral Mucositis Associated with Head and Neck Cancer

This example provides a study of oral mucositis associated with radiotherapy, chemotherapy, or a combination of radiotherapy and chemotherapy for the treatment of head and neck cancer. This study evaluates any one or more of, for example, the onset of oral mucositis, pain, severity of oral mucositis, or decrease in the time to resolution of oral mucositis. This study includes a treatment period lasting through the duration of radiotherapy and/or chemotherapy, continuing until resolution of oral mucositis. This study involves 4 groups of subjects receiving one of the following formulations: (1) Placebo (sterile water), (2) a GelX™ Oral Gel (medium viscosity) (0.5% w/w zinc gluconate, 1.0% w/w taurine and 4.0% w/w PVP). (3) GelX Oral Gel (high viscosity) (0.5% w/w zinc gluconate, 1.0% w/w taurine and 8.0% w/w PVP), or (4) a GelX Oral Gel 4× (medium viscosity) (2.0% w/w zinc gluconate, 4.0% w/w taurine and 4.0% w/w PVP).

Formulations to be evaluated are administered locally as a mouth rinse for a period of time such as 30 seconds, one minute, or 1.5 minutes. Administration is once, twice or three times a day or as needed, with drinking and eating withheld for at least thirty minutes thereafter.

Results are evaluated based upon any one or more of: (1) time of onset of oral mucositis, (2) time to resolution of oral mucositis. (3) mouth soreness, (4) percentage of subjects developing oral mucositis, (5) safety. (6) average number of doses administered, and (7) dry mouth. Results of the study are evaluated using the WHO Oral Mucositis Assessment Scale, according to Table 3 below.

TABLE 3

| WHO Oral Mucositis Assessment Scale | | | | | |
|---|---|---|---|---|---|
| Grade | 0 | 1 | 2 | 3 | 4 |
| | None | Soreness and/or erythema | Erythema, ulcers, and patient can swallow solid food | Ulcers with extensive erythema and patient cannot swallow solid food | Mucositis to extent that alimentation is not possible |

The above criteria are evaluated at least on the basis of pain (1) in general, (2) of the mouth, and (3) of the throat; and for saliva based upon (1) swallowing, (2) amount, (3) consistency.

All U.S. patents. U.S. patent application publications, U.S. patent applications, foreign patents, foreign patent applications and non-patent publications referred to in this specification and/or listed in the Application Data Sheet, are incorporated herein by reference, each in their entirety.

From the foregoing a person skilled in the art will appreciate that, although specific embodiments have been described herein for purposes of illustration, various modifications may be made. Those skilled in the art will recognize, or be able to ascertain, using no more than routine experimentation, many equivalents to the specific embodiments described herein. Such equivalents are intended to be encompassed by the following claims. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. Method of treating dermal conditions in a human subject with a composition consisting of zinc gluconate and taurine, said method comprising:

applying to each dermal area in need thereof of said human subject a pharmaceutically effective amount of said composition.

* * * * *

SEQUENCE LISTING

<160> NUMBER OF SEQ ID NOS: 20

<210> SEQ ID NO 1
<211> LENGTH: 711

```
<212> TYPE: PRT
<213> ORGANISM: Homo sapiens

<400> SEQUENCE: 1

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30

Gln Pro Glu Ala Thr Lys Cys Phe Gln Trp Gln Arg Asn Met Arg Lys
            35                  40                  45

Val Arg Gly Pro Pro Val Ser Cys Ile Lys Arg Asp Ser Pro Ile Gln
50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
            115                 120                 125

Leu Gln Gly Leu Lys Ser Cys His Thr Gly Leu Arg Arg Thr Ala Gly
130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
            195                 200                 205

Tyr Phe Ser Tyr Ser Gly Ala Phe Lys Cys Leu Arg Asp Gly Ala Gly
            210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
            275                 280                 285

Asn Leu Leu Arg Gln Ala Gln Glu Lys Phe Gly Lys Asp Lys Ser Pro
290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
            355                 360                 365

Ala Val Gly Glu Gln Glu Leu Arg Lys Cys Asn Gln Trp Ser Gly Leu
370                 375                 380

Ser Glu Gly Ser Val Thr Cys Ser Ser Ala Ser Thr Thr Glu Asp Cys
385                 390                 395                 400
```

```
Ile Ala Leu Val Leu Lys Gly Glu Ala Asp Ala Met Ser Leu Asp Glu
            405                 410                 415

Gly Tyr Val Tyr Thr Ala Gly Lys Cys Gly Leu Val Pro Val Leu Ala
        420                 425                 430

Glu Asn Tyr Lys Ser Gln Gln Ser Ser Asp Pro Asp Pro Asn Cys Val
            435                 440                 445

Asp Arg Pro Val Glu Gly Tyr Leu Ala Val Ala Val Val Arg Arg Ser
450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
            485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525

Gly Asp Glu Gln Gly Glu Asn Lys Cys Val Pro Asn Ser Asn Glu Arg
    530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
            565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
            645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys
705                 710

<210> SEQ ID NO 2
<211> LENGTH: 711
<212> TYPE: PRT
<213> ORGANISM: Homo sapiens

<400> SEQUENCE: 2

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30

Gln Pro Glu Ala Thr Lys Cys Phe Gln Trp Gln Arg Asn Met Arg Arg
        35                  40                  45

Val Arg Gly Pro Pro Val Ser Cys Ile Lys Arg Asp Ser Pro Ile Gln
```

```
            50                  55                  60
Cys Ile Gln Ala Ile Ala Glu Asn Arg Ala Asp Ala Val Thr Leu Asp
 65                  70                  75                  80
Gly Gly Phe Ile Tyr Glu Ala Gly Leu Ala Pro Tyr Lys Leu Arg Pro
                     85                  90                  95
Val Ala Ala Glu Val Tyr Gly Thr Glu Arg Gln Pro Arg Thr His Tyr
                    100                 105                 110
Tyr Ala Val Ala Val Val Lys Lys Gly Gly Ser Phe Gln Leu Asn Glu
                    115                 120                 125
Leu Gln Gly Leu Lys Ser Cys His Thr Gly Leu Arg Arg Thr Ala Gly
                    130                 135                 140
Trp Asn Val Pro Ile Gly Thr Leu Arg Pro Phe Leu Asn Trp Thr Gly
145                 150                 155                 160
Pro Pro Glu Ser Ile Glu Ala Ala Val Ala Arg Phe Phe Ser Ala Ser
                    165                 170                 175
Cys Val Pro Gly Ala Asp Lys Gly Gln Phe Pro Asn Leu Cys Arg Leu
                    180                 185                 190
Cys Ala Gly Thr Gly Glu Asn Lys Cys Ala Phe Ser Ser Gln Glu Pro
                    195                 200                 205
Tyr Phe Ser Tyr Ser Gly Ala Phe Lys Cys Leu Arg Asp Gly Ala Gly
                    210                 215                 220
Asp Val Ala Phe Ile Arg Glu Ser Thr Val Phe Glu Asp Leu Ser Asp
225                 230                 235                 240
Glu Ala Glu Arg Asp Glu Tyr Glu Leu Leu Cys Pro Asp Asn Thr Arg
                    245                 250                 255
Lys Pro Val Asp Lys Phe Lys Asp Cys His Leu Ala Arg Val Pro Ser
                    260                 265                 270
His Ala Val Val Ala Arg Ser Val Asn Gly Lys Glu Asp Ala Ile Trp
                    275                 280                 285
Asn Leu Leu Arg Gln Ala Gln Glu Lys Phe Gly Lys Asp Lys Ser Pro
                    290                 295                 300
Lys Phe Gln Leu Phe Gly Ser Pro Ser Gly Lys Asp Leu Leu Phe
305                 310                 315                 320
Lys Asp Ser Ala Ile Gly Phe Ser Arg Val Pro Pro Arg Ile Asp Ser
                    325                 330                 335
Gly Leu Tyr Leu Gly Ser Gly Tyr Phe Thr Ala Ile Gln Asn Leu Arg
                    340                 345                 350
Lys Ser Glu Glu Glu Val Ala Ala Arg Arg Ala Arg Val Val Trp Cys
                    355                 360                 365
Ala Val Gly Glu Gln Glu Leu Arg Lys Cys Asn Gln Trp Ser Gly Leu
                    370                 375                 380
Ser Glu Gly Ser Val Thr Cys Ser Ser Ala Ser Thr Thr Glu Asp Cys
385                 390                 395                 400
Ile Ala Leu Val Leu Lys Gly Glu Ala Asp Ala Met Ser Leu Asp Gly
                    405                 410                 415
Gly Tyr Val Tyr Thr Ala Gly Lys Cys Gly Leu Val Pro Val Leu Ala
                    420                 425                 430
Glu Asn Tyr Lys Ser Gln Gln Ser Ser Asp Pro Asp Pro Asn Cys Val
                    435                 440                 445
Asp Arg Pro Val Glu Gly Tyr Leu Ala Val Ala Val Val Arg Arg Ser
                    450                 455                 460
Asp Thr Ser Leu Thr Trp Asn Ser Val Lys Gly Lys Lys Ser Cys His
465                 470                 475                 480
```

```
Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525

Gly Asp Glu Gln Gly Glu Asn Lys Cys Val Pro Asn Ser Asn Glu Arg
    530                 535                 540

Tyr Tyr Gly Tyr Thr Gly Ala Phe Arg Cys Leu Ala Glu Asp Ala Gly
545                 550                 555                 560

Asp Val Ala Phe Val Lys Asp Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys
705                 710

<210> SEQ ID NO 3
<211> LENGTH: 711
<212> TYPE: PRT
<213> ORGANISM: Homo sapiens

<400> SEQUENCE: 3

Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30

Gln Pro Glu Ala Thr Lys Cys Phe Gln Trp Gln Arg Asn Met Arg Arg
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Asn Ala Gly
```

```
                130             135             140
Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
                180                 185                 190

Cys Ala Gly Thr Gly Glu Asn Lys Cys Ala Phe Ser Ser Gln Glu Pro
                195                 200                 205

Tyr Phe Ser Tyr Ser Gly Ala Phe Lys Cys Leu Arg Asp Gly Ala Gly
210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
                260                 265                 270

His Ala Val Val Ala Arg Ser Val Asn Gly Lys Glu Asp Ala Ile Trp
                275                 280                 285

Asn Leu Leu Arg Gln Ala Gln Glu Lys Phe Gly Lys Asp Lys Ser Pro
290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
                340                 345                 350

Lys Ser Glu Glu Glu Val Ala Ala Arg Ala Arg Val Val Trp Cys
                355                 360                 365

Ala Val Gly Glu Gln Glu Leu Arg Lys Cys Asn Gln Trp Ser Gly Leu
                370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
                405                 410                 415

Gly Tyr Val Tyr Thr Ala Gly Lys Cys Gly Leu Val Pro Val Leu Ala
                420                 425                 430

Glu Asn Tyr Lys Ser Gln Gln Ser Ser Asp Pro Asp Pro Asn Cys Val
                435                 440                 445

Asp Arg Pro Val Glu Gly Tyr Leu Ala Val Ala Val Val Arg Arg Ser
450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
                500                 505                 510

Cys Ala Pro Gly Ser Asp Pro Arg Ser Asn Leu Cys Ala Leu Cys Ile
                515                 520                 525

Gly Asp Glu Gln Gly Glu Asn Lys Cys Val Pro Asn Ser Asn Glu Arg
530                 535                 540

Tyr Tyr Gly Tyr Thr Gly Ala Phe Arg Cys Leu Ala Glu Asp Ala Gly
545                 550                 555                 560
```

-continued

Asp Val Ala Phe Val Lys Gly Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys
705                 710

<210> SEQ ID NO 4
<211> LENGTH: 708
<212> TYPE: PRT
<213> ORGANISM: Bos taurus

<400> SEQUENCE: 4

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Arg Ala Phe Ala Leu Glu Cys
    50                  55                  60

Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
    130                 135                 140

Val Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp

-continued

```
                210                 215                 220
Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
                260                 265                 270

Ala Val Val Ala Arg Ser Val Asp Gly Lys Glu Asp Leu Ile Trp Lys
                275                 280                 285

Leu Leu Ser Lys Ala Gln Glu Lys Phe Gly Lys Asn Lys Ser Arg Ser
290                 295                 300

Phe Gln Leu Phe Gly Ser Pro Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
                340                 345                 350

Thr Ala Glu Glu Val Lys Ala Arg Tyr Thr Arg Val Val Trp Cys Ala
                355                 360                 365

Val Gly Pro Glu Glu Gln Lys Lys Cys Gln Gln Trp Ser Gln Gln Ser
370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
                420                 425                 430

Asn Arg Lys Thr Ser Lys Tyr Ser Ser Leu Asp Cys Val Leu Arg Pro
                435                 440                 445

Thr Glu Gly Tyr Leu Ala Val Ala Val Val Lys Lys Ala Asn Glu Gly
                450                 455                 460

Leu Thr Trp Asn Ser Leu Lys Asp Lys Lys Ser Cys His Thr Ala Val
465                 470                 475                 480

Asp Arg Thr Ala Gly Trp Asn Ile Pro Met Gly Leu Ile Val Asn Gln
                485                 490                 495

Thr Gly Ser Cys Ala Phe Asp Glu Phe Phe Ser Gln Ser Cys Ala Pro
                500                 505                 510

Gly Arg Asp Pro Lys Ser Arg Leu Cys Ala Leu Cys Ala Gly Asp Asp
                515                 520                 525

Gln Gly Leu Asp Lys Cys Val Pro Asn Ser Lys Glu Lys Tyr Tyr Gly
                530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
                580                 585                 590

Leu Asp Gly Thr Arg Lys Pro Val Thr Glu Ala Gln Ser Cys His Leu
                595                 600                 605

Ala Val Ala Pro Asn His Ala Val Val Ser Arg Ser Asp Arg Ala Ala
                610                 615                 620

His Val Lys Gln Val Leu Leu His Gln Gln Ala Leu Phe Gly Lys Asn
625                 630                 635                 640
```

```
Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
            660                 665                 670

Arg Pro Thr Tyr Glu Glu Tyr Leu Gly Thr Gly Tyr Val Thr Ala Ile
        675                 680                 685

Ala Asn Leu Lys Lys Cys Ser Thr Ser Pro Leu Leu Glu Ala Cys Ala
690                 695                 700

Phe Leu Thr Arg
705

<210> SEQ ID NO 5
<211> LENGTH: 708
<212> TYPE: PRT
<213> ORGANISM: Bos taurus

<400> SEQUENCE: 5

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Arg Ala Phe Ala Leu Glu Cys
    50                  55                  60

Ile Pro Gly Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
    130                 135                 140

Ile Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
    210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
        275                 280                 285

Leu Leu Ser Lys Ala Gln Glu Lys Ser Gly Lys Asn Lys Ser Arg Ser
```

```
            290                 295                 300
Phe Gln Leu Phe Gly Ser Pro Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
                340                 345                 350

Thr Ala Glu Glu Val Lys Ala Arg Tyr Thr Arg Val Val Trp Cys Ala
            355                 360                 365

Val Gly Pro Glu Glu Gln Lys Lys Cys Gln Gln Trp Ser Gln Gln Ser
            370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
                420                 425                 430

Asn Arg Lys Ser Ser Lys His Ser Ser Leu Asp Cys Val Leu Arg Pro
            435                 440                 445

Thr Glu Gly Tyr Leu Ala Val Ala Val Val Lys Lys Ala Asn Glu Gly
            450                 455                 460

Leu Thr Trp Asn Ser Leu Lys Asp Lys Lys Ser Cys His Thr Ala Val
465                 470                 475                 480

Asp Arg Thr Ala Gly Trp Asn Ile Pro Met Gly Leu Ile Val Asn Gln
                485                 490                 495

Thr Gly Ser Cys Ala Phe Asp Glu Phe Phe Ser Gln Ser Cys Ala Pro
                500                 505                 510

Gly Ala Asp Pro Lys Ser Arg Leu Cys Ala Leu Cys Ala Gly Asp Asp
            515                 520                 525

Gln Gly Leu Asp Lys Cys Val Pro Asn Ser Lys Glu Lys Tyr Tyr Gly
            530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
            580                 585                 590

Leu Asp Gly Thr Arg Lys Pro Val Thr Glu Ala Gln Ser Cys His Leu
            595                 600                 605

Ala Val Ala Pro Asn His Ala Val Val Ser Arg Ser Asp Arg Ala Ala
610                 615                 620

His Val Lys Gln Val Leu Leu His Gln Gln Ala Leu Phe Gly Lys Asn
625                 630                 635                 640

Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
                660                 665                 670

Arg Pro Thr Tyr Glu Glu Tyr Leu Gly Thr Glu Tyr Val Thr Ala Ile
            675                 680                 685

Ala Asn Leu Lys Lys Cys Ser Thr Ser Pro Leu Leu Glu Ala Cys Ala
            690                 695                 700

Phe Leu Thr Arg
705
```

<210> SEQ ID NO 6
<211> LENGTH: 708
<212> TYPE: PRT
<213> ORGANISM: Bos taurus

<400> SEQUENCE: 6

```
Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Arg Ala Phe Ala Leu Glu Cys
    50                  55                  60

Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
    130                 135                 140

Ile Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
    210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
        275                 280                 285

Leu Leu Ser Lys Ala Gln Glu Lys Phe Gly Lys Asn Lys Ser Arg Ser
    290                 295                 300

Phe Gln Leu Phe Gly Ser Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
            340                 345                 350

Thr Ala Glu Glu Val Lys Ala Arg Tyr Thr Arg Val Val Trp Cys Ala
        355                 360                 365

Val Gly Pro Glu Glu Gln Lys Lys Cys Gln Gln Trp Ser Gln Gln Ser
```

```
            370                 375                 380
Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
                420                 425                 430

Asn Arg Lys Ser Ser Lys His Ser Ser Leu Asp Cys Val Leu Arg Pro
                435                 440                 445

Thr Glu Gly Tyr Leu Ala Val Ala Val Val Lys Lys Ala Asn Glu Gly
            450                 455                 460

Leu Thr Trp Asn Ser Leu Lys Asp Lys Lys Ser Cys His Thr Ala Val
465                 470                 475                 480

Asp Arg Thr Ala Gly Trp Asn Ile Pro Met Gly Leu Ile Val Asn Gln
                485                 490                 495

Thr Gly Ser Cys Ala Phe Asp Glu Phe Phe Ser Gln Ser Cys Ala Pro
                500                 505                 510

Gly Ala Asp Pro Lys Ser Arg Leu Cys Ala Leu Cys Ala Gly Asp Asp
                515                 520                 525

Gln Gly Leu Asp Lys Cys Val Pro Asn Ser Lys Glu Lys Tyr Tyr Gly
            530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
                580                 585                 590

Leu Asp Gly Thr Arg Lys Pro Val Thr Glu Ala Gln Ser Cys His Leu
            595                 600                 605

Ala Val Ala Pro Asn His Ala Val Val Ser Arg Ser Asp Arg Ala Ala
                610                 615                 620

His Val Lys Gln Val Leu Leu His Gln Gln Ala Leu Phe Gly Lys Asn
625                 630                 635                 640

Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
                660                 665                 670

Arg Pro Thr Tyr Glu Glu Tyr Leu Gly Thr Glu Tyr Val Thr Ala Ile
                675                 680                 685

Ala Asn Leu Lys Lys Cys Ser Thr Ser Pro Leu Leu Glu Ala Cys Ala
            690                 695                 700

Phe Leu Thr Arg
705

<210> SEQ ID NO 7
<211> LENGTH: 708
<212> TYPE: PRT
<213> ORGANISM: Bos taurus

<400> SEQUENCE: 7

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
                20                  25                  30
```

```
Pro Glu Trp Phe Lys Cys Arg Arg Trp Gln Trp Arg Met Lys Lys Leu
            35                  40                  45
Gly Ala Pro Ser Ile Thr Cys Val Arg Arg Ala Phe Ala Leu Ala Cys
 50                  55                  60
Ile Arg Ala Ile Ala Glu Lys Lys Ala Asp Ala Val Thr Leu Asp Gly
 65                  70                  75                  80
Gly Met Val Phe Glu Ala Gly Arg Asp Pro Tyr Lys Leu Arg Pro Val
                85                  90                  95
Ala Ala Glu Ile Tyr Gly Thr Lys Glu Ser Pro Gln Thr His Tyr Tyr
                100                 105                 110
Ala Val Ala Val Val Lys Lys Gly Ser Asn Phe Gln Leu Asp Gln Leu
                115                 120                 125
Gln Gly Arg Lys Ser Cys His Thr Gly Leu Gly Arg Ser Ala Gly Trp
    130                 135                 140
Val Ile Pro Met Gly Ile Leu Arg Pro Tyr Leu Ser Trp Thr Glu Ser
145                 150                 155                 160
Leu Glu Pro Leu Gln Gly Ala Val Ala Lys Phe Phe Ser Ala Ser Cys
                165                 170                 175
Val Pro Cys Ile Asp Arg Gln Ala Tyr Pro Asn Leu Cys Gln Leu Cys
                180                 185                 190
Lys Gly Glu Gly Glu Asn Gln Cys Ala Cys Ser Ser Arg Glu Pro Tyr
                195                 200                 205
Phe Gly Tyr Ser Gly Ala Phe Lys Cys Leu Gln Asp Gly Ala Gly Asp
    210                 215                 220
Val Ala Phe Val Lys Glu Thr Thr Val Phe Glu Asn Leu Pro Glu Lys
225                 230                 235                 240
Ala Asp Arg Asp Gln Tyr Glu Leu Leu Cys Leu Asn Asn Ser Arg Ala
                245                 250                 255
Pro Val Asp Ala Phe Lys Glu Tyr His Leu Ala Gln Val Pro Ser His
                260                 265                 270
Pro Val Val Ala Arg Ser Val Asp Ala Lys Glu Asp Leu Ile Trp Lys
                275                 280                 285
Leu Leu Arg Lys Ala Gln Glu Lys Phe Gly Lys Asn Lys Ser Arg Ser
    290                 295                 300
Phe Gln Leu Phe Gly Ser Pro Pro Gly Gln Arg Asp Leu Leu Phe Lys
305                 310                 315                 320
Asp Ser Ala Leu Gly Phe Leu Arg Ile Pro Ser Lys Val Asp Ser Ala
                325                 330                 335
Leu Tyr Leu Gly Ser Arg Tyr Leu Thr Thr Leu Lys Asn Leu Arg Glu
                340                 345                 350
Thr Ala Glu Glu Val Lys Ala Arg Tyr Thr Arg Val Val Trp Cys Ala
                355                 360                 365
Val Gly Pro Glu Glu Gln Lys Lys Cys Gln Gln Trp Ser Gln Gln Ser
    370                 375                 380
Gly Gln Asn Val Thr Cys Ala Thr Ala Ser Thr Thr Asp Asp Cys Ile
385                 390                 395                 400
Val Leu Val Leu Lys Gly Glu Ala Asp Ala Leu Asn Leu Asp Gly Gly
                405                 410                 415
Tyr Val Tyr Thr Ala Gly Lys Cys Gly Leu Val Pro Val Leu Ala Glu
                420                 425                 430
Asn Arg Lys Ser Ser Lys His Ser Ser Leu Asp Cys Val Leu Arg Pro
                435                 440                 445
Thr Glu Gly Tyr Leu Ala Val Ala Val Val Arg Lys Ala Asn Glu Gly
```

```
                450             455             460
Leu Thr Trp Asn Ser Leu Lys Asp Lys Ser Cys His Thr Ala Val
465                 470                 475                 480

Asp Arg Thr Ala Gly Trp Asn Ile Pro Met Gly Leu Ile Val Asn Gln
                485                 490                 495

Thr Gly Ser Cys Ala Phe Asp Glu Phe Ser Gln Ser Cys Ala Pro
                500                 505                 510

Gly Ala Asp Pro Lys Ser Arg Leu Cys Ala Leu Cys Ala Gly Asp Asp
                515                 520                 525

Gln Gly Leu Asp Lys Cys Val Pro Asn Ser Lys Glu Lys Tyr Tyr Gly
                530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
                580                 585                 590

Leu Asp Gly Thr Arg Lys Pro Val Thr Glu Ala Gln Ser Cys His Leu
                595                 600                 605

Ala Val Ala Pro Asn His Ala Val Val Ser Arg Ser Asp Arg Ala Ala
                610                 615                 620

His Val Lys Gln Val Leu Leu His Gln Gln Ala Leu Phe Gly Lys Asn
625                 630                 635                 640

Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
                660                 665                 670

Arg Pro Thr Tyr Glu Glu Tyr Leu Gly Thr Glu Tyr Val Thr Ala Ile
                675                 680                 685

Ala Asn Leu Lys Lys Cys Ser Thr Ser Pro Leu Leu Glu Ala Cys Ala
690                 695                 700

Phe Leu Thr Arg
705

<210> SEQ ID NO 8
<211> LENGTH: 692
<212> TYPE: PRT
<213> ORGANISM: Homo sapiens

<400> SEQUENCE: 8

Gly Arg Arg Arg Ser Val Gln Trp Cys Ala Val Ser Gln Pro Glu
1               5                   10                  15

Ala Thr Lys Cys Phe Gln Trp Gln Arg Asn Met Arg Lys Val Arg Gly
                20                  25                  30

Pro Pro Val Ser Cys Ile Lys Arg Asp Ser Pro Ile Gln Cys Ile Gln
                35                  40                  45

Ala Ile Ala Glu Asn Arg Ala Asp Ala Val Thr Leu Asp Gly Gly Phe
50                  55                  60

Ile Tyr Glu Ala Gly Leu Ala Pro Tyr Lys Leu Arg Pro Val Ala Ala
65                  70                  75                  80

Glu Val Tyr Gly Thr Glu Arg Gln Pro Arg Thr His Tyr Tyr Ala Val
                85                  90                  95

Ala Val Val Lys Lys Gly Gly Ser Phe Gln Leu Asn Glu Leu Gln Gly
                100                 105                 110
```

-continued

```
Leu Lys Ser Cys His Thr Gly Leu Arg Arg Thr Ala Gly Trp Asn Val
            115                 120                 125

Pro Ile Gly Thr Leu Arg Pro Phe Leu Asn Trp Thr Gly Pro Pro Glu
130                 135                 140

Pro Ile Glu Ala Ala Val Ala Arg Phe Phe Ser Ala Ser Cys Val Pro
145                 150                 155                 160

Gly Ala Asp Lys Gly Gln Phe Pro Asn Leu Cys Arg Leu Cys Ala Gly
                165                 170                 175

Thr Gly Glu Asn Lys Cys Ala Phe Ser Ser Gln Glu Pro Tyr Phe Ser
            180                 185                 190

Tyr Ser Gly Ala Phe Lys Cys Leu Arg Asp Gly Ala Gly Asp Val Ala
            195                 200                 205

Phe Ile Arg Glu Ser Thr Val Phe Glu Asp Leu Ser Asp Glu Ala Glu
210                 215                 220

Arg Asp Glu Tyr Glu Leu Leu Cys Pro Asp Asn Thr Arg Lys Pro Val
225                 230                 235                 240

Asp Lys Phe Lys Asp Cys His Leu Ala Arg Val Pro Ser His Ala Val
                245                 250                 255

Val Ala Arg Ser Val Asn Gly Lys Glu Asp Ala Ile Trp Asn Leu Leu
            260                 265                 270

Arg Gln Ala Gln Glu Lys Phe Gly Lys Asp Lys Ser Pro Lys Phe Gln
            275                 280                 285

Leu Phe Gly Ser Pro Ser Gly Gln Lys Asp Leu Leu Phe Lys Asp Ser
            290                 295                 300

Ala Ile Gly Phe Ser Arg Val Pro Pro Arg Ile Asp Ser Gly Leu Tyr
305                 310                 315                 320

Leu Gly Ser Gly Tyr Phe Thr Ala Ile Gln Asn Leu Arg Lys Ser Glu
                325                 330                 335

Glu Glu Val Ala Ala Arg Arg Ala Arg Val Val Trp Cys Ala Val Gly
            340                 345                 350

Glu Gln Glu Leu Arg Lys Cys Asn Gln Trp Ser Gly Leu Ser Glu Gly
            355                 360                 365

Ser Val Thr Cys Ser Ser Ala Ser Thr Thr Glu Asp Cys Ile Ala Leu
            370                 375                 380

Val Leu Lys Gly Glu Ala Asp Ala Met Ser Leu Asp Glu Gly Tyr Val
385                 390                 395                 400

Tyr Thr Ala Gly Lys Cys Gly Leu Val Pro Val Leu Ala Glu Asn Tyr
                405                 410                 415

Lys Ser Gln Gln Ser Ser Asp Pro Asp Pro Asn Cys Val Asp Arg Pro
            420                 425                 430

Val Glu Gly Tyr Leu Ala Val Ala Val Val Arg Arg Ser Asp Thr Ser
            435                 440                 445

Leu Thr Trp Asn Ser Val Lys Gly Lys Lys Ser Cys His Thr Ala Val
450                 455                 460

Asp Arg Thr Ala Gly Trp Asn Ile Pro Met Gly Leu Leu Phe Asn Gln
465                 470                 475                 480

Thr Gly Ser Cys Lys Phe Asp Glu Tyr Phe Ser Gln Ser Cys Ala Pro
                485                 490                 495

Gly Ser Asp Pro Arg Ser Asn Leu Cys Ala Leu Cys Ile Gly Asp Glu
            500                 505                 510

Gln Gly Glu Asn Lys Cys Val Pro Asn Ser Asn Glu Arg Tyr Tyr Gly
            515                 520                 525

Tyr Thr Gly Ala Phe Arg Cys Leu Ala Glu Asn Ala Gly Asp Val Ala
```

```
                530             535             540
Phe Val Lys Asp Val Thr Val Leu Gln Asn Thr Asp Gly Asn Asn Asn
545                 550                 555                 560

Glu Ala Trp Ala Lys Asp Leu Lys Leu Ala Asp Phe Ala Leu Leu Cys
                565                 570                 575

Leu Asp Gly Lys Arg Lys Pro Val Thr Glu Ala Arg Ser Cys His Leu
                580                 585                 590

Ala Met Ala Pro Asn His Ala Val Val Ser Arg Met Asp Lys Val Glu
                595                 600                 605

Arg Leu Lys Gln Val Leu Leu His Gln Gln Ala Lys Phe Gly Arg Asn
                610                 615                 620

Gly Ser Asp Cys Pro Asp Lys Phe Cys Leu Phe Gln Ser Glu Thr Lys
625                 630                 635                 640

Asn Leu Leu Phe Asn Asp Asn Thr Glu Cys Leu Ala Arg Leu His Gly
                645                 650                 655

Lys Thr Thr Tyr Glu Lys Tyr Leu Gly Pro Gln Tyr Val Ala Gly Ile
                660                 665                 670

Thr Asn Leu Lys Lys Cys Ser Thr Ser Pro Leu Leu Glu Ala Cys Glu
                675                 680                 685

Phe Leu Arg Lys
            690

<210> SEQ ID NO 9
<211> LENGTH: 692
<212> TYPE: PRT
<213> ORGANISM: Homo sapiens

<400> SEQUENCE: 9

Gly Arg Arg Arg Ser Val Gln Trp Cys Ala Val Ser Gln Pro Glu
1               5                   10                  15

Ala Thr Lys Cys Phe Gln Trp Gln Arg Asn Met Arg Arg Val Arg Gly
                20                  25                  30

Pro Pro Val Ser Cys Ile Lys Arg Asp Ser Pro Ile Gln Cys Ile Gln
                35                  40                  45

Ala Ile Ala Glu Asn Arg Ala Asp Ala Val Thr Leu Asp Gly Gly Phe
            50                  55                  60

Ile Tyr Glu Ala Gly Leu Ala Pro Tyr Lys Leu Arg Pro Val Ala Ala
65              70                  75                  80

Glu Val Tyr Gly Thr Glu Arg Gln Pro Arg Thr His Tyr Tyr Ala Val
                85                  90                  95

Ala Val Val Lys Lys Gly Gly Ser Phe Gln Leu Asn Glu Leu Gln Gly
                100                 105                 110

Leu Lys Ser Cys His Thr Gly Leu Arg Arg Thr Ala Gly Trp Asn Val
                115                 120                 125

Pro Ile Gly Thr Leu Arg Pro Phe Leu Asn Trp Thr Gly Pro Pro Glu
                130                 135                 140

Ser Ile Glu Ala Ala Val Ala Arg Phe Phe Ser Ala Ser Cys Val Pro
145                 150                 155                 160

Gly Ala Asp Lys Gly Gln Phe Pro Asn Leu Cys Arg Leu Cys Ala Gly
                165                 170                 175

Thr Gly Glu Asn Lys Cys Ala Phe Ser Ser Gln Glu Pro Tyr Phe Ser
                180                 185                 190

Tyr Ser Gly Ala Phe Lys Cys Leu Arg Asp Gly Ala Gly Asp Val Ala
                195                 200                 205
```

-continued

```
Phe Ile Arg Glu Ser Thr Val Phe Glu Asp Leu Ser Asp Glu Ala Glu
210                 215                 220
Arg Asp Glu Tyr Glu Leu Leu Cys Pro Asp Asn Thr Arg Lys Pro Val
225                 230                 235                 240
Asp Lys Phe Lys Asp Cys His Leu Ala Arg Val Pro Ser His Ala Val
            245                 250                 255
Val Ala Arg Ser Val Asn Gly Lys Glu Asp Ala Ile Trp Asn Leu Leu
            260                 265                 270
Arg Gln Ala Gln Glu Lys Phe Gly Lys Asp Lys Ser Pro Lys Phe Gln
        275                 280                 285
Leu Phe Gly Ser Pro Ser Gly Gln Lys Asp Leu Leu Phe Lys Asp Ser
290                 295                 300
Ala Ile Gly Phe Ser Arg Val Pro Pro Arg Ile Asp Ser Gly Leu Tyr
305                 310                 315                 320
Leu Gly Ser Gly Tyr Phe Thr Ala Ile Gln Asn Leu Arg Lys Ser Glu
                325                 330                 335
Glu Glu Val Ala Ala Arg Arg Ala Arg Val Val Trp Cys Ala Val Gly
            340                 345                 350
Glu Gln Glu Leu Arg Lys Cys Asn Gln Trp Ser Gly Leu Ser Glu Gly
        355                 360                 365
Ser Val Thr Cys Ser Ser Ala Ser Thr Thr Glu Asp Cys Ile Ala Leu
370                 375                 380
Val Leu Lys Gly Glu Ala Asp Ala Met Ser Leu Asp Gly Gly Tyr Val
385                 390                 395                 400
Tyr Thr Ala Gly Lys Cys Gly Leu Val Pro Val Leu Ala Glu Asn Tyr
                405                 410                 415
Lys Ser Gln Gln Ser Ser Asp Pro Asp Pro Asn Cys Val Asp Arg Pro
            420                 425                 430
Val Glu Gly Tyr Leu Ala Val Ala Val Val Arg Arg Ser Asp Thr Ser
        435                 440                 445
Leu Thr Trp Asn Ser Val Lys Gly Lys Lys Ser Cys His Thr Ala Val
450                 455                 460
Asp Arg Thr Ala Gly Trp Asn Ile Pro Met Gly Leu Leu Phe Asn Gln
465                 470                 475                 480
Thr Gly Ser Cys Lys Phe Asp Glu Tyr Phe Ser Gln Ser Cys Ala Pro
                485                 490                 495
Gly Ser Asp Pro Arg Ser Asn Leu Cys Ala Leu Cys Ile Gly Asp Glu
            500                 505                 510
Gln Gly Glu Asn Lys Cys Val Pro Asn Ser Asn Glu Arg Tyr Tyr Gly
        515                 520                 525
Tyr Thr Gly Ala Phe Arg Cys Leu Ala Glu Asp Ala Gly Asp Val Ala
530                 535                 540
Phe Val Lys Asp Val Thr Val Leu Gln Asn Thr Asp Gly Asn Asn Asn
545                 550                 555                 560
Glu Ala Trp Ala Lys Asp Leu Lys Leu Ala Asp Phe Ala Leu Leu Cys
                565                 570                 575
Leu Asp Gly Lys Arg Lys Pro Val Thr Glu Ala Arg Ser Cys His Leu
            580                 585                 590
Ala Met Ala Pro Asn His Ala Val Val Ser Arg Met Asp Lys Val Glu
        595                 600                 605
Arg Leu Lys Gln Val Leu Leu His Gln Gln Ala Lys Phe Gly Arg Asn
610                 615                 620
Gly Ser Asp Cys Pro Asp Lys Phe Cys Leu Phe Gln Ser Glu Thr Lys
```

```
                625                 630                 635                 640
Asn Leu Leu Phe Asn Asp Asn Thr Glu Cys Leu Ala Arg Leu His Gly
                    645                 650                 655

Lys Thr Thr Tyr Glu Lys Tyr Leu Gly Pro Gln Tyr Val Ala Gly Ile
                660                 665                 670

Thr Asn Leu Lys Lys Cys Ser Thr Ser Pro Leu Leu Glu Ala Cys Glu
                675                 680                 685

Phe Leu Arg Lys
        690

<210> SEQ ID NO 10
<211> LENGTH: 692
<212> TYPE: PRT
<213> ORGANISM: Homo sapiens

<400> SEQUENCE: 10

Gly Arg Arg Arg Ser Val Gln Trp Cys Ala Val Ser Gln Pro Glu
1               5                   10                  15

Ala Thr Lys Cys Phe Gln Trp Gln Arg Asn Met Arg Arg Val Arg Gly
                20                  25                  30

Pro Pro Val Ser Cys Ile Lys Arg Asp Ser Pro Ile Gln Cys Ile Gln
            35                  40                  45

Ala Ile Ala Glu Asn Arg Ala Asp Ala Val Thr Leu Asp Gly Gly Phe
50                  55                  60

Ile Tyr Glu Ala Gly Leu Ala Pro Tyr Lys Leu Arg Pro Val Ala Ala
65                  70                  75                  80

Glu Val Tyr Gly Thr Glu Arg Gln Pro Arg Thr His Tyr Tyr Ala Val
                85                  90                  95

Ala Val Val Lys Lys Gly Gly Ser Phe Gln Leu Asn Glu Leu Gln Gly
            100                 105                 110

Leu Lys Ser Cys His Thr Gly Leu Arg Arg Asn Ala Gly Trp Asn Val
            115                 120                 125

Pro Ile Gly Thr Leu Arg Pro Phe Leu Asn Trp Thr Gly Pro Pro Glu
        130                 135                 140

Pro Ile Glu Ala Ala Val Ala Arg Phe Phe Ser Ala Ser Cys Val Pro
145                 150                 155                 160

Gly Ala Asp Lys Gly Gln Phe Pro Asn Leu Cys Arg Leu Cys Ala Gly
                165                 170                 175

Thr Gly Glu Asn Lys Cys Ala Phe Ser Ser Gln Glu Pro Tyr Phe Ser
            180                 185                 190

Tyr Ser Gly Ala Phe Lys Cys Leu Arg Asp Gly Ala Gly Asp Val Ala
        195                 200                 205

Phe Ile Arg Glu Ser Thr Val Phe Glu Asp Leu Ser Asp Glu Ala Glu
    210                 215                 220

Arg Asp Glu Tyr Glu Leu Leu Cys Pro Asp Asn Thr Arg Lys Pro Val
225                 230                 235                 240

Asp Lys Phe Lys Asp Cys His Leu Ala Arg Val Pro Ser His Ala Val
                245                 250                 255

Val Ala Arg Ser Val Asn Gly Lys Glu Asp Ala Ile Trp Asn Leu Leu
            260                 265                 270

Arg Gln Ala Gln Glu Lys Phe Gly Lys Asp Lys Ser Pro Lys Phe Gln
        275                 280                 285

Leu Phe Gly Ser Pro Ser Gly Gln Lys Asp Leu Leu Phe Lys Asp Ser
    290                 295                 300
```

```
Ala Ile Gly Phe Ser Arg Val Pro Pro Arg Ile Asp Ser Gly Leu Tyr
305                 310                 315                 320

Leu Gly Ser Gly Tyr Phe Thr Ala Ile Gln Asn Leu Arg Lys Ser Glu
            325                 330                 335

Glu Glu Val Ala Ala Arg Arg Ala Arg Val Val Trp Cys Ala Val Gly
            340                 345                 350

Glu Gln Glu Leu Arg Lys Cys Asn Gln Trp Ser Gly Leu Ser Glu Gly
        355                 360                 365

Ser Val Thr Cys Ser Ser Ala Ser Thr Thr Glu Asp Cys Ile Ala Leu
    370                 375                 380

Val Leu Lys Gly Glu Ala Asp Ala Met Ser Leu Asp Gly Gly Tyr Val
385                 390                 395                 400

Tyr Thr Ala Gly Lys Cys Gly Leu Val Pro Val Leu Ala Glu Asn Tyr
            405                 410                 415

Lys Ser Gln Gln Ser Ser Asp Pro Asp Pro Asn Cys Val Asp Arg Pro
        420                 425                 430

Val Glu Gly Tyr Leu Ala Val Ala Val Val Arg Arg Ser Asp Thr Ser
    435                 440                 445

Leu Thr Trp Asn Ser Val Lys Gly Lys Lys Ser Cys His Thr Ala Val
450                 455                 460

Asp Arg Thr Ala Gly Trp Asn Ile Pro Met Gly Leu Leu Phe Asn Gln
465                 470                 475                 480

Thr Gly Ser Cys Lys Phe Asp Glu Tyr Phe Ser Gln Ser Cys Ala Pro
            485                 490                 495

Gly Ser Asp Pro Arg Ser Asn Leu Cys Ala Leu Cys Ile Gly Asp Glu
        500                 505                 510

Gln Gly Glu Asn Lys Cys Val Pro Asn Ser Asn Glu Arg Tyr Tyr Gly
    515                 520                 525

Tyr Thr Gly Ala Phe Arg Cys Leu Ala Glu Asp Ala Gly Asp Val Ala
530                 535                 540

Phe Val Lys Gly Val Thr Val Leu Gln Asn Thr Asp Gly Asn Asn Asn
545                 550                 555                 560

Glu Ala Trp Ala Lys Asp Leu Lys Leu Ala Asp Phe Ala Leu Leu Cys
            565                 570                 575

Leu Asp Gly Lys Arg Lys Pro Val Thr Glu Ala Arg Ser Cys His Leu
        580                 585                 590

Ala Met Ala Pro Asn His Ala Val Val Ser Arg Met Asp Lys Val Glu
    595                 600                 605

Arg Leu Lys Gln Val Leu Leu His Gln Gln Ala Lys Phe Gly Arg Asn
610                 615                 620

Gly Ser Asp Cys Pro Asp Lys Phe Cys Leu Phe Gln Ser Glu Thr Lys
625                 630                 635                 640

Asn Leu Leu Phe Asn Asp Asn Thr Glu Cys Leu Ala Arg Leu His Gly
            645                 650                 655

Lys Thr Thr Tyr Glu Lys Tyr Leu Gly Pro Gln Tyr Val Ala Gly Ile
        660                 665                 670

Thr Asn Leu Lys Lys Cys Ser Thr Ser Pro Leu Leu Glu Ala Cys Glu
    675                 680                 685

Phe Leu Arg Lys
    690

<210> SEQ ID NO 11
<211> LENGTH: 689
<212> TYPE: PRT
```

<213> ORGANISM: Bos taurus

<400> SEQUENCE: 11

```
Ala Pro Arg Lys Asn Val Arg Trp Cys Thr Ile Ser Gln Pro Glu Trp
1               5                   10                  15

Phe Lys Cys Arg Arg Trp Gln Trp Arg Met Lys Lys Leu Gly Ala Pro
            20                  25                  30

Ser Ile Thr Cys Val Arg Arg Ala Phe Ala Leu Glu Cys Ile Arg Ala
        35                  40                  45

Ile Ala Glu Lys Lys Ala Asp Ala Val Thr Leu Asp Gly Gly Met Val
50                  55                  60

Phe Glu Ala Gly Arg Asp Pro Tyr Lys Leu Arg Pro Val Ala Ala Glu
65                  70                  75                  80

Ile Tyr Gly Thr Lys Glu Ser Pro Gln Thr His Tyr Tyr Ala Val Ala
                85                  90                  95

Val Val Lys Lys Gly Ser Asn Phe Gln Leu Asp Gln Leu Gln Gly Arg
            100                 105                 110

Lys Ser Cys His Thr Gly Leu Gly Arg Ser Ala Gly Trp Val Ile Pro
        115                 120                 125

Met Gly Ile Leu Arg Pro Tyr Leu Ser Trp Thr Glu Ser Leu Glu Pro
130                 135                 140

Leu Gln Gly Ala Val Ala Lys Phe Phe Ser Ala Ser Cys Val Pro Cys
145                 150                 155                 160

Ile Asp Arg Gln Ala Tyr Pro Asn Leu Cys Gln Leu Cys Lys Gly Glu
                165                 170                 175

Gly Glu Asn Gln Cys Ala Cys Ser Ser Arg Glu Pro Tyr Phe Gly Tyr
            180                 185                 190

Ser Gly Ala Phe Lys Cys Leu Gln Asp Gly Ala Gly Asp Val Ala Phe
        195                 200                 205

Val Lys Glu Thr Thr Val Phe Glu Asn Leu Pro Glu Lys Ala Asp Arg
210                 215                 220

Asp Gln Tyr Glu Leu Leu Cys Leu Asn Asn Ser Arg Ala Pro Val Asp
225                 230                 235                 240

Ala Phe Lys Glu Cys His Leu Ala Gln Val Pro Ser His Ala Val Val
                245                 250                 255

Ala Arg Ser Val Asp Gly Lys Glu Asp Leu Ile Trp Lys Leu Leu Ser
            260                 265                 270

Lys Ala Gln Glu Lys Phe Gly Lys Asn Lys Ser Arg Ser Phe Gln Leu
        275                 280                 285

Phe Gly Ser Pro Pro Gly Gln Arg Asp Leu Leu Phe Lys Asp Ser Ala
290                 295                 300

Leu Gly Phe Leu Arg Ile Pro Ser Lys Val Asp Ser Ala Leu Tyr Leu
305                 310                 315                 320

Gly Ser Arg Tyr Leu Thr Thr Leu Lys Asn Leu Arg Glu Thr Ala Glu
                325                 330                 335

Glu Val Lys Ala Arg Tyr Thr Arg Val Val Trp Cys Ala Val Gly Pro
            340                 345                 350

Glu Glu Gln Lys Lys Cys Gln Gln Trp Ser Gln Gln Ser Gly Gln Asn
        355                 360                 365

Val Thr Cys Ala Thr Ala Ser Thr Thr Asp Asp Cys Ile Val Leu Val
370                 375                 380

Leu Lys Gly Glu Ala Asp Ala Leu Asn Leu Asp Gly Gly Tyr Ile Tyr
385                 390                 395                 400
```

```
Thr Ala Gly Lys Cys Gly Leu Val Pro Val Leu Ala Glu Asn Arg Lys
                405                 410                 415

Thr Ser Lys Tyr Ser Ser Leu Asp Cys Val Leu Arg Pro Thr Glu Gly
            420                 425                 430

Tyr Leu Ala Val Ala Val Val Lys Lys Ala Asn Glu Gly Leu Thr Trp
        435                 440                 445

Asn Ser Leu Lys Asp Lys Lys Ser Cys His Thr Ala Val Asp Arg Thr
    450                 455                 460

Ala Gly Trp Asn Ile Pro Met Gly Leu Ile Val Asn Gln Thr Gly Ser
465                 470                 475                 480

Cys Ala Phe Asp Glu Phe Phe Ser Gln Ser Cys Ala Pro Gly Arg Asp
                485                 490                 495

Pro Lys Ser Arg Leu Cys Ala Leu Cys Ala Gly Asp Asp Gln Gly Leu
            500                 505                 510

Asp Lys Cys Val Pro Asn Ser Lys Glu Lys Tyr Tyr Gly Tyr Thr Gly
        515                 520                 525

Ala Phe Arg Cys Leu Ala Glu Asp Val Gly Asp Val Ala Phe Val Lys
    530                 535                 540

Asn Asp Thr Val Trp Glu Asn Thr Asn Gly Glu Ser Thr Ala Asp Trp
545                 550                 555                 560

Ala Lys Asn Leu Asn Arg Glu Asp Phe Arg Leu Leu Cys Leu Asp Gly
                565                 570                 575

Thr Arg Lys Pro Val Thr Glu Ala Gln Ser Cys His Leu Ala Val Ala
            580                 585                 590

Pro Asn His Ala Val Val Ser Arg Ser Asp Arg Ala Ala His Val Lys
        595                 600                 605

Gln Val Leu Leu His Gln Gln Ala Leu Phe Gly Lys Asn Gly Lys Asn
    610                 615                 620

Cys Pro Asp Lys Phe Cys Leu Phe Lys Ser Glu Thr Lys Asn Leu Leu
625                 630                 635                 640

Phe Asn Asp Asn Thr Glu Cys Leu Ala Lys Leu Gly Gly Arg Pro Thr
                645                 650                 655

Tyr Glu Glu Tyr Leu Gly Thr Glu Tyr Val Thr Ala Ile Ala Asn Leu
            660                 665                 670

Lys Lys Cys Ser Thr Ser Pro Leu Leu Glu Ala Cys Ala Phe Leu Thr
        675                 680                 685

Arg

<210> SEQ ID NO 12
<211> LENGTH: 689
<212> TYPE: PRT
<213> ORGANISM: Bos taurus

<400> SEQUENCE: 12

Ala Pro Arg Lys Asn Val Arg Trp Cys Thr Ile Ser Gln Pro Glu Trp
1               5                   10                  15

Phe Lys Cys Arg Arg Trp Gln Trp Arg Met Lys Lys Leu Gly Ala Pro
            20                  25                  30

Ser Ile Thr Cys Val Arg Arg Ala Phe Ala Leu Glu Cys Ile Pro Gly
        35                  40                  45

Ile Ala Glu Lys Lys Ala Asp Ala Val Thr Leu Asp Gly Gly Met Val
    50                  55                  60

Phe Glu Ala Gly Arg Asp Pro Tyr Lys Leu Arg Pro Val Ala Ala Glu
65                  70                  75                  80
```

-continued

Ile Tyr Gly Thr Lys Glu Ser Pro Gln Thr His Tyr Ala Val Ala
              85                  90                  95

Val Val Lys Lys Gly Ser Asn Phe Gln Leu Asp Gln Leu Gln Gly Arg
            100                 105                 110

Lys Ser Cys His Thr Gly Leu Gly Arg Ser Ala Gly Trp Ile Ile Pro
            115                 120                 125

Met Gly Ile Leu Arg Pro Tyr Leu Ser Trp Thr Glu Ser Leu Glu Pro
        130                 135                 140

Leu Gln Gly Ala Val Ala Lys Phe Phe Ser Ala Ser Cys Val Pro Cys
145                 150                 155                 160

Ile Asp Arg Gln Ala Tyr Pro Asn Leu Cys Gln Leu Cys Lys Gly Glu
                165                 170                 175

Gly Glu Asn Gln Cys Ala Cys Ser Ser Arg Glu Pro Tyr Phe Gly Tyr
            180                 185                 190

Ser Gly Ala Phe Lys Cys Leu Gln Asp Gly Ala Gly Asp Val Ala Phe
        195                 200                 205

Val Lys Glu Thr Thr Val Phe Glu Asn Leu Pro Glu Lys Ala Asp Arg
    210                 215                 220

Asp Gln Tyr Glu Leu Leu Cys Leu Asn Asn Ser Arg Ala Pro Val Asp
225                 230                 235                 240

Ala Phe Lys Glu Cys His Leu Ala Gln Val Pro Ser His Ala Val Val
                245                 250                 255

Ala Arg Ser Val Asp Gly Lys Glu Asp Leu Ile Trp Lys Leu Leu Ser
            260                 265                 270

Lys Ala Gln Glu Lys Ser Gly Lys Asn Lys Ser Arg Ser Phe Gln Leu
        275                 280                 285

Phe Gly Ser Pro Pro Gly Gln Arg Asp Leu Leu Phe Lys Asp Ser Ala
    290                 295                 300

Leu Gly Phe Leu Arg Ile Pro Ser Lys Val Asp Ser Ala Leu Tyr Leu
305                 310                 315                 320

Gly Ser Arg Tyr Leu Thr Thr Leu Lys Asn Leu Arg Glu Thr Ala Glu
                325                 330                 335

Glu Val Lys Ala Arg Tyr Thr Arg Val Val Trp Cys Ala Val Gly Pro
            340                 345                 350

Glu Glu Gln Lys Lys Cys Gln Gln Trp Ser Gln Gln Ser Gly Gln Asn
        355                 360                 365

Val Thr Cys Ala Thr Ala Ser Thr Thr Asp Asp Cys Ile Val Leu Val
    370                 375                 380

Leu Lys Gly Glu Ala Asp Ala Leu Asn Leu Asp Gly Gly Tyr Ile Tyr
385                 390                 395                 400

Thr Ala Gly Lys Cys Gly Leu Val Pro Val Leu Ala Glu Asn Arg Lys
                405                 410                 415

Ser Ser Lys His Ser Ser Leu Asp Cys Val Leu Arg Pro Thr Glu Gly
            420                 425                 430

Tyr Leu Ala Val Ala Val Val Lys Lys Ala Asn Glu Gly Leu Thr Trp
        435                 440                 445

Asn Ser Leu Lys Asp Lys Lys Ser Cys His Thr Ala Val Asp Arg Thr
    450                 455                 460

Ala Gly Trp Asn Ile Pro Met Gly Leu Ile Val Asn Gln Thr Gly Ser
465                 470                 475                 480

Cys Ala Phe Asp Glu Phe Phe Ser Gln Ser Cys Ala Pro Gly Ala Asp
                485                 490                 495

Pro Lys Ser Arg Leu Cys Ala Leu Cys Ala Gly Asp Asp Gln Gly Leu

```
                    500                 505                 510
Asp Lys Cys Val Pro Asn Ser Lys Glu Lys Tyr Tyr Gly Tyr Thr Gly
            515                 520                 525

Ala Phe Arg Cys Leu Ala Glu Asp Val Gly Asp Val Ala Phe Val Lys
            530                 535                 540

Asn Asp Thr Val Trp Glu Asn Thr Asn Gly Glu Ser Thr Ala Asp Trp
545                 550                 555                 560

Ala Lys Asn Leu Asn Arg Glu Asp Phe Arg Leu Leu Cys Leu Asp Gly
            565                 570                 575

Thr Arg Lys Pro Val Thr Glu Ala Gln Ser Cys His Leu Ala Val Ala
            580                 585                 590

Pro Asn His Ala Val Val Ser Arg Ser Asp Arg Ala Ala His Val Lys
            595                 600                 605

Gln Val Leu Leu His Gln Gln Ala Leu Phe Gly Lys Asn Gly Lys Asn
            610                 615                 620

Cys Pro Asp Lys Phe Cys Leu Phe Lys Ser Glu Thr Lys Asn Leu Leu
625                 630                 635                 640

Phe Asn Asp Asn Thr Glu Cys Leu Ala Lys Leu Gly Gly Arg Pro Thr
            645                 650                 655

Tyr Glu Glu Tyr Leu Gly Thr Glu Tyr Val Thr Ala Ile Ala Asn Leu
            660                 665                 670

Lys Lys Cys Ser Thr Ser Pro Leu Leu Glu Ala Cys Ala Phe Leu Thr
            675                 680                 685

Arg

<210> SEQ ID NO 13
<211> LENGTH: 689
<212> TYPE: PRT
<213> ORGANISM: Bos taurus

<400> SEQUENCE: 13

Ala Pro Arg Lys Asn Val Arg Trp Cys Thr Ile Ser Gln Pro Glu Trp
1               5                   10                  15

Phe Lys Cys Arg Arg Trp Gln Trp Arg Met Lys Lys Leu Gly Ala Pro
            20                  25                  30

Ser Ile Thr Cys Val Arg Arg Ala Phe Ala Leu Glu Cys Ile Arg Ala
            35                  40                  45

Ile Ala Glu Lys Lys Ala Asp Ala Val Thr Leu Asp Gly Gly Met Val
            50                  55                  60

Phe Glu Ala Gly Arg Asp Pro Tyr Lys Leu Arg Pro Val Ala Ala Glu
65                  70                  75                  80

Ile Tyr Gly Thr Lys Glu Ser Pro Gln Thr His Tyr Tyr Ala Val Ala
            85                  90                  95

Val Val Lys Lys Gly Ser Asn Phe Gln Leu Asp Gln Leu Gln Gly Arg
            100                 105                 110

Lys Ser Cys His Thr Gly Leu Gly Arg Ser Ala Gly Trp Ile Ile Pro
            115                 120                 125

Met Gly Ile Leu Arg Pro Tyr Leu Ser Trp Thr Glu Ser Leu Glu Pro
            130                 135                 140

Leu Gln Gly Ala Val Ala Lys Phe Phe Ser Ala Ser Cys Val Pro Cys
145                 150                 155                 160

Ile Asp Arg Gln Ala Tyr Pro Asn Leu Cys Gln Leu Cys Lys Gly Glu
            165                 170                 175

Gly Glu Asn Gln Cys Ala Cys Ser Ser Arg Glu Pro Tyr Phe Gly Tyr
```

```
            180             185             190
Ser Gly Ala Phe Lys Cys Leu Gln Asp Gly Ala Gly Asp Val Ala Phe
            195                 200                 205

Val Lys Glu Thr Thr Val Phe Glu Asn Leu Pro Glu Lys Ala Asp Arg
    210                 215                 220

Asp Gln Tyr Glu Leu Leu Cys Leu Asn Asn Ser Arg Ala Pro Val Asp
225                 230                 235                 240

Ala Phe Lys Glu Cys His Leu Ala Gln Val Pro Ser His Ala Val Val
                245                 250                 255

Ala Arg Ser Val Asp Gly Lys Glu Asp Leu Ile Trp Lys Leu Leu Ser
        260                 265                 270

Lys Ala Gln Glu Lys Phe Gly Lys Asn Lys Ser Arg Ser Phe Gln Leu
    275                 280                 285

Phe Gly Ser Pro Pro Gly Gln Arg Asp Leu Leu Phe Lys Asp Ser Ala
290                 295                 300

Leu Gly Phe Leu Arg Ile Pro Ser Lys Val Asp Ser Ala Leu Tyr Leu
305                 310                 315                 320

Gly Ser Arg Tyr Leu Thr Thr Leu Lys Asn Leu Arg Glu Thr Ala Glu
                325                 330                 335

Glu Val Lys Ala Arg Tyr Thr Arg Val Val Trp Cys Ala Val Gly Pro
            340                 345                 350

Glu Glu Gln Lys Lys Cys Gln Gln Trp Ser Gln Ser Gly Gln Asn
            355                 360                 365

Val Thr Cys Ala Thr Ala Ser Thr Thr Asp Asp Cys Ile Val Leu Val
    370                 375                 380

Leu Lys Gly Glu Ala Asp Ala Leu Asn Leu Asp Gly Gly Tyr Ile Tyr
385                 390                 395                 400

Thr Ala Gly Lys Cys Gly Leu Val Pro Val Leu Ala Glu Asn Arg Lys
                405                 410                 415

Ser Ser Lys His Ser Ser Leu Asp Cys Val Leu Arg Pro Thr Glu Gly
            420                 425                 430

Tyr Leu Ala Val Ala Val Val Lys Lys Ala Asn Glu Gly Leu Thr Trp
            435                 440                 445

Asn Ser Leu Lys Asp Lys Lys Ser Cys His Thr Ala Val Asp Arg Thr
    450                 455                 460

Ala Gly Trp Asn Ile Pro Met Gly Leu Ile Val Asn Gln Thr Gly Ser
465                 470                 475                 480

Cys Ala Phe Asp Glu Phe Phe Ser Gln Ser Cys Ala Pro Gly Ala Asp
                485                 490                 495

Pro Lys Ser Arg Leu Cys Ala Leu Cys Ala Gly Asp Asp Gln Gly Leu
            500                 505                 510

Asp Lys Cys Val Pro Asn Ser Lys Glu Lys Tyr Tyr Gly Tyr Thr Gly
            515                 520                 525

Ala Phe Arg Cys Leu Ala Glu Asp Val Gly Asp Val Ala Phe Val Lys
            530                 535                 540

Asn Asp Thr Val Trp Glu Asn Thr Asn Gly Glu Ser Thr Ala Asp Trp
545                 550                 555                 560

Ala Lys Asn Leu Asn Arg Glu Asp Phe Arg Leu Leu Cys Leu Asp Gly
                565                 570                 575

Thr Arg Lys Pro Val Thr Glu Ala Gln Ser Cys His Leu Ala Val Ala
            580                 585                 590

Pro Asn His Ala Val Val Ser Arg Ser Asp Arg Ala Ala His Val Lys
            595                 600                 605
```

```
Gln Val Leu Leu His Gln Ala Leu Phe Gly Lys Asn Gly Lys Asn
    610                 615                 620
Cys Pro Asp Lys Phe Cys Leu Phe Lys Ser Glu Thr Lys Asn Leu Leu
625                 630                 635                 640
Phe Asn Asp Asn Thr Glu Cys Leu Ala Lys Leu Gly Gly Arg Pro Thr
                645                 650                 655
Tyr Glu Glu Tyr Leu Gly Thr Glu Tyr Val Thr Ala Ile Ala Asn Leu
                660                 665                 670
Lys Lys Cys Ser Thr Ser Pro Leu Leu Glu Ala Cys Ala Phe Leu Thr
                675                 680                 685
Arg

<210> SEQ ID NO 14
<211> LENGTH: 689
<212> TYPE: PRT
<213> ORGANISM: Bos taurus

<400> SEQUENCE: 14

Ala Pro Arg Lys Asn Val Arg Trp Cys Thr Ile Ser Gln Pro Glu Trp
1               5                   10                  15
Phe Lys Cys Arg Arg Trp Gln Trp Arg Met Lys Lys Leu Gly Ala Pro
                20                  25                  30
Ser Ile Thr Cys Val Arg Arg Ala Phe Ala Leu Ala Cys Ile Arg Ala
                35                  40                  45
Ile Ala Glu Lys Lys Ala Asp Ala Val Thr Leu Asp Gly Gly Met Val
            50                  55                  60
Phe Glu Ala Gly Arg Asp Pro Tyr Lys Leu Arg Pro Val Ala Ala Glu
65                  70                  75                  80
Ile Tyr Gly Thr Lys Glu Ser Pro Gln Thr His Tyr Tyr Ala Val Ala
                85                  90                  95
Val Val Lys Lys Gly Ser Asn Phe Gln Leu Asp Gln Leu Gln Gly Arg
                100                 105                 110
Lys Ser Cys His Thr Gly Leu Gly Arg Ser Ala Gly Trp Val Ile Pro
                115                 120                 125
Met Gly Ile Leu Arg Pro Tyr Leu Ser Trp Thr Glu Ser Leu Glu Pro
            130                 135                 140
Leu Gln Gly Ala Val Ala Lys Phe Phe Ser Ala Ser Cys Val Pro Cys
145                 150                 155                 160
Ile Asp Arg Gln Ala Tyr Pro Asn Leu Cys Gln Leu Cys Lys Gly Glu
                165                 170                 175
Gly Glu Asn Gln Cys Ala Cys Ser Ser Arg Glu Pro Tyr Phe Gly Tyr
                180                 185                 190
Ser Gly Ala Phe Lys Cys Leu Gln Asp Gly Ala Gly Asp Val Ala Phe
                195                 200                 205
Val Lys Glu Thr Thr Val Phe Glu Asn Leu Pro Glu Lys Ala Asp Arg
            210                 215                 220
Asp Gln Tyr Glu Leu Leu Cys Leu Asn Asn Ser Arg Ala Pro Val Asp
225                 230                 235                 240
Ala Phe Lys Glu Tyr His Leu Ala Gln Val Pro Ser His Pro Val Val
                245                 250                 255
Ala Arg Ser Val Asp Ala Lys Glu Asp Leu Ile Trp Lys Leu Leu Arg
                260                 265                 270
Lys Ala Gln Glu Lys Phe Gly Lys Asn Lys Ser Arg Ser Phe Gln Leu
                275                 280                 285
```

```
Phe Gly Ser Pro Pro Gly Gln Arg Asp Leu Leu Phe Lys Asp Ser Ala
    290                 295                 300
Leu Gly Phe Leu Arg Ile Pro Ser Lys Val Asp Ser Ala Leu Tyr Leu
305                 310                 315                 320
Gly Ser Arg Tyr Leu Thr Thr Leu Lys Asn Leu Arg Glu Thr Ala Glu
                325                 330                 335
Glu Val Lys Ala Arg Tyr Thr Arg Val Val Trp Cys Ala Val Gly Pro
            340                 345                 350
Glu Glu Gln Lys Lys Cys Gln Gln Trp Ser Gln Gln Ser Gly Gln Asn
        355                 360                 365
Val Thr Cys Ala Thr Ala Ser Thr Thr Asp Asp Cys Ile Val Leu Val
    370                 375                 380
Leu Lys Gly Glu Ala Asp Ala Leu Asn Leu Asp Gly Gly Tyr Val Tyr
385                 390                 395                 400
Thr Ala Gly Lys Cys Gly Leu Val Pro Val Leu Ala Glu Asn Arg Lys
                405                 410                 415
Ser Ser Lys His Ser Ser Leu Asp Cys Val Leu Arg Pro Thr Glu Gly
            420                 425                 430
Tyr Leu Ala Val Ala Val Val Arg Lys Ala Asn Glu Gly Leu Thr Trp
        435                 440                 445
Asn Ser Leu Lys Asp Lys Lys Ser Cys His Thr Ala Val Asp Arg Thr
    450                 455                 460
Ala Gly Trp Asn Ile Pro Met Gly Leu Ile Val Asn Gln Thr Gly Ser
465                 470                 475                 480
Cys Ala Phe Asp Glu Phe Phe Ser Gln Ser Cys Ala Pro Gly Ala Asp
                485                 490                 495
Pro Lys Ser Arg Leu Cys Ala Leu Cys Ala Gly Asp Asp Gln Gly Leu
            500                 505                 510
Asp Lys Cys Val Pro Asn Ser Lys Glu Lys Tyr Tyr Gly Tyr Thr Gly
        515                 520                 525
Ala Phe Arg Cys Leu Ala Glu Asp Val Gly Asp Val Ala Phe Val Lys
    530                 535                 540
Asn Asp Thr Val Trp Glu Asn Thr Asn Gly Glu Ser Thr Ala Asp Trp
545                 550                 555                 560
Ala Lys Asn Leu Asn Arg Glu Asp Phe Arg Leu Leu Cys Leu Asp Gly
                565                 570                 575
Thr Arg Lys Pro Val Thr Glu Ala Gln Ser Cys His Leu Ala Val Ala
            580                 585                 590
Pro Asn His Ala Val Val Ser Arg Ser Asp Arg Ala Ala His Val Lys
        595                 600                 605
Gln Val Leu Leu His Gln Gln Ala Leu Phe Gly Lys Asn Gly Lys Asn
    610                 615                 620
Cys Pro Asp Lys Phe Cys Leu Phe Lys Ser Glu Thr Lys Asn Leu Leu
625                 630                 635                 640
Phe Asn Asp Asn Thr Glu Cys Leu Ala Lys Leu Gly Gly Arg Pro Thr
                645                 650                 655
Tyr Glu Glu Tyr Leu Gly Thr Glu Tyr Val Thr Ala Ile Ala Asn Leu
            660                 665                 670
Lys Lys Cys Ser Thr Ser Pro Leu Leu Glu Ala Cys Ala Phe Leu Thr
        675                 680                 685
Arg
```

```
-continued

<210> SEQ ID NO 15
<211> LENGTH: 6
<212> TYPE: PRT
<213> ORGANISM: Homo sapiens

<400> SEQUENCE: 15

Gly Arg Arg Arg Arg Ser
1               5

<210> SEQ ID NO 16
<211> LENGTH: 4
<212> TYPE: PRT
<213> ORGANISM: Homo sapiens

<400> SEQUENCE: 16

Arg Lys Val Arg
1

<210> SEQ ID NO 17
<211> LENGTH: 4
<212> TYPE: PRT
<213> ORGANISM: Homo sapiens

<400> SEQUENCE: 17

Arg Arg Val Arg
1

<210> SEQ ID NO 18
<211> LENGTH: 26
<212> TYPE: PRT
<213> ORGANISM: Bos taurus

<400> SEQUENCE: 18

Phe Lys Cys Arg Arg Trp Gln Trp Arg Met Lys Lys Leu Gly Ala Pro
1               5                   10                  15

Ser Ile Thr Cys Val Arg Arg Ala Phe Ala
            20                  25

<210> SEQ ID NO 19
<211> LENGTH: 4
<212> TYPE: PRT
<213> ORGANISM: Bos taurus

<400> SEQUENCE: 19

Lys Cys Arg Arg
1

<210> SEQ ID NO 20
<211> LENGTH: 4
<212> TYPE: PRT
<213> ORGANISM: Bos taurus

<400> SEQUENCE: 20

Arg Met Lys Lys
1
```